(12) United States Patent
Yasugi et al.

(10) Patent No.: US 9,394,379 B2
(45) Date of Patent: Jul. 19, 2016

(54) PROCESS FOR PRODUCING WATER-SOLUBLE HYALURONIC ACID MODIFICATION

(71) Applicant: Chugai Seiyaku Kabushiki Kaisha, Kita-ku, Tokyo (JP)

(72) Inventors: Kenji Yasugi, Gotenba (JP); Teruo Nakamura, Gotenba (JP); Tsuyoshi Shimoboji, Gotenba (JP); Mika Sato, Gotenba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 206 days.

(21) Appl. No.: 13/947,716

(22) Filed: Jul. 22, 2013

(65) Prior Publication Data

US 2014/0011991 A1    Jan. 9, 2014

Related U.S. Application Data

(62) Division of application No. 13/430,259, filed on Mar. 26, 2012, now abandoned, which is a division of application No. 11/662,087, filed as application No. PCT/JP2005/016389 on Sep. 7, 2005, now Pat. No. 8,143,391.

(30) Foreign Application Priority Data

Sep. 7, 2004   (JP) ................. 2004/259157
Mar. 8, 2005   (JP) ................. 2005/064096
Mar. 8, 2005   (JP) ................. 2005/064122

(51) Int. Cl.
| | |
|---|---|
| C08B 37/08 | (2006.01) |
| C08J 3/075 | (2006.01) |
| A61K 47/48 | (2006.01) |
| C08J 3/12 | (2006.01) |
| C08L 5/08 | (2006.01) |

(52) U.S. Cl.
CPC ......... *C08B 37/0072* (2013.01); *A61K 47/4823* (2013.01); *C08J 3/075* (2013.01); *C08J 3/122* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 4,605,691 A | | 8/1986 | Balazs et al. |
| 5,688,931 A | | 11/1997 | Nogusa et al. |
| 5,760,200 A | * | 6/1998 | Miller et al. ............ 536/21 |
| 5,827,937 A | | 10/1998 | Ågerup |
| 5,888,988 A | | 3/1999 | Elson |
| 6,025,444 A | | 2/2000 | Waki et al. |
| 6,831,172 B1 | | 12/2004 | Barbucci et al. |
| 7,456,275 B2 | | 11/2008 | Shimoboji |
| 7,767,806 B2 | | 8/2010 | Hirakura et al. |
| 7,816,316 B2 | | 10/2010 | Hahn et al. |
| 2005/0153928 A1 | * | 7/2005 | Holick et al. .......... 514/54 |
| 2005/0164980 A1 | | 7/2005 | Shimoboji |
| 2006/0110458 A1 | | 5/2006 | Hahn et al. |
| 2007/0031503 A1 | | 2/2007 | Hirakura et al. |

FOREIGN PATENT DOCUMENTS

| | | |
|---|---|---|
| EP | 1564220 A1 | 8/2005 |
| JP | 61-138601 A | 6/1986 |
| JP | 05-85942 A | 4/1993 |
| JP | 05-140201 | 6/1993 |
| JP | 05-140201 A | 6/1993 |
| JP | 51-40201 A | 6/1993 |
| JP | 08-143604 A | 6/1996 |
| JP | 81-43604 A | 6/1996 |
| JP | 2001-524156 A | 11/2001 |
| JP | 2002-519481 | 7/2002 |
| JP | 2002-256075 B2 | 9/2002 |
| JP | 2002-529550 | 9/2002 |
| JP | 3445283 | 6/2003 |
| WO | 92/20349 A1 | 11/1992 |
| WO | 94/19376 A1 | 2/1994 |
| WO | 9402517 A1 | 2/1994 |
| WO | 9419376 A1 | 9/1994 |
| WO | 9515168 A1 | 6/1995 |
| WO | 9843664 A1 | 10/1998 |
| WO | 0001733 A1 | 1/2000 |

(Continued)

OTHER PUBLICATIONS

Matsuda, T. et al., Biomacromolecules, "Preparation of Vinylated Polysaccharides and Photofabrication of Tubular Scaffolds as Potential use in Tissue Engineering", 2002, vol. 3, pp. 942-950.*
Search report issued on Sep. 7, 2012, in copending Application No. 05782114.1 (6 pages).

(Continued)

*Primary Examiner* — Layla Berry
*Assistant Examiner* — Bahar Craigo
(74) *Attorney, Agent, or Firm* — Browdy and Neimark, P.L.L.C.

(57) ABSTRACT

The present invention provides a water-soluble modified HA practically used as a drug carrier and a production method thereof. The present invention provides: a water-soluble modified hyaluronic acid, the residence time in blood of which is elongated to a practical level, which is produced by introducing a substituent into the carboxy group of the glucuronic acid of hyaluronic acid or a derivative thereof, via an amide bond, at a lower limit of an introduction ratio of 5 mole % or more, using a BOP condensing agent in an aprotic polar solvent; and a production method thereof. Moreover, by cross-linking the modified hyaluronic acid, the present invention provides a hyaluronic acid gel capable of extremely long drug sustained-release even at the same cross-linking functional group introduction ratio as that of the conventionally known gel.

6 Claims, 27 Drawing Sheets

(56) References Cited

FOREIGN PATENT DOCUMENTS

| WO | 00/27887 | 5/2000 |
| --- | --- | --- |
| WO | 0027887 A2 | 5/2000 |
| WO | 01/05434 A2 | 1/2001 |
| WO | 01/60412 A2 | 8/2001 |
| WO | 03/087019 A1 | 10/2003 |
| WO | 2004/046200 A1 | 6/2004 |

OTHER PUBLICATIONS

Dorlands Medical Dictionary "rate"; also available at http://www.mercksource.com/pp/us/cns/cns-hl-dorlands-split.jsp?pg=/ppdocs/us/common/dorlands/dorland/seven/000090515.htm; last viewed Aug. 25, 2010.

Dorlands Medical Dictionary "rate"; also available at http://www.mercksource.com/pp/us/cns/cns—hl—dorlands—split.jsp?pg=/ppdocs/us/common/dorlands/dorland/seven/000090515.htm; last viewed Aug. 25, 2010.

Merriam-Webster Online Dictionary "derivative", also available at http://www.merriam-webster.com/dictionary/derivative; last viewed Jul. 15, 2009.

Park et al., Photopolymerized hyaluronic acid-based hydrogels and interpenetrating networks, Biomaterials, 24:893-900 (2003).

Search report issued on Sep. 7, 2012, in copending Application No. 05782114.2 (6 pages).

* cited by examiner

PROCESS FOR PRODUCING WATER-SOLUBLE HYALURONIC ACID MODIFICATION

This is a divisional of application Ser. No. 13/430,259, filed Mar. 26, 2012, which is a divisional of U.S. Pat. No. 8,143,391, issued Mar. 27, 2012, (application Ser. No. 11/662,087, filed Mar. 7, 2007), which is the U.S. National Phase application of International Application No. PCT/JP2005/016389, filed Sep. 7, 2005, such applications claiming the benefit under 35 U.S.C. §119 of the filing dates of Application No. 2004/259157 filed in Japan on Sep. 7, 2004; Application No. 2005/064096 filed in Japan on Mar. 8, 2005; and Application No. 2005/064122 filed in Japan on Mar. 8, 2005, the contents of each of which are incorporated herein by reference.

TECHNICAL FIELD

The present invention relates to a water-soluble modified hyaluronic acid useful as a drug carrier, a process for producing the modified hyaluronic acid, a conjugate consisting of the modified hyaluronic acid and a drug, and a gel obtained from the modified hyaluronic acid.

BACKGROUND ART

An attempt to conjugate a drug to a water-soluble polymer has been generally made for the purposes to improve properties such as prolonged residence time in blood, improved stability and solubility and reduced antigenicity of a low-molecular-weight drug, a peptide drug, a protein drug, or the like. In particular, polyethylene glycol (hereinafter also referred to as "PEG") has been widely used because of its inert properties and also because it has the effect of preventing adsorption of a protein to a drug in vivo. A PEG-conjugated protein has already been at the practical stage as a pharmaceutical. However, PEG is not a biodegradable polymer. Therefore, when a PEG-conjugated protein is accumulated in a body as a result of a long-term administration, problems regarding safety and the like have not yet been solved. Moreover, a phenomenon whereby the clearance of the $2^{nd}$ administration is abnormally accelerated in a PEG-conjugated liposome (Accelerated Blood Clearance phenomenon; hereinafter also referred to as "ABC phenomenon") has recently been reported (refer to Non-Patent Documents 1 and 2). Thus, it is hard to say that the safety and effectiveness of such a PEG-conjugated pharmaceutical has sufficiently been established.

Hyaluronic acid (hereinafter also referred to as "HA") is a polysaccharide isolated from the vitreous body of the bovine eye by K. Meyer in 1934. It has been well known as a main component of an extracellular matrix for a long time. HA is one type of glycosaminoglycan consisting of disaccharide units formed by connecting D-glucuronic acid to N-acetyl-glucosamine via a β (1→3) glycoside bond. Hyaluronic acid does not have species difference regarding the chemical and physical structure thereof, and a hyaluronic acid metabolic system exists also in humans. Furthermore, it can also be said that hyaluronic acid is an extremely safe biomaterial in terms of immunity and toxicity. In recent years, the aspect of hyaluronic acid as a physiologically active substance associated with cell adhesion, cell growth, and induction of cell migration has been focused. Further, as a result of the mass production of high-molecular-weight hyaluronic acid that has been succeeded using microorganisms, hyaluronic acid has been in the practical use as a pharmaceutical such as a therapeutic agent for articular disease. Still further, hyaluronic acid has also been practically used in the field of cosmetics, etc. Still further, it has been reported that conjugation of a drug to hyaluronic acid enables targeting of the drug to cancer tissues (refer to Patent Document 1), targeting to the liver (refer to Patent Document 2), a reduction in antigenicity (refer to Patent Document 3), elongation of the residence time in blood (refer to Patent Documents 4, 5, and 6), etc.

Compared with a generally used PEG, the use of hyaluronic acid as a drug conjugate carrier is advantageous in that HA has biodegradability, in that an enormous size of HA is available, and also in that since HA has many reactive sites in a molecule thereof, multiple drugs (a plurality of single drugs, or two or more drugs) can be linked in a single molecule. A use of hyaluronic acid having such advantages as a drug conjugate carrier becomes means for designing and developing a conjugate having higher functions to control drug pharmacokinetics, such as targeting or sustained-release. In addition, since hyaluronic acid is biodegradable and does not have species difference in terms of the chemical structure thereof, it can be said that such hyaluronic acid is a carrier that is more excellent than PEG from the viewpoint of safety as well.

However, it has been reported that the residence time of hyaluronic acid itself in blood is short, and that the half-life period thereof is 2 minutes after an intravenous injection (hereinafter also referred to as "iv") (refer to Non-Patent Document 3). Also in the studies by the present inventors, when hyaluronic acid was just conjugated to a drug, a significant elongation of the residence time of the drug in blood or the improvement of the persistence of the drug effect was not confirmed. The main metabolic sites of hyaluronic acid are liver and lymph gland. Such metabolism occurs as a result of incorporation of hyaluronic acid into cells via cell membrane-localized receptors that specifically bind to hyaluronic acid, which include CD44, RHAMM, and HARE as typical examples, and the subsequent decomposition by hyaluronidase. It has been reported that the main recognition sites of both of these molecules are contiguous free carboxy groups (hexasaccharide) of hyaluronic acid (refer to Non-Patent Document 4).

Accordingly, in order to overcome the problem of hyaluronic acid such as a short residence time in blood, an attempt has been made to use as a drug carrier a modified hyaluronic acid obtained by introducing a substituent into hyaluronic acid (refer to Patent Documents 4, 5, and 6). In general, when a substituent is introduced into hyaluronic acid, the residence time in blood is elongated, and it is considered that the degree of such elongation correlates to the introduction ratio of a substituent. A modified hyaluronic acid obtained by introducing substituents into various sites of hyaluronic acid has been reported. Among others, introduction of a substituent into a carboxy group in the glucuronic acid portion of hyaluronic acid via an amide bond that is hardly hydrolyzed is effective for inhibiting the obtained modified hyaluronic acid to bind to a hyaluronic acid receptor. Thus, it is considered that the modified hyaluronic acid is excellent in terms of the residence time in blood.

On the other hand, it has been reported that hyaluronic acid is converted to a tetrabutylammonium salt, and that the salt is then reacted with a substituent in dimethyl sulfoxide, so as to obtain a modified hyaluronic acid wherein the carboxy group of the hyaluronic acid has been amidated (refer to Patent Document 7). However, this invention has been made to prepare a cross-linked material, and it has not been intended to elongate the residence time in blood. What is more, 1,1-carbonyldiimidazole (hereinafter also referred to as "CDI") is used as a condensing agent in this invention. In our studies, it has been confirmed that although CDI is used as a condensing agent, it is not possible to obtain a hyaluronic acid derivative having a sufficiently elongated residence time in blood (which is sufficiently resistant to decomposition by hyaluronidase), and further that the molecular weight of hyaluronic acid is significantly decreased during the reaction.

Other than these reports, there has been reported a case where a substituent had been introduced into the carboxy group of hyaluronic acid in a mixed solvent consisting of water and a polar organic solvent (refer to Patent Document 8). However, whether or not the obtained modified hyaluronic acid brings on an elongation of the residence time in blood is not mentioned at all in this report.

Thus, a water-soluble modified hyaluronic acid that is practically used as a drug carrier, and in particular, a water-soluble modified hyaluronic acid whose residence time in blood has been extended up to a practical level, has been unknown. The production method thereof has also been unknown.

Pharmaceutical preparations of proteins or peptides having pharmacological effects, which have been practically used in recent years, generally have a short half-life period in blood. In addition, since the majority of them are injectable formulations that involve frequent administration, administration of such preparations imposes an enormous burden upon patients. Accordingly, it is desired that a practical sustained-release formulation of a protein or peptide drug, which exhibits drug effect even if it is used in an amount as small as possible, and the number of administration of which is also small, be developed. Moreover, a drug comprising a low-molecular-weight compound is highly required as a prolonged action drug because of its short half-life in blood.

For example, it has been attempted to prepare a sustained-release formulation composed of a biodegradable polymer such as polylactic acid-glycolic acid copolymer (hereinafter also referred to as "PLGA") as a substrate. However, regarding preparation of such a formulation, denaturation and aggregation of a protein caused by the hydrophobicity of the substrate, a drying process, and a decrease in pH, has been reported (refer to Non-Patent Documents 5 and 6). A sustained-release formulation using a hydrophilic hydrogel as a substrate has been reported. However, it has not yet been in practical use. To date, a sustained-release formulation, all of the encapsulation ratio of a protein or peptide, the recovery ratio, and safety of which reach the practical level, has not been realized.

A cross-linking method using, as a sustained-release substrate, HA that has nonantigenicity, nonmutagenicity, nontoxicity and biodegradability, and that is considered to be preferable in terms of safety, and the sustained-release of a protein or peptide drug from HA gel, have been frequently reported. Known methods of gelating HA via a chemical cross-link may include the carbodiimide method (refer to Patent Document 9), the divinyl sulfone method (refer to Patent Document 10), and the glycidylether method (refer to Patent Document 11). In general, in the case that a protein or peptide is encapsulated in gel by a method of introducing a protein or peptide after cross-linking, the introduction ratio is low due to problems such as compatibility of HA with a protein or peptide, electrostatic repulsion or the like. On the other hand, when in situ cross-linking is performed in the presence of a protein or peptide, there is an advantage in that a protein or peptide is deposited at a high encapsulation ratio. There have been reports regarding a formulation, whereby a protein or peptide is encapsulated in HA gel via such in situ cross-linking and is then subjected to sustained-release (refer to Patent Document 12, for example). However, if HA is subjected to in situ cross-linking by such a method in the presence of a protein or peptide, there is a problem in terms of the recovery ratio. For example, there has been a method of cross-linking an HA derivative (hereinafter also referred to as "HA-HZ"), into which a hydrazide group (hereinafter also referred to as "HZ") has been introduced, with a cross-linking agent consisting of an N-hydroxysuccinimide (hereinafter also referred to as "NHS") ester (refer to Patent Document 13). Since this method is applied for the purpose of in situ cross-linking under physiological conditions, a cross-link formation reaction is carried out at pH of 7.4 to 8.5. According to the studies of the present inventors, however, the recovery ratio of a protein or peptide obtained from HA gel by this method is low. This is because a part of a protein or peptide (mainly an amino group) is reacted with a cross-linking agent during the cross-linking reaction, and thus the protein is cross-linked. In addition, a denatured protein or peptide that remains in the gel has a decreased biological activity, and thus it is rather problematic in that it becomes an antigen. The release of the encapsulated drug at a high recovery ratio is an essential condition as a pharmaceutical. A method of chemically cross-linking and gelating HA without allowing a protein or peptide to react with a cross-linking agent has not yet been known. Moreover, as a method of encapsulation of a protein or peptide at a high recovery ratio, it has been reported that an unsaturated functional group is cross-linked via a nucleophilic addition reaction using polyethylene glycol (PEG) as a substrate (refer to Patent Document 14). However, this method is problematic in that non-biodegradable PEG fragments remain. In order to solve such problems, a hyaluronic acid gel, of which the reactivity with a protein or peptide is suppressed to a minimum, has been reported (refer to Patent Document 15). However, the sustained-release period thereof is only approximately 1 week.

Furthermore, in order to produce an injectable formulation from such a drug sustained-release substance, it is necessary to convert the above substance to fine particles. A spray dryer has been broadly used for such studies, and microparticulation of insulin (refer to Non-Patent Documents 7 and 8) and an rh anti-IgE antibody (refer to Non-Patent Document 9) has been reported. Further, encapsulation of a drug in fine particles of hyaluronic acid has also been reported (refer to Patent Documents 16 and 17). However, in these cases, since such fine particles are dissolved under the skin for a short time, the drug sustained-release period thereof is extremely short, and thus the practicability for sustained-release purpose is low. Furthermore, it has also been reported that a cross-linking reaction of chitosan is carried out during spray drying, so as to encapsulate a low-molecular-weight drug (refer to Non-Patent Document 10). However, in the case of this method, since the release period is short, like a few minutes, and since aldehyde used as a cross-linking agent has a high reactivity with a functional group such as an amino group, this method cannot be applied to a protein, a peptide, and other low-molecular-weight drugs having functional groups such as an amino group.

Thus, a practical sustained-release formulation using a water-soluble modified hyaluronic acid as a substrate has been unknown, and the production method thereof has also been unknown.

Patent Document 1: International Publication WO 92/06714

Patent Document 2: Japanese Patent Application No. 2001-81103 A

Patent Document 3: Japanese Patent Application No. 2-273176 A

Patent Document 4: Japanese Patent Application No. 5-85942 A

Patent Document 5: International Publication WO 01/05434

Patent Document 6: International Publication WO 01/60412

Patent Document 7: Japanese Patent Application No. 2002-519481 A

Patent Document 8: International Publication WO 94/19376

Patent Document 9: International Publication WO 94/02517

Patent Document 10: Japanese Patent Application No. 61-138601 A

Patent Document 11: Japanese Patent Application No. 5-140201 A

Patent Document 12: U.S. Pat. No. 5,827,937

Patent Document 13: International Publication WO 95/15168

Patent Document 14: International Publication WO 00/44808

Patent Document 15: International Publication WO 04/046200

Patent Document 16: Japanese Patent No. 3445283

Patent Document 17: International Publication WO 96/18647

Non-Patent Document 1: Int. J. Pharm., Vol. 255, pp. 167-174, 2003

Non-Patent Document 2: J. Control. Rel., Vol. 88, pp. 35-42, 2003

Non-Patent Document 3: J. Inter. Med., Vol. 242, pp. 27-33, 1997

Non-Patent Document 4: Exp. Cell Res., Vol. 228, pp. 216-228, 1996

Non-Patent Document 5: J. Pharm. Sci., Vol. 88, pp. 166-173, 1999

Non-Patent Document 6: J. Microencapsulation, Vol. 15, pp. 699-713, 1998

Non-Patent Document 7: Int. J. Pharm., Vol. 233, pp. 227-237, 2002

Non-Patent Document 8: J. Control. Rel. Vol. 91, pp. 385-394, 2003

Non-Patent Document 9: Biotech. and Bioeng., Vol. 60, pp. 301-309, 1998

Non-Patent Document 10: Int. J. Pharm., Vol. 187, pp. 53-65, 1999

DISCLOSURE OF THE INVENTION

Problems to be Solved by the Invention

It is an object of the present invention to provide: a water-soluble modified hyaluronic acid that is practically used as a drug carrier; a process for producing the above modified hyaluronic acid; a conjugate of the above modified hyaluronic acid and a drug; and a protein, a peptide, nucleic acid, or a low-molecular-weight compound, which is obtained from the above modified hyaluronic acid; or a hyaluronic acid gel with high safety, which encapsulates these components and a high-molecular-weight conjugate therein and enables a long-term sustained-release.

For the synthesis of a modified hyaluronic acid, when a substituent is introduced into hyaluronic acid via a dehydrative condensation reaction in water according to a method that is generally used in the synthesis of modified hyaluronic acids, the modification ratio of the carboxy group of hyaluronic acid is approximately 70% at the maximum. Thus, even though a modified hyaluronic acid was obtained by modifying carboxy groups of such hyaluronic acid to a maximum extent, it was insufficient as a practical drug carrier. For example, even in a case where hyaluronic acid having a high molecular weight (molecular weight: 580,000 daltons (Da)) was used as a drug carrier and where a modified hyaluronic acid was obtained by modifying 73 mole % of the carboxy group thereof, a mean residence time (MRT) in the blood of a rat was only approximately 16 hours, and thus it was insufficient as a practical drug carrier (Comparative Example 5-1 of the specification of the present application).

As a result of intensive studies directed towards solving the aforementioned problems, the present inventor has found that a water-soluble modified hyaluronic acid obtained by introducing a substituent into the carboxy group of the glucuronic acid of hyaluronic acid or a derivative thereof via an amide bond using a specific condensing agent in an aprotic polar solvent is able to elongate its residence time in blood to a practical level, which cannot be obtained using the conventional water-soluble modified hyaluronic acid. In addition, the inventor has also found that when compared with a gel cross-linked by the conventionally known method, a hyaluronic acid gel cross-linked with the obtained modified hyaluronic acid exhibits an extremely long sustained-release function at the same cross-linkable functional group introduction ratio, thereby completing the present invention.

In one aspect, the present invention provides a process for producing a water-soluble modified hyaluronic acid, which comprises a step of converting a carboxy group contained in the glucuronic acid portion of hyaluronic acid or a derivative thereof to a substituted amide group at a modification ratio of 5 mole % or more in an aprotic polar solvent, using a condensing agent represented by the following formula (II):

[Formula 1]

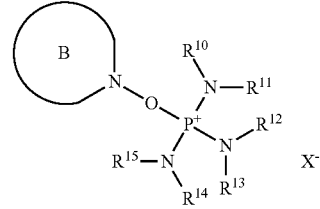

(II)

wherein each of $R^{10}$, $R^{11}$, $R^{12}$, $R^{13}$, $R^{14}$, and $R^{15}$ is independently selected from a $C_{1-6}$ alkyl group, or each of $R^{10}$ and $R^{11}$, $R^{12}$ and $R^{13}$, and $R^{14}$ and $R^{15}$ may independently form a nitrogen-containing heterocycle together with a nitrogen atom to which they are attached: ring B represents a monocyclic or condensed ring nitrogen-containing heterocyclic group that may be substituted; and $X^-$ represents an anion.

In one embodiment of the above aspect, the substituent of a substituted amide group generated as a result of the conversion of a carboxy group comprises at least one functional group. Herein, when multiple functional groups exist in the above substituent, such functional groups may be either of the same type, or of different types. In addition, all of the substituted amide groups contained in the above hyaluronic acid may be of the same type, or different types of substituted amide groups may be contained in the above modified hyaluronic acid.

Examples of the above functional group contained in a substituted amide group may include an amino group that may be substituted, a hydroxyl group, a mercapto group, a carboxy group, an aldehyde group, a methacryloyl group, and an acryloyl group. Preferred examples may include an amino group that may be substituted, a hydroxyl group, a mercapto group, a methacryloyl group, and an acryloyl group. Herein, the above functional group is preferably one or two types. When the above functional group is of two types, one of the two types is preferably a hydroxyl group. The total number of the above functional groups per substituted amide group is for example 1 to 10, preferably 1 to 9, and more preferably 1 to 4. When the total number of the above functional groups per substituted amide group is 2 or greater, it is preferable that one of them be a group other than a hydroxyl group and other groups be all hydroxyl groups, or that all the functional groups be hydroxyl groups. Examples of the substituent of the above substituted amide group may include: an aminoalkyl group (the alkylene chain of which may be substituted with one or more, namely, for example 1 to 9, preferably 1 to 8, and more preferably 1 to 3 hydroxyl groups. Hereinafter, this description is added to all of the term "aminoalkyl group"); an amino(polyalkyleneoxy)alkyl group; an amino(polyalkyleneamino)alkyl group; a hydroxyalkyl group (the alkylene chain of which may be substituted with one or more, namely, for example 1 to 9, preferably 1 to 8, and more preferably 1 to 3 hydroxyl groups. Hereinafter, this description is added to all of the term "hydroxyalkyl group"): a hydroxy(polyalkyleneoxy)alkyl group: a hydroxy(polyalkyleneamino)alkyl group; a mercaptoalkyl group; a mercapto(polyalkyleneoxy) alkyl group; a mercapto(polyalkyleneamino)alkyl group; a methacryloyloxyalkyl group; a methacryloylaminoalkyl group; a methacryloylamino(polyalkyleneoxy)alkyl group; a methacryloylamino(polyalkyleneamino)alkyl group; a methacryloyloxy(polyalkyleneoxy)alkyl group; a methacryloyloxy(polyalkyleneamino)alkyl group; an acryloyloxyalkyl group; an acryloylaminoalkyl group; an acryloylamino(polyalkyleneoxy)alkyl group; an acryloylamino(polyalkyleneamino)alkyl group; an acryloyloxy(polyalkyleneoxy)alkyl group; and an acryloyloxy(polyalkyleneamino)alkyl group.

More specific examples may include: an amino $C_{2-10}$ alkyl group (the alkylene chain of which may be substituted with one or more, preferably 1 to 8, and more preferably 1 to 3 hydroxyl groups); an amino(poly $C_{2-10}$ alkyleneoxy)alkyl group; an amino(poly $C_{2-10}$ alkyleneamino)alkyl group; a hydroxy $C_{2-10}$ alkyl group (the alkylene chain of which may be substituted with one or more, preferably 1 to 8, and more preferably 1 to 3 hydroxyl groups); a hydroxy(poly $C_{2-10}$ alkyleneoxy)alkyl group; a hydroxy(poly $C_{2-10}$ alkyleneamino)alkyl group; a mercapto $C_{2-10}$ alkyl group; a mercapto (poly $C_{2-10}$ alkyleneoxy)alkyl group; a mercapto(poly $C_{2-10}$ alkyleneamino)alkyl group; a methacryloyloxy $C_{2-6}$ alkyl group; a methacryloylamino $C_{2-6}$ alkyl group: a methacryloylamino(poly $C_{2-10}$ alkyleneoxy)alkyl group; a methacryloylamino(poly $C_{2-10}$ alkyleneamino)alkyl group; a methacryloyloxy(poly $C_{2-10}$ alkyleneoxy)alkyl group; a methacryloyloxy(poly $C_{2-10}$ alkyleneamino)alkyl group; an acryloyloxy $C_{2-6}$ alkyl group; an acryloylamino $C_{2-6}$ alkyl group; an acryloylamino(poly $C_{2-10}$ alkyleneoxy)alkyl group: an acryloylamino(poly $C_{2-10}$ alkyleneamino)alkyl group; an acryloyloxy(poly $C_{2-10}$ alkyleneoxy)alkyl group; and an acryloyloxy(poly $C_{2-10}$ alkyleneamino)alkyl group.

Herein, the type of a substituted amide group generated as a result of conversion of carboxy groups may be either singular or multiple. Multiple types mean 2 to 4 types, preferably 2 or 3 types, and more preferably 2 types. The process of the present invention for producing a water-soluble modified hyaluronic acid having multiple types of substituted amide groups generated as a result of conversion of carboxy groups may be a process, which comprises previously mixing multiple compounds having amino groups, and condensing the obtained mixture and carboxy groups contained in the glucuronic acid portion of hyaluronic acid or a derivative thereof. Otherwise, an operation to condense a compound having a primary amino group in amount to such an extent that all carboxy groups contained in the glucuronic acid portion of hyaluronic acid or a derivative thereof are not reacted, for example, in amount of 5 mole % to 95 mole %, and then to condense a compound having a secondary amino group to remaining carboxy groups, is performed, and thereafter, the same above operation may be repeated the necessary number of times. When multiple types of substituted amide groups are generated as a result of conversion of carboxy groups, the modification rates obtained during conversion of a carboxy group to each substituted amide group are added up, and the obtained value is defined as a modification ratio of carboxy groups contained in the glucuronic acid portion of hyaluronic acid or a derivative thereof. Specific examples of a combination of multiple substituted amide groups may include: an amide group substituted with an amino group that may be substituted and an amide group substituted with a hydroxyl group; an amide group substituted with an amino group that may be substituted and an amide group substituted with a mercapto group; an amide group substituted with an amino group that may be substituted and an amide group substituted with a methacryloyl group or an acryloyl group; an amide group substituted with a hydroxyl group and an amide group substituted with a mercapto group; an amide group substituted with a hydroxyl group and an amide group substituted with a methacryloyl group or an acryloyl group: an amide group substituted with a mercapto group and an amide group substituted with a methacryloyl group or an acryloyl group; an amide group substituted with an amino group that may be substituted, an amide group substituted with a hydroxyl group, and an amide group substituted with a mercapto group; an amide group substituted with an amino group that may be substituted, an amide group substituted with a hydroxyl group, and an amide group substituted with a methacryloyl group or an acryloyl group; an amide group substituted with an amino group that may be substituted, an amide group substituted with a mercapto group, and an amide group substituted with a methacryloyl group or an acryloyl group; an amide group substituted with a hydroxyl group, an amide group substituted with a mercapto group, and an amide group substituted with a methacryloyl group or an acryloyl group; and an amide group substituted with an amino group that may be substituted, an amide group substituted with a hydroxyl group, an amide group substituted with a mercapto group, and an amide group substituted with a methacryloyl group or an acryloyl group. Preferred examples of such a combination may include: an amide group substituted with an amino group that may be substituted and an amide group substituted with a hydroxyl group; an amide group substituted with a hydroxyl group and an amide group substituted with a mercapto group; and an amide group substituted with a hydroxyl group and an amide group substituted with a methacryloyl group or an acryloyl group. A more preferred example of such a combination is an amide group substituted with an amino group that may be substituted and an amide group substituted with a hydroxyl group.

More specifically, with regard to the following 4 groups (i) to (iv), combinations such as (i) and (ii); (i) and (iii); (i) and (iv); (ii) and (iii); (ii) and (iv); (iii) and (iv); (i), (ii), and (iii); (i), (ii), and (iv); (i), (iii), and (iv); (ii), (iii), and (iv); and (i), (ii), (iii), and (iv), are produced, and thereafter, any given group is selected from each group, so as to form combinations:

(i) an amide group substituted with an aminoalkyl group, an amide group substituted with an amino(polyalkyleneoxy)

alkyl group, and an amide group substituted with an amino (polyalkyleneamino)alkyl group;

(ii) an amide group substituted with a hydroxyalkyl group, an amide group substituted with a hydroxy(polyalkyleneoxy) alkyl group, and an amide group substituted with a hydroxy (polyalkyleneamino)alkyl group;

(iii) an amide group substituted with a mercaptoalkyl group, an amide group substituted with a mercapto(polyalkylencoxy)alkyl group, and an amide group substituted with a mercapto(polyalkyleneamino)alkyl group; and (iv) an amide group substituted with a methacryloyloxyalkyl group, an amide group substituted with a methacryloylaminoalkyl group, an amide group substituted with a methacryloylamino(polyalkyleneoxy)alkyl group, an amide group substituted with a methacryloylamino(polyalkyleneamino) alkyl group, an amide group substituted with a methacryloyloxy(polyalkyleneoxy)alkyl group, an amide group substituted with a methacryloyloxy(polyalkyleneamino)alkyl group, an amide group substituted with an acryloyloxyalkyl group, an amide group substituted with an acryloylaminoalkyl group, and an amide group substituted with an acryloylamino(polyalkyleneoxy)alkyl group, an acryloylamino (polyalkyleneamino)alkyl group, an acryloyloxy (polyalkyleneoxy)alkyl group, and an acryloyloxy (polyalkyleneamino)alkyl group.

Of these, combinations such as (i) and (ii), (ii) and (iii), and (ii) and (iv), are preferable. Further, combinations such as an amide group substituted with an aminoalkyl group and an amide group substituted with a hydroxyalkyl group, an amide group substituted with an aminoalkyl group and an amide group substituted with a hydroxy(polyalkyleneoxy)alkyl group, an amide group substituted with an amino(polyalkyleneoxy)alkyl group and an amide group substituted with a hydroxyalkyl group, and an amide group substituted with an amino(polyalkyleneoxy)alkyl group and an amide group substituted with a hydroxy(polyalkyleneoxy)alkyl group, are more preferable. Furthermore, the combination of an amide group substituted with an aminoalkyl group with an amide group substituted with a hydroxyalkyl group is particularly preferable.

The type of a substituted amide group generated as a result of conversion of a carboxy group is preferably a single type or two types.

Preferred examples of substituted amide groups generated as a result of conversion of a carboxy group and the combinations thereof may include: a single use of the substituted amide group described in each of the aforementioned groups (i), (iii), and (iv); the combination of these groups with an amide group substituted with a hydroxyalkyl group; and the combination of these groups with an amide group substituted with a hydroxy(polyalkyleneoxy)alkyl group.

Examples of compounds that are allowed to react with hyaluronic acid or a derivative thereof may include compounds represented by the following formulas:

$H_2N-CH_2-(CHR^5)_{m-2}-CH_2-NH_2;$ $H_2N-CH_2-CH_2-(Y^1-CH_2-CH_2)_n-NH_2;$ $H_2N-CH_2-(CHR^6)_{p-2}-CH_2-OH;$ $H_2N-CH_2-CH_2-(Y^2-CH_2-CH_2)_r-OH;$ $H_2N-(CH_2)_j-SR^7;$ $H_2N-CH_2-CH_2-(Y^3-CH_2-CH_2)_z-SR^8;$

$H_2N-(CH_2)_q-NHCO-C(R^{17})=CH_2;$

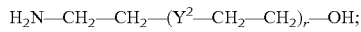 or

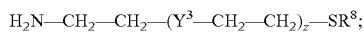
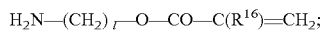

wherein each of m, l, p, j, and q independently represents an integer selected from 2 to 10; each of n, r, z, t, and y independently represents an integer selected from 1 to 200; each of $R^5$ and $R^6$ independently represents a hydrogen atom or a hydroxyl group; $R^7$ represents a hydrogen atom, a protective group, or $-S-(CH_2)_j-NH_2$; $R^8$ represents a hydrogen atom, a protective group, or $-S-(CH_2-CH_2-Y^3)_z-CH_2-CH_2-NH_2$; each of $R^{16}$, $R^{17}$, $R^{18}$, and $R^{19}$ independently represents a hydrogen atom or a methyl group; and each of $Y^1$, $Y^2$, $Y^3$, $Y^4$, and $Y^5$ independently represents an oxygen atom or $-NH-$.

When m is 4 or greater in $-(CHR^5)_{m-2}-$ in the above formula, $R^5$ is independently selected from each of a hydrogen atom or a hydroxyl group. Herein, $-(CHR^5)_{m-2}-$ is used to express, for example, a state wherein with regard to an (m-2) number of $-CHR^5-$, $-CH_2-$ and $-CHOH-$ are mixed at any given ratio in any given order. Such a state wherein with regard to an (m-2) number of $-CHR^5-$, $-CH_2-$ and $-CHOH-$ are mixed at any given ratio in any given order, includes a case where all of the (m-2) number of $-CHR^5-$ are $-CH_2-$ and $-CHOH-$. When m is 2, $-(CHR^5)_{m-2}-$ means a single bond.

When p is 4 or greater in $-(CHR^6)_{p-2}-$ in the above formula, $R^6$ is independently selected from each of a hydrogen atom or a hydroxyl group. Herein, $-(CHR^6)_{p-2}-$ is used to express, for example, a state wherein with regard to a (p-2) number of $-CHR^6-$, $-CH_2-$ and $-CHOH-$ are mixed at any given ratio in any given order. Such a state wherein with regard to a (p-2) number of $-CHR^6-$, $-CH_2-$ and $-CHOH-$ are mixed at any given ratio in any given order, includes a case where all of the (p-2) number of $-CHR^6-$ are $-CH_2-$ and $-CHOH-$. When p is 2, $-(CHR^6)_{p-2}-$ means a single bond.

The protective group represented by $R^7$ and $R^8$ means a protective group capable of protecting a mercapto group. Specific examples of such a protective group are described in T. W. Greene, P. G. M. Wuts, Protective Groups in Organic Synthesis, Third Edition, John Wiley & Sons, Inc., New York, 1999, for example. Among others, a group having no primary amino groups therein is preferable as a protective group. Moreover, $C_{1-4}$ alkylthio groups such as an ethylthio group or a t-butylthio group, and substituted phenylthio groups such as 2-nitrophenylthio group or a 2-carboxyphenylthio group, are more preferable. Furthermore, heteroarylthio groups such as a 2-pyridylthio group are also more preferable.

Preferred examples of $R^7$ may include $-S-(CH_2)-NH_2$ and a 2-pyridylthio group. Preferred examples of $R^5$ may include $-S-(CH_2-CH_2-Y^3)_z-CH_2-CH_2-NH_2$ and a 2-pyridylthio group.

The type of a compound to be reacted herein may be either singular or multiple. Such a compound to be reacted is preferably of a single type or two types.

Specific examples of a combination of several compounds to be reacted may include combinations, which are formed by producing combinations such as (i) and (ii); (i) and (iii); (i) and (iv); (ii) and (iii); (ii) and (iv); (iii) and (iv); (i), (ii), and (iii); (i), (ii), and (iv); (i), (iii), and (iv); (ii), (iii), and (iv); and (i), (ii), (iii), and (iv), with regard to the below mentioned 4 groups (i) to (iv), and then selecting any given compound from each group:

$H_2N-CH_2-(CHR^5)_{m-2}-CH_2-NH_2$, and $H_2N-CH_2-CH_2-(Y^1-CH_2-CH_2)_n-NH_2$; (i)

$H_2N-CH_2-(CHR^6)_{p-2}-CH_2-OH$, and $H_2N-CH_2-CH_2-(Y^2-CH_2-CH_2)_r-OH$; (ii)

$H_2N-(CH_2)_j-SR^7$, and $H_2N-CH_2-CH_2-(Y^3-CH_2-CH_2)_z-SR^5$; and (iii)

$H_2N-(CH_2)_l-O-CO-C(R^{16})=CH_2$, $H_2N-(CH_2)_q-NHCO-C(R^{17})=CH_2$, $H_2N-CH_2-(Y^4-CH_2-CH_2)_r-NHCO-C(R^{18})=CH_2$, and $H_2N-CH_2-CH_2-(Y^5-CH_2-CH_2)_y-O-CO-C(R^{19})=CH_2$. (iv)

Of these, combinations such as (i) and (ii), (ii) and (iii), and (ii) and (iv), are preferable, and further, combinations such as $H_2N-CH_2-(CHR^5)_{m-2}-CH_2-NH_2$ and $H_2N-CH_2-(CHR^6)_{p-2}-CH_2-OH$;

$H_2N-CH_2-(CHR^5)_{m-2}-CH_2-NH_2$ and $H_2N-CH_2-CH_2-(Y^2-CH_2-CH_2)_r-OH$;

$H_2N-CH_2-CH_2-(Y^1-CH_2-CH_2)_n-NH_2$ and $H_2N-CH_2-(CHR^6)_{p-2}-CH_2-OH$; and $H_2N-CH_2-CH_2-(Y^1-CH_2-CH_2)_n-NH_2$ and $H_2N-CH_2-CH_2-(Y^2-CH_2-CH_2)_r-OH$ are more preferable. Furthermore, the combination of $H_2N-CH_2-(CHR^5)_{m-2}-CH_2-NH_2$ with $H_2N-CH_2-(CHR^6)_{p-2}-CH_2-OH$ is particularly preferable.

Preferred examples of compounds to be reacted and the combinations thereof may include: a single use of the compounds described in each of the aforementioned groups (i), (iii), and (iv); the combination of these compounds with $H_2N-CH_2-(CHR^6)_{p-2}-CH_2-OH$; and the combination of these compounds with $H_2N-CH_2-CH_2-(Y^2-CH_2-CH_2)-OH$.

In another aspect, the present invention provides the above described process for producing a water-soluble modified hyaluronic acid, wherein the above described water-soluble modified hyaluronic acid comprises, in a molecule thereof, at least one repeating unit represented by the following formula (I):

[Formula 2]

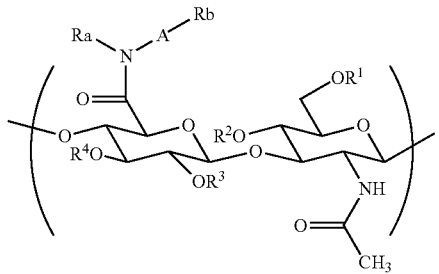

(I)

wherein each of $R^1$, $R^2$, $R^3$, and $R^4$ is independently selected from a hydrogen atom, a $C_{1-6}$ alkyl group, and a $C_{1-6}$ alkylcarbonyl group;

Ra represents a hydrogen atom or a $C_{1-6}$ alkyl group;

Rb represents a hydrogen atom, a $C_{1-6}$ alkyl group, or a group $-CO-C(R^{20})=CH_2$;

A represents $-CH_2-(CHR^5)_{m-2}-CH_2-NH-$, $-CH_2-CH_2-(Y^1-CH_2-CH_2)_n-NH-$, $-CH_2-(CHR^6)_{p-2}-CH_2-O-$, $-CH_2-CH_2-(Y^2-CH_2-CH_2)_r-O-$, $-(CH_2)_j-S-$, $-CH_2-CH_2-(Y^1-CH_2-CH_2)_z-S-$, $-(CH_2)_l-O-$, $-(CH_2)_q-NH-$, $-CH_2-CH_2-(Y^4-CH_2-CH_2)_t-NH-$, or $-CH_2-CH_2-(Y^5-CH_2-CH_2)_y-O-$, wherein each of m, l, p, j, and q independently represents an integer selected from 2 to 10, each of n, r, z, t, and y independently represents an integer selected from 1 and 200, each of $R^5$ and $R^6$ independently represents a hydrogen atom or a hydroxyl group, $R^{20}$ represents a hydrogen atom or a methyl group, and each of $Y^1$, $Y^2$, $Y^3$, $Y^4$, and $Y^5$ independently represents an oxygen atom or $-NH-$.

Herein, the type of -A-Rb may be either singular or multiple. The type of -A-Rb is preferably a single type or two types. Specific examples of a combination of several numbers of -A-Rb may include combinations formed by producing combinations such as (i) and (ii); (i) and (iii); (i) and (iv); (ii) and (iii); (ii) and (iv); (iii) and (iv); (i), (ii), and (iii); (i), (ii), and (iv); (i), (iii), and (iv); (ii), (iii), and (iv); and (i), (ii), (iii), and (iv), with regard to the below mentioned 4 groups (i) to (iv), and then selecting any given compound from each group:

$-CH_2-(CHR^5)_{m-2}-CH_2-NH_2$ and $-CH_2-CH_2-(Y^1-CH_2-CH_2)_n-NH_2$; (i)

$-CH_2-(CHR^6)_{p-2}-CH_2-OH$ and $-CH_2-CH_2-(Y^2-CH_2-CH_2)_r-OH$; (ii)

$-(CH_2)_j-SH$ and $H_2N-CH_2-CH_2-(Y^3-CH_2-CH_2)_z-SH$; and (iii)

$-(CH_2)_l-O-CO-C(R^{20})=CH_2$, $-(CH_2)_q-NHCO-C(R^{20})=CH_2$, $-CH_2-CH_2-(Y^4-CH_2-CH_2)_t-NHCO-C(R^{20})=CH_2$ and $-CH_2-CH_2-(Y^5-CH_2-CH_2)_y-O-CO-C(R^{20})=CH_2$. (iv)

Of these, combinations such as (i) and (ii), (ii) and (iii), and (ii) and (iv), are preferable, and further, combinations such as $-CH_2-(CHR^5)_{m-2}-CH_2-NH_2-$ and $-CH_2-(CHR^6)_{p-2}-CH_2-OH-$, $-CH_2-(CHR^5)_{m-2}-CH_2-NH_2-$ and $-CH_2-CH_2-(Y^2-CH_2-CH_2)_r-OH-$, $-CH_2-CH_2-(Y^1-CH_2-CH_2)_n-NH_2-$ and $-CH_2-(CHR^6)_{p-2}-CH_2-OH-$, and $-CH_2-CH_2-(Y^1-CH_2-CH_2)_n-NH_2-$ and $-CH_2-CH_2-(Y^2-CH_2-CH_2)_r-OH-$, are more preferable. Furthermore, a combination of -A-Rb such as $-CH_2-(CHR^5)_{m-2}-CH_2-NH_2-$ and $-CH_2-(CHR^6)_{p-2}-CH_2-OH$, is particularly preferable.

Preferred examples of -A-Rb and the combinations thereof may include: a single use of specific examples of -A-Rb described in each of the aforementioned groups (i), (iii), and (iv); the combination of these compounds with $-CH_2-(CHR^6)_{p-2}-CH_2-OH$; and the combination of these compounds with $-CH_2-CH_2-(Y^2-CH_2-CH_2)_r-OH$.

In one embodiment of the above aspect, the water-soluble modified hyaluronic acid comprising, in a molecule thereof, at least one repeating unit represented by the above formula (I) may be a compound represented by the following formula (III), for example:

[Formula 3]

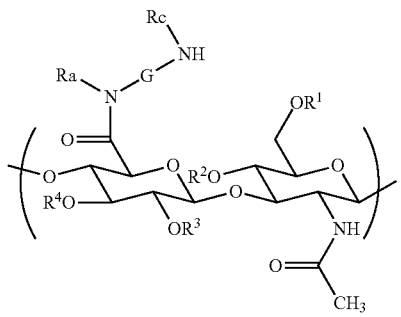

(III)

wherein $R^1$, $R^2$, $R^3$, $R^4$, and Ra are as defined above, and each of them is independently selected from a hydrogen atom, a $C_{1-6}$ alkyl group, and a $C_{1-6}$ alkylcarbonyl group;
Rc represents a hydrogen atom or a $C_{1-6}$ alkyl group;
G represents —$(CH_2)_m$— or —$CH_2$—$CH_2$—$(O$—$CH_2$—$CH_2)_{n'}$;
m represents an integer selected from 2 to 10; and
n' represents an integer selected from 1 to 10.

In one embodiment of the present invention, the modification ratio may be, for example, 30 mole % or more, and preferably 55 mole % or more. In another embodiment, the above modification ratio may be, for example, 70 mole % or less, preferably 60 mole % or less, and more preferably 30 mole % or less.

The above described modified hyaluronic acid may be used as a drug carrier. The above modified product includes those that are resistant to digestion by hyaluronidase. The mean residence time of the above described water-soluble modified hyaluronic acid in the blood of a mammal is, for example, 17 hours or longer, preferably 18 hours or longer, and more preferably 30 hours or longer.

In another aspect, the present invention provides the above described process for producing a water-soluble modified hyaluronic acid, which further comprises a step of amidating with dicarboxylic acid the amino group of a water-soluble modified hyaluronic acid, wherein, in formula (I), the terminus of -A-Rb is an amino group that may be substituted with a $C_{1-6}$ alkyl group, so as to introduce a carboxy group into the terminus of a substituent. Herein, dicarboxylic acid is not particularly limited. Examples of dicarboxylic acid used herein may include oxalic acid, a $C_{1-10}$ alkylene dicarboxylic acid, and a $C_{1-10}$ alkenylene dicarboxylic acid. Preferred dicarboxylic acid is succinic acid, maleic acid, glutaric acid, or adipic acid. The above described amidation is not particularly limited. For example, amidation can be carried out by reacting the amino group of the above described modified hyaluronic acid with a dicarboxylic anhydride.

In another aspect, the present invention provides a water-soluble modified hyaluronic acid obtained by the above described production method. The type of such a water-soluble modified hyaluronic acid is not particularly limited. A preferred example is a water-soluble modified hyaluronic acid, wherein the percentage of a peak area derived from disaccharide to the entire peak area derived from a decomposition product is 30% or less, when the above described water-soluble modified hyaluronic acid is decomposed with hyaluronidase that is able to decompose hyaluronic acid into disaccharide as a constitutional unit thereof and that generates an unsaturated disaccharide decomposition product having a Δ-4,5-glucuronic acid residue at the non-reducing terminus of the decomposition product, and when absorption of the obtained decomposition product at 232 nm is measured.

In another aspect, the present invention provides a drug carrier, which comprises the above described water-soluble modified hyaluronic acid. The type of the above drug carrier is not particularly limited. For example, it may be a particulate drug carrier, the surface of which is modified with the above described water-soluble modified hyaluronic acid.

In a further aspect, the present invention provides a pharmaceutical composition, which comprises the above described water-soluble modified hyaluronic acid.

In a further aspect, the present invention provides a water-soluble modified hyaluronic acid-drug conjugate, which comprises the above described water-soluble modified hyaluronic acid and a drug.

In a further aspect, the present invention provides a hyaluronic acid gel, which is obtained by cross-linking the above described modified hyaluronic acid. The above hyaluronic acid gel can be used for encapsulation of a drug, for example. The type of a drug to be encapsulated is not particularly limited herein. For example, it may be a conjugate consisting of a polymer and a drug. By drying this hyaluronic acid gel, the sustained-release property of a drug to be encapsulated can be further enhanced.

In a further aspect, the present invention provides a pharmaceutical composition, which comprises the above described hyaluronic acid gel.

In a further aspect, the present invention provides a medical device, which comprises the above described water-soluble modified hyaluronic acid. The type of the above medical device is not particularly limited. For example, it may be a medical device, the surface of which is modified with the above described water-soluble modified hyaluronic acid.

In a further aspect, the present invention provides a process for producing hyaluronic acid gel particles from the above described modified hyaluronic acid, which comprises the steps of:

(a) preparing a dilute solution comprising the above described modified hyaluronic acid;

(b) dispersing the above described solution into particulate droplets; and (c) conducting a cross-linking reaction of the above described polysaccharide derivative by concentration of a solution contained in the above described droplets. The above step (b) is not particularly limited herein. For example, it may be a step of spraying the above described solution, so as to disperse it into particulate droplets.

In a further aspect, the present invention provides a process for producing hyaluronic acid gel particles from the above described modified hyaluronic acid, which comprises the steps of:

(a) drying a hyaluronic acid gel;
(b) freezing the obtained dry product; and
(c) crushing the obtained frozen product. Herein, the hyaluronic acid gel can be obtained by cross-linking the modified hyaluronic acid of the present invention.

Moreover, the mean particle size of the obtained particles is not particularly limited. For example, it is between 0.01 μm and 150 μm, and preferably 0.1 μm and 50 μm. The thus obtained particle may be a drug carrier, and in particular, a drug sustained-release carrier.

In one embodiment of the above aspect, the dilute solution containing a drug before the cross-linking reaction in the above described production method, and the above drug is encapsulated by particles obtained after the cross-linking reaction.

In another aspect, the present invention provides a hyaluronic acid gel particle produced by the above described process, and a pharmaceutical composition comprising the above described hyaluronic acid gel particle.

The use of the water-soluble modified hyaluronic acid of the present invention enables elongation of the residence time in blood up to the practical level, which cannot be achieved by the conventional water-soluble modified hyaluronic acid. Accordingly, the use of the water-soluble modified hyaluronic acid of the present invention as a carrier for conjugating to a drug, or localization of the water-soluble modified hyaluronic acid of the present invention at least close to the surface of fine particles or gel that contain a drug, enables production of a practical and safe pharmaceutical composition, which has not been achieved by the prior art techniques.

In addition, the modified hyaluronic acid of the present invention is cross-linked and gelated, so as to provide a highly safe hyaluronic acid gel sustained-release formulation, which encapsulates a drug comprising a protein, a peptide, a low-molecular-weight compound, nucleic acid, or a conjugate of these components with a polymer, and which is capable of encapsulation and the sustained-release of such a drug for a long period of time.

BEST MODE FOR CARRYING OUT OF THE INVENTION

Figure 1:
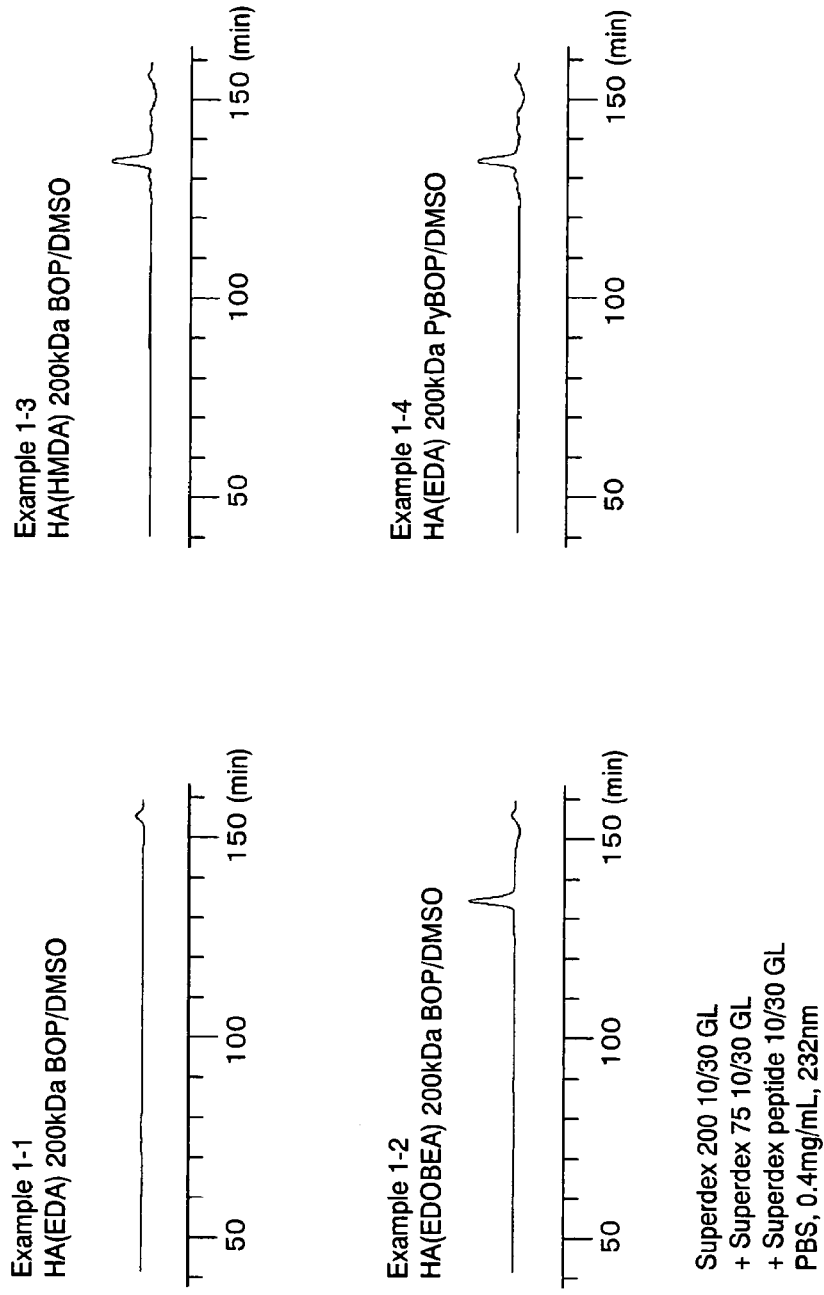
FIG. 1 shows an example of GPC charts obtained after treating the water-soluble modified hyaluronic acid of the present invention with hyaluronidase.

The present invention will be more specifically described below.

The present invention relates to a process for producing a water-soluble modified hyaluronic acid, which comprises introducing a substituent into a carboxy group of the glucuronic acid of hyaluronic acid or derivatives thereof at a lower limit of an introduction ratio of 5 mole % or more via an amino bond, using a specific condensing agent in an aprotic polar solvent.

The solvent must be a polar organic solvent. An aprotic polar solvent is particularly preferable. When a mixed solvent consisting of an aprotic polar solvent and water, or water is used as a solvent, even using any type of condensing agent, a modification ratio necessary for imparting practically sufficient retention ability in blood cannot be obtained. In addition, it is impossible to uniformly introduce cross-linkable functional groups, which realize an unprecedented long-term sustained-release of drug. Examples of a usable aprotic polar solvent may include dimethylformamide (hereinafter also referred to as "DMF"), dimethylacetamide (hereinafter also referred to as "DMAc"), dimethyl sulfoxide (hereinafter also referred to as "DMSO"), 1,3-dimethyl-2-imidazolidinone (hereinafter also referred to as "DMI"), sulfolane (hereinafter also referred to as "SF"), N-methylpyrrolidone (hereinafter also referred to as "NMP"), and a mixed solvent consisting of two or more of these solvents. Preferred examples of such a solvent may include dimethylformamide, dimethylacetamide, dimethyl sulfoxide, N-methylpyrrolidone, and a mixed solvent consisting of two or more solvents. A particularly preferred example is dimethyl sulfoxide.

In the production method of the present invention, a condensing agent represented by the following formula (II) is used:

[Formula 4]

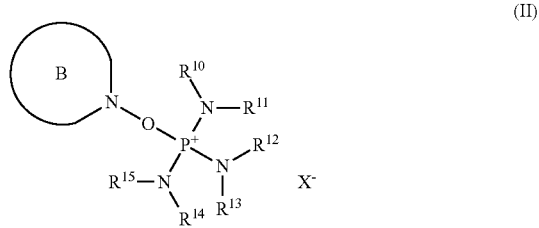

(II)

wherein $R^{10}$, $R^{11}$, $R^{12}$, $R^{13}$, $R^{14}$, $R^{15}$, ring B and $X^-$ are the same as those defined above. Herein, the type of ring B is not particularly limited, as long as it is a nitrogen-containing heterocyclic group having no acid protons. Ring B may also be substituted with a substituent such as a $C_{1-6}$ alkyl group or a halogen atom. Examples of such ring B may include pyrrolidin-2,5-dion-1-yl, 3,4,-dihydro-3-hydroxy-4-oxo-1,2,3-benzotriazine, and benzotriazol-1-yl. Examples of $X^-$ may include halide ions such as a fluoride ion, a chloride ion, a bromide ion, or an iodide ion, $CF_3SO_3^-$, $BF_4^-$, and $PF_6^-$.

A preferred example of a nitrogen-containing heterocycle that is formed by $R^{10}$ and $R^{11}$, $R^{12}$ and $R^{13}$, and $R^{14}$ and $R^{15}$, together with nitrogen atoms to which they are attached, is a 5- to 7-membered saturated nitrogen-containing heterocycle. Specific examples of such a heterocycle may include pyrrolidine, piperidine, and homopiperidine.

The above condensing agent is preferably a BOP condensing agent, ring B of which is benzotriazol-1-yl. Preferred examples of such a BOP condensing agent may include benzotriazol-1-yloxy-tris(dimethylamino)phosphonium hexafluorophosphate (hereinafter also referred to as "BOP"), benzotriazol-1-yloxy-tris(pyrrolidino) phosphonium hexafluorophosphate (hereinafter also referred to as "PyBOP"), and a mixture thereof. Such BOP condensing agents can be used singly or in combination, as appropriate.

When condensing agents other than those as above listed are used, such as N,N'-carbonyldiimidazole (hereinafter also referred to as "CDI"), N,N'-dicyclohexylcarbodiimide (hereinafter also referred to as "DCC"), 1-ethyl-3-(3-dimethylaminopropyl)carbodiimide hydrochloride (hereinafter also referred to as "EDC"), EDC/3,4-dihydro-3-hydroxy-4-oxo-1,2,3-benzotriazine (hereinafter also referred to as "HODhbt"), N-ethoxycarbonyl-2-ethoxy-1,2-dihydroquinoline (hereinafter also referred to as "EEDQ"), 4-(4,6-dimethoxy-1,3,5-triazine-2-yl)-4-methylmorpholiumchloride n-hydrate (hereinafter also referred to as "DMT-MM"), or 2-(1H-benzotriazol-1-yl)-1,1,3,3-tetramethyluronium tetrafluoroborate (hereinafter also referred to as "TBTU"), a modified hyaluronic acid having practically sufficient retention ability in blood (for example, a mean residence time in blood (hereinafter also referred to as "MRT") of 18 hours or longer) cannot be obtained. In addition, a high introduction ratio necessary for imparting resistance to digestion by hyaluronidase cannot be obtained either. Moreover, when CDI is used as a condensing agent, the molecular weight of HA is decreased during a condensation reaction, and thus it is not practical. Furthermore, it is impossible to carry out a uniform introduction of functional groups, which realizes an unprecedented long-term sustained-release of drug.

The type of hyaluronic acid (HA) used in the present invention is not particularly limited, as long as it has an HA skeleton. Such hyaluronic acid (HA) also includes a HA derivative wherein a part of HA has been converted to a derivative, HA whose molecular weight is reduced by enzyme or heat decomposition, and salts of HA and HA derivatives (sodium salts, potassium salts, magnesium salts, calcium salts, aluminum salts, etc.). A process of obtaining HA used in the present invention is not particularly limited. The origin of HA is not limited, and HA extracted from animal tissues. HA obtained by a fermentation process, HA obtained by chemical synthesis, or the like, can be used. In addition, in order to dissolve HA in an organic solvent, products obtained by ion exchange to counterions having high hydrophobicity, such as tetrabutylammonium salts, may also be used.

The ratio of carboxy groups converted to substituted amide groups in the water-soluble modified HA of the present invention is calculated as a carboxy group modification ratio based on the following formula:

$$\text{(Carboxy group modification ratio)} = \frac{\begin{pmatrix}\text{Total number of carboxy groups} \\ \text{modified in each molecule}\end{pmatrix}}{\begin{pmatrix}\text{Total number of glucuronic} \\ \text{acids in each molecule}\end{pmatrix}} \times 100$$

[Formula 5]

The lower limit of the carboxy group modification ratio of the water-soluble modified HA of the present invention may be 5% or more. From the viewpoint of the achievement of a practical residence time in blood when the modified hyaluronic acid is conjugated to a drug, the lower limit of the modification ratio is preferably 30 mole % or more, more preferably 50 mole % or more, further more preferably 55 mole % or more, and still further more preferably 60 mole % or more. In addition, the upper limit of the modification ratio may be 100 mole % or less. Specific examples of the modification ratio of a water-soluble modified hyaluronic acid used to bind to a protein and a peptide so as to form a conjugate may include 30 mole % to 100 mole %, 50 mole % to 100 mole %, and 60 mole % to 100 mole %. On the other hand, from the viewpoint of a modified hyaluronic acid used as a gel for realizing a long-term sustained-release of drug, the lower limit of the modification ratio is preferably 5 mole % or more, and more preferably 10 mole % or more. In addition, in order to maintain degradability under the skin, the upper limit of the modification ratio is preferably 70 mole % or less, more preferably 60 mole % or less, further more preferably 40 mole % or less, and still further more preferably 30 mole % or less. Specific examples of the range of the modification ratio of a water-soluble modified hyaluronic acid used as a substrate of a hydrogel for encapsulation of a protein and a peptide may include 5 mole % to 70 mole %, 5 mole % to 60 mole %, 5 mole % to 40 mole %. 5 mole % to 30 mole %, 10 mole % to 70 mole %, 10 mole % to 60 mole %, 10 mole % to 40 mole %, and 10 mole % to 30 mole %.

Herein, the carboxy group modification ratio can be quantified by $^1$H-NMR. Specifically, the above ratio can be obtained based on the comparison between the amount of an amino compound contained in an HA derivative that is aminated (hereinafter also referred to as "AM") or methacryloylated (hereinafter also referred to as "MA"), which is obtained by $^1$H-NMR, and an HA-derived peak. For example, the ratio between an amine compound-derived peak (2.9 to 3.1 ppm: measurement solvent $D_2O$) obtained by $^1$H-NMR performed on a modified hyaluronic acid (hereinafter also referred to as "HA-AM"), into which an amino group has been introduced using ethylenediamine (hereinafter also referred to as "EDA"), and an HA-derived peak (1.8 to 1.9 ppm: measurement solvent $D_2O$), or the ratio between a methacryloyl compound-derived peak (5.5 to 6.1, 1.8 ppm) obtained by $^1$H-NMR performed on HA-AEMA, into which a methacryloyl group has been introduced using aminoethyl methacrylate (hereinafter also referred to as "AEMA"), and an HA-derived peak (1.8 to 1.9 ppm), is actually measured.

From the viewpoint of a modified hyaluronic acid that has a practical residence time in blood when it is conjugated to a drug, the molecular weight of the water-soluble modified HA of the present invention has effect on its disposition. The residence time in blood of the water-soluble modified HA of the present invention also depends on the molecular weight of HA. The larger the molecular weight of HA, the longer the residence time in blood that can be achieved. Accordingly, by changing the molecular weight of a water-soluble modified HA and the modification ratio of carboxy groups contained in the water-soluble modified HA, the residence time in blood of the water-soluble modified HA can be regulated. The molecular weight of a raw material HA used in the present invention is not particularly limited. However, if the molecular weight of the raw material HA is extremely low, the residence time in blood of the obtained water-soluble modified HA becomes short. In contrast, if the molecular weight is too high, the viscosity of the obtained water-soluble modified HA of the present invention becomes extremely high, and thus it becomes difficult to administer the water-soluble modified HA in a high concentration. Moreover, the residence time in blood of the water-soluble modified HA of the present invention is hardly changed if the molecular weight thereof exceeds a certain weight. Thus, in general, the molecular weight of the raw material HA is preferably between 5,000 and 1,000,000 daltons, more preferably between 10,000 and 300,000 daltons, and further more preferably between 80,000 and 300,000 daltons, relative to the viscosity-average molecular weight.

On the other hand, when a modified hyaluronic acid is used as a substrate of a gel for realizing a long-term drug sustained-release, the molecular weight of the raw material HA used in the present invention is not particularly limited, and it is possible to use the raw material HA having any molecular weight. HA used herein has a molecular weight, for example, between 5,000 and 3,500,000 daltons, preferably between 10,000 and 2,000,000 daltons, and more preferably between 20,000 and 300,000 daltons.

It is to be noted that, as a method of measuring the weight-average molecular weight of HA, various types of known methods such as the light-scattering method, the osmotic pressure method, or the viscosity method, described in "Essential Kobunshi Kagaku (Essential Polymer Chemistry)" written by Seiichi Nakahama, (published by Kodansha Ltd., ISBN4-06-153310-X), can be applied. The viscosity-average molecular weight mentioned in the present specification can also be measured by methods generally applied in the technical field to which the present invention pertains, such as the use of a Ubbelohde viscometer.

The residence time in blood of a water-soluble modified HA obtained by the process of the present invention is preferably extended when compared with the residence time in blood of the raw material HA. Herein, the residence time in blood can appropriately be compared using known typical parameters such as mean residence time in blood (which is calculated in the form of MRT described in Example 5-3 of the present specification, for example), serum half-life (hereinafter also referred to as "t½"), or blood clearance (hereinafter also referred to as "Cl"). With regard to the residence time of a water-soluble modified HA obtained by the process of the present invention in the blood of mammals including humans, from the viewpoint of the practical use, the lower limit of the mean residence time in blood (hereinafter also referred to as "MRT") is preferably 18 hours or longer, and more preferably 30 hours or longer. From the viewpoint of the control of a drug concentration, the upper limit is 1 month or shorter, and preferably 2 weeks or shorter.

Moreover, in another aspect of the present invention, the water-soluble modified HA obtained by the process of the present invention preferably has resistance to digestion by hyaluronidase, when compared with the raw material HA. The expression "has resistance to digestion by hyaluronidase" is used herein to mean that when each of the raw material HA and the water-soluble modified HA of the present invention is decomposed by hyaluronidase, the modified product of the present invention has such a property that the decomposition ratio is slower than the raw material HA or its decomposition does not progress. For example, when the two above components are treated with hyaluronidase for a certain period of time, if a disaccharide decomposition peak observed in the raw material HA is not observed in the above modified product, it can be determined that the modified product has such a property that "the decomposition does not progress" (namely, it has resistance to digestion by hyaluronidase). It is to be noted that the decomposition ratio or decomposition state of HA can be observed by common methods such as gel permeation chromatography (hereinafter also referred to as "GPC").

In the present invention, the type of a substituent of an amide group introduced as a result of conversion of a carboxy group in the glucuronic acid portion is not particularly limited, as long as the modified HA obtained after the above conversion is water-soluble. The type of a substituent of the modified HA of the present invention is not particularly limited. In order to maintain the water-solubility of the obtained modified HA, it is preferable to introduce a hydrophilic substituent or a substituent having low hydrophobicity.

Specific examples of a compound that is allowed to react with hyaluronic acid or a derivative thereof during the aforementioned amidation are amines, which have a single type of one or more functional groups in a single molecule thereof and which have on a nitrogen atom thereof an amino group that may have a substituent. Herein, the functional group other than the amino group that may have a substituent on a nitrogen atom thereof is selected from an amino group that may be substituted, a hydroxyl group, a mercapto group, a carboxy group, an aldehyde group, a methacryloyl group, and an acryloyl group. The type of such a functional group is preferably one or two types. When the above compound has a single type of one functional group, the compound introducing into the carboxy group of the glucuronic acid of hyaluronic acid or a derivative thereof via an amide bond is selected from: a compound having two amino groups, such as an alkylene diamine compound or an amino(polyalkyleneoxy) alkylamine compound (hereinafter also referred to as a "diamine compound"); a compound having an amino group and a hydroxyl group; a compound having an amino group and a mercapto group; a compound having an amino group such as amino acid or peptide and a carboxy group; a compound having an amino group and an aldehyde group: a compound having an amino group and a methacryloyl group; and a compound having an amino group and an acryloyl group. The aforementioned compound may have a substituent in an amino group, and such a substituent includes a $C_{1-6}$ alkyl group and a $C_{1-6}$ alkylcarbonyl group.

In such a compound, any given carbon atoms in the compound may be substituted with, for example 1 to 9, preferably 1 to 8, and more preferably 1 to 3 hydroxyl groups. However, a single carbon atom is not substituted with several hydroxyl groups, and further, a carbon atom to which a heteroatom such as an oxygen atom or a nitrogen atom has already bound is not substituted with a hydroxyl group.

As stated above, the type of a compound that is allowed to react with hyaluronic acid or a derivative thereof during amidation may be either singular or multiple. That is to say, the compound may be either a single product or a mixture, and further, a single product may also be reacted in a stepwise manner.

Moreover, examples of a substituent of a substituted amide group generated as a result of conversion of the carboxy group of hyaluronic acid in such compounds may include: an aminoalkyl group (the alkylene chain of which may be substituted with at least one, for example 1 to 9, preferably 1 to 8, and more preferably 1 to 3 hydroxyl groups); an amino(polyalkyleneoxy)alkyl group; an amino(polyalkyleneamino) alkyl group; a hydroxyalkyl group (the alkylene chain of which may be substituted with at least one, for example 1 to 9, preferably 1 to 8, and more preferably 1 to 3 hydroxyl groups); a hydroxy(polyalkyleneoxy)alkyl group: a hydroxy (polyalkyleneamino)alkyl group; a mercaptoalkyl group; a mercapto(polyalkyleneoxy)alkyl group; a mercapto(polyalkyleneamino)alkyl group; a methacryloyloxyalkyl group; a methacryloylaminoalkyl group; a methacryloylamino(polyalkyleneoxy)alkyl group; a methacryloylamino(polyalkyleneamino)alkyl group; a methacryloyloxy(polyalkyleneoxy) alkyl group; a methacryloyloxy(polyalkyleneamino)alkyl group; an acryloyloxyalkyl group; an acryloylaminoalkyl group; an acryloylamino(polyalkyleneoxy)alkyl group; an acryloylamino(polyalkyleneamino)alkyl group: an acryloyloxy(polyalkyleneoxy)alkyl group; and an acryloyloxy(polyalkyleneamino)alkyl group.

In a certain embodiment, specific examples of a compound introducing into the carboxy group of the glucuronic acid of hyaluronic acid or a derivative thereof via an amide bond may include:

diamine compounds represented by the formulas $H_2N-CH_2-(CHR^5)_{m-2}-CH_2-NH_2$ and $H_2N-CH_2-CH_2-(Y^1-CH_2-CH_2)_n-NH_2$;

compounds having an amino group and a hydroxyl group represented by the formulas $H_2N-CH_2-(CHR^6)_{p-2}-CH_2-OH$ and $H_2N-CH_2-CH_2-(Y^2-CH_2-CH_2)_r-OH$;

compounds having an amino group and a mercapto group represented by the formulas $H_2N-(CH_2)_j-SR^7$ and $H_2N-CH_2-CH_2-(Y^3-CH_2-CH_2)_z-SR^8$; and compounds having an amino group and a methacryloyl group or an acryloyl group represented by the formulas $H_2N-(CH_2)_l-O-CO-C(R^{16})=CH_2$, $H_2N-(CH_2)_q-NHCO-C(R^{17})=CH_2$, $H_2N-CH_2-CH_2-(Y^4-CH_2-CH_2)_t-NHCO-C(R^{18})=CH_2$, and $H_2N-CH_2-CH_2-(Y^5-CH_2-CH_2)_y-O-CO-C(R^{19})=CH_2$. In the above formulas, each of m, l, p, j, and q independently represents an integer selected from 2 to 10; each of n, r, z, t, and y independently represents an integer selected from 1 and 200; each of $R^5$ and $R^6$ independently represents a hydrogen atom or a hydroxyl group: an (m-2) number of $-CHR^5-$ and a (p-2) number of $-CHR^6-$ represent a state wherein $-CH_2-$ and $-CHOH-$ are mixed at any given ratio in any given order; $R^7$ represents a hydrogen atom, a protective group, or $-S-(CH_2)_j-NH$; $R^8$ represents a hydrogen atom, a protective group, or $-S-(CH-CH_2-Y^3, -CH_2-CH_2-NH_2$; each of $R^{16}$, $R^{17}$, $R^{18}$, and $R^{19}$ independently represents a hydrogen atom or a methyl group; and each of $Y^1$, $Y^2$, $Y^3$, $Y^4$, and $Y^5$ independently represents an oxygen atom or $-NH-$.

Herein, each number of $CHR^5$ and $CHR^6$ wherein $R^5$ and $R^6$ are hydroxyl groups in molecules is 0 to 8, preferably 0 to 3, and more preferably 0 and 1. By controlling the numbers of $CHR^5$ and $CHR^6$ wherein $R^5$ and $R^6$ are hydroxyl groups, the solubility of the water-soluble modified HA of the present invention in water can be controlled. When $R^5$ is all hydrogen atoms, m is preferably between 2 and 6. Specific examples may include 2 and 6. When one of $R^5$ is a hydroxyl group, a specific example of m is 3. When $Y^1$ is an oxygen atom, a specific example of n is 2. When $Y^1$ is $-NH-$, a specific example of n is 1. A specific example of l is 1. A specific example of p and q is 3. Specific examples of r are 1 and 3.

Specific preferred examples of $H_2N-CH_2-(CHR^5)_{m-2}-CH_2-NH_2$ may include $H_2N-(CH_2)_2-NH_2$, $H_2N-(CH_2)_3-NH_2$, $H_2N-(CH_2)_4-NH_2$, $H_2N-(CH_2)_5-NH_2$, $H_2N-(CH_2)_6-NH_2$, $H_2N-(CH_2)_7-NH_2$, $H_2N-(CH_2)_8-NH_2$, $H_2N-(CH_2)_9-NH_2$, $H_2N-(CH_2)_{10}-NH_2$, $H_2N-CH_2-CHOH-CH_2-NH_2$, $H_2N-CH_2-CHOH-(CH_2)_2-NH_2$, $H_2N-CH_2-(CHOH)_2-CH_2-NH_2$, $H_2N-CH_2-CHOH-(CH_2)_3-NH_2$, $H_2N-(CH_2)_2-CHOH-(CH_2)_2-NH_2$, $H_2N-CH_2-(CHOH)_2-(CH_2)_2-NH_2$, $H_2N-(CH_2)_2-CHOH)_2-CH_2-NH_2$, $H_2N-CH_2-(CHOH)_3-CH_2-NH_2$, $H_2N-CH_2-CHOH-(CH_2)_4-NH_2$, $H_2N-(CH_2)_2-CHOH-(CH_2)_3-NH_2$, $H_2N-CH_2-(CHOH)_2-(CH_2)_3-NH_2$, $H_2N-CH_2-CHOH-CH_2-CHOH-(CH_2)_2-NH_2$, $H_2N-CH_2-CHOH-(CH_2)_2-CHOH-CH_2-NH_2$, $H_2N-(CH_2)_2-(CHOH)_2-(CH_2)_2-NH_2$, $H_2N-CH_2-(CHOH)_3-(CH_2)_2-NH_2$, $H_2N-CH_2-(CHOH)_2-CH_2-CHOH-CH_2-NH_2$, $H_2N-(CH_2)_2-CHOH-(CH_2)_4-NH_2$, $H_2N-(CH_2)_3-CHOH-(CH_2)_4-NH_2$, $H_2N-(CH_2)_2-CHOH-(CH_2)_6-NH_2$ and $H_2N-(CH_2)_5-CHOH-(CH_2)_4-NH_2$. Of these, $H_2N-(CH_2)_2-NH_2$, $H_2N-(CH_2)_6-NH_2$, and $H_2N-CH_2-CHOH-CH_2-NH_2$ are preferable.

Specific preferred examples of $H_2N-CH_2-(CHR^6)_{p-2}-CH_2-OH$ may include $H_2N-(CH_2)_2-OH$, $H_2N-(CH_2)_3-OH$, $H_2N-(CH_2)_4-OH$, $H_2N-(CH_2)_5-OH$, $H_2N-(CH_2)_6-OH$, $H_2N-(CH_2)_7-OH$, $H_2N-(CH_2)_8-OH$, $H_2N-(CH_2)_9-OH$, $H_2N-(CH_2)_{10}-OH$, $H_2N-CH_2-CHOH-CH_2-OH$, $H_2N-CH_2-CHOH-(CH_2)_2-OH$, $H_2N-CH_2-(CHOH)_2-CH_2-OH$, $H_2N-CH_2-CHOH-(CH_2)_3-OH$, $H_2N-(CH_2)_2-CHOH-(CH_2)_2-OH$, $H_2N-CH_2-(CHOH)_2-(CH_2)_2-OH$, H$_2$N—(CH$_2$—CHOH)$_2$—CH$_2$—OH, H$_2$N—CH$_2$—(CHOH)$_3$—CH$_2$—OH, H$_2$N—CH$_2$—CHOH—(CH$_2$)$_4$—OH, H$_2$N—(CH$_2$)$_2$—CHOH—(CH$_2$)$_3$—OH, H$_2$N—CH$_2$—(CHOH)$_2$—(CH$_2$)$_3$—OH, H$_2$N—CH$_2$—CHOH—CH$_2$—CHOH—(CH$_2$)$_2$—OH, H$_2$N—CH$_2$—CHOH—(CH$_2$)$_2$—CHOH—CH$_2$—OH, H$_2$N—(CH$_2$)$_2$—(CHOH)$_2$—(CH$_2$)$_2$—OH, H$_2$N—CH$_2$—(CHOH)$_3$—(CH$_2$)$_2$—OH, H$_2$N—CH$_2$—(CHOH)$_2$—CH$_2$—CHOH—CH$_2$—OH, H$_2$N—(CH$_2$)$_2$—CHOH—(CH$_2$)$_4$—OH, H$_2$N—(CH$_2$)$_3$—CHOH—(CH$_2$)$_4$—OH, H$_2$N—(CH$_2$)$_2$—CHOH—(CH$_2$)$_6$—OH and H$_2$N—(CH$_2$)$_5$—CHOH—(CH$_2$)$_4$—OH. Of these, H$_2$N—(CH$_2$)$_3$—OH and H$_2$N—CH$_2$—CHOH—CH$_2$—OH are preferable.

It is to be noted that these compounds are commercially available from Sigma-Aldrich, etc., and that the compounds are purchased from such companies as appropriate and are used. Otherwise, these compounds may also be synthesized in accordance with methods described in publications, or using such method described in publications for reference.

When a drug to be carried is a protein or a peptide, if the drug is encapsulated in a gel obtained from the water-soluble modified HA of the present invention, preferred examples of a compound that is allowed to react with hyaluronic acid or a derivative thereof may include: a compound having an amino group and a methacryloyl group; a compound having an amino group and an acryloyl group; a compound having an amino group and a mercapto group; the combination of a compound having an amino group and a methacryloyl group with a compound having an amino group and a hydroxyl group; the combination of a compound having an amino group and an acryloyl group with a compound having an amino group and a hydroxyl group; and the combination of a compound having an amino group and a mercapto group with a compound having an amino group and a hydroxyl group. In addition, when a drug is combined with the water-soluble modified HA of the present invention to form a conjugate, a diamine compound, a compound having an amino group and a mercapto group, the combination of a diamine compound with a compound having an amino group and a hydroxyl group, and the combination of a compound having an amino group and a mercapto group with a compound having an amino group and a hydroxyl group, are preferable.

Such a compound having an amino group and a hydroxyl group can be used to control the introduction ratio of a reactive functional group such as an amino group, a mercapto group, a methacryloyl group, and an acryloyl group, that is introduced into a carboxy group.

The term "alkyl group" is used in the present invention to mean a linear or branched chain alkyl group having one or more carbon atoms. Such an alkyl group includes a "$C_{1-6}$ alkyl group" as defined below, for example.

The term "$C_{1-6}$ alkyl group" is used in the present invention to mean a linear or branched chain alkyl group having 1 to 6 carbon atoms. Examples of such a $C_{1-6}$ alkyl group may include: "$C_{1-4}$ alkyl groups" such as methyl, ethyl, n-propyl, i-propyl, n-butyl, s-butyl, i-butyl, or t-butyl; and may further include n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl.

The term "$C_{1-6}$ alkylcarbonyl group" is used in the present invention to mean an alkylcarbonyl group having a linear or branched chain alkyl group containing 1 to 6 carbon atoms. Examples of such a $C_{1-6}$ alkylcarbonyl group may include acetyl, propionyl, butyryl, isobutyryl, pivaloyl, valeryl, isovaleryl, and hexanoyl.

The term "alkyleneoxy group" is used in the present invention to mean a divalent group, which contains an alkylene chain having one or more carbon atoms and connects with a carbon atom and an oxygen atom. An example of such an alkyleneoxy group is a "$C_{2-10}$ alkyleneoxy group" as defined below.

The term "$C_{2-10}$ alkyleneoxy group" is used to mean a divalent group, which contains an alkylene chain having 2 to 10 carbon atoms and connects with a carbon atom and an oxygen atom. Examples of such a $C_{2-10}$ alkyleneoxy group may include an ethyleneoxy group, a propyleneoxy group, and a butyleneoxy group.

In the present invention, the amount of substituents introduced can be controlled by the amount of a condensing agent that is added to HA.

Moreover, when the introduced substituent is cationic with regard to the electric charge of the water-soluble modified HA of the present invention, the total electric charge turns positive, and it results in a reduction in the residence time in blood. Thus, when the water-soluble modified HA of the present invention is combined with a drug to form a conjugate, so as to elongate the residence time in blood, the modification charge is preferably nonionic or anionic.

As a process of preparing the water-soluble modified HA of the present invention, for example. HA that has been converted to tetrabutylammonium (TBA) salts is dissolved in DMSO, and a diamino compound having an amino group on each of both ends of a molecule is then added thereto. Thereafter, carboxy groups of HA are condensed with a BOP condensing agent, so as to synthesize HA, into which an amino group has been introduced (hereinafter also referred to as "HA-AM").

Furthermore, with regard to the water-soluble modified HA of the present invention, when the substituent of a substituted amide group generated as a result of conversion of a carboxy group is an amino group that may be substituted, the amino group that may be substituted is further modified, so as to introduce functional groups such as a mercapto group, an acryloyl group, or a methacryloyl group. At that time, it is preferable for elongation of the residence time in blood that, for example, the remaining amino groups be treated with a dicarboxylic anhydride such as a succinic anhydride, a maleic anhydride, a glutaric anhydride, or an adipic anhydride, or be allowed to react with dicarboxylic acid such as maleic acid, glutaric acid, or adipic acid in the presence of a condensing agent, so as to convert the functional group at the terminus back to a carboxy group and so as to change total electric charge to be anionic. The type of a condensing agent used herein is not particular limited. Examples of such a condensing agent may include benzotriazol-1-yloxy-tris(dimethylamino)phosphonium hexafluorophosphate, benzotriazol-1-yloxy-tris(pyrrolidino)phosphonium hexafluorophosphate. N,N'-carbonyldiimidazole, N,N'-dicyclohexylcarbodiimide, 1-ethyl-3-(3-dimethylaminopropyl)carbodiimide hydrochloride, EDC/3,4-dihydro-3-hydroxy-4-oxo-1,2,3-benzotriazine, N-ethoxycarbonyl-2-ethoxy-1,2-dihydroquinoline, 4-(4,6-dimethoxy-1,3,5-triazin-2-yl)-4-methylmorpholiumchloride n-hydrate, 2-(1H-benzotriazol-1-yl)-1,1,3,3-tetramethyluronium tetrafluoroborate, and a mixture thereof. From the viewpoint of the total electric charge of the obtained modified hyaluronic acid, a compound obtained by reacting the amino group of amino acid or peptide with the carboxy group of hyaluronic acid or a derivative thereof, or a compound obtained by reacting with the carboxy group of hyaluronic acid or a derivative thereof, amines having both of (a) an amino group and (b) a functional group selected from a mercapto group, an acryloyl group, and a methacryloyl group, is also preferable.

Still further, the present invention also relates to a water-soluble modified hyaluronic acid itself obtained by the aforementioned production method.

From the viewpoint of a modified hyaluronic acid that obtains a practical residence time in blood when it is conjugated to a drug, this water-soluble modified hyaluronic acid is preferably characterized in that the upper limit of the percentage of a peak area derived from disaccharide to the entire peak area derived from a digestion product is 30% or less, when the above described water-soluble modified hyaluronic acid is decomposed with hyaluronidase that is able to decompose hyaluronic acid into disaccharide as a constitutional unit thereof and that generates an unsaturated disaccharide decomposition product having a Δ-4,5-glucuronic acid residue at the non-reducing terminus of the decomposition product (including the compound represented by formula IV set forth below, for example), and when absorption of the obtained decomposition product at 232 nm is measured:

[Formula 6]

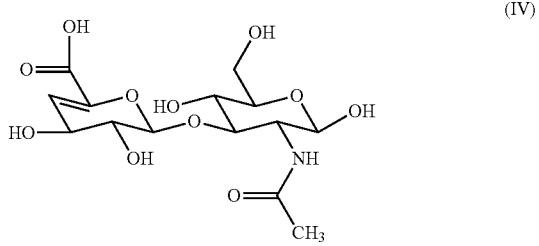

(IV)

The upper limit of the percentage of this peak area is preferably 20% or less, and more preferably 13% or less. In addition, the lower limit thereof may be 0% or more. The above measurement can be carried out by a method generally applied in the present technical field using a common high performance liquid chromatography. For example, a GPC column (for example, Superdex 200 10/300 GL, Superdex 75HR 10/30, and Superdex Peptide HR 10/30 (all of which are manufactured by Amersham Biosciences) can be used. Moreover, an eluent to be used is not particularly limited. For example, PBS (2 tablets of Phosphate Buffered Saline Tablets manufactured by Sigma-Aldrich are dissolved in 400 ml of purified water, for example) can be used.

Herein, the percentage of a peak area derived from disaccharide to the entire peak area derived from a decomposition product can be obtained by the following formula:

[Formula 7]

$$\text{Percentage of disaccharide (\%)} = \frac{\text{Peak area of disaccharide}}{\text{(Entire peak area of lysate)} - \text{entire peak area obtained when no enzymes are added}} \times 100$$

As such hyaluronidase, Hyaluronidase SD (manufactured by Seikagaku Corporation) or the like can be used.

From the viewpoint of a modified hyaluronic acid that obtains a practical residence time in blood when it is conjugated to a drug, the water-soluble modified HA of the present invention is not particularly limited. For example, it has solubility in water, such as 10 mg/ml to 1,000 mg/ml. Since the concentration of a modified HA is approximately 10 to 500 mg/ml when it is actually administered for the purpose of treatment, the solubility of the water-soluble modified HA of the present invention is preferably 10 mg/ml or greater in a normal saline solution at room temperature.

The water-soluble modified HA of the present invention can be used as a drug carrier. The type of a drug to be carried is not particularly limited, and a low-molecular-weight compound, a protein, a peptide, nucleic acid, or the like can be used. In addition, in order to allow the above modified HA to carry a drug, various types of known methods can be used. A drug may be encapsulated in a gel obtained from the water-soluble modified HA of the present invention, or a drug may be conjugated to the water-soluble modified HA of the present invention.

In order to prepare a conjugate consisting of the water-soluble modified HA of the present invention and a drug, a known method of conjugating a polymer to a drug can be used. Examples of a process applied herein may include:

the dehydration condensation reaction of the amino group of a water-soluble modified HA with the carboxy group of a drug;

the dehydration condensation reaction of the amino group of a drug with the carboxy group of a water-soluble modified HA;

the reaction of the amino group of a water-soluble modified HA with a drug, into which a modifying group such as isothiocyanate, isocyanate, acyl azide, N-hydroxysuccinimide (hereinafter also referred to as "NHS") ester, or epoxide, has been introduced;

the reaction of the amino group of a drug with a water-soluble modified HA, into which a modifying group such as isothiocyanate, isocyanate, acyl azide, NHS ester, or epoxide, has been introduced;

the Schiff base formation and reductive amination reaction of the amino group of a water-soluble modified HA with a drug, into which a carbonyl group such as aldehyde or ketone as a modifying group has been introduced;

the Schiff base formation and reductive amination reaction of the amino group of a drug with a water-soluble modified HA, into which a carbonyl group such as aldehyde or ketone as a modifying group has been introduced;

the reaction of a mercapto group introduced into a water-soluble modified HA with a drug, into which a modifying group such as maleimide, acryl ester, acrylamide, methacryl ester, methacrylamide, an allylated product, vinylsulfone, or a mercapto product, has been introduced;

the reaction of the mercapto group introduced into a drug with a water-soluble modified HA, into which a modifying group such as maleimide, acryl ester, acrylamide, methacryl ester, methacrylamide, an arylation product, vinylsulfone, or a mercapto product, has been introduced;

the bond of avidin introduced into a water-soluble modified HA with biotin introduced into a drug; and the bond of avidin introduced into a drug with biotin introduced into a water-soluble modified HA. In order to introduce such modifying groups (including groups derived from avidin and biotin) into a water-soluble modified HA or a drug, there is used a compound having, in a molecule thereof, two or more, and preferably two groups, which are arbitrarily selected from such modifying groups and a carboxy group (wherein the carboxy group may be converted to an active ester such as an NHS ester). The intramolecular structure of this compound other than the above described groups is not particularly limited, unless an inappropriate reaction progresses until a conjugate is prepared. The above compound can be acquired as a reagent, or it may also be synthesized based on known methods described in publications.

Specifically, the water-soluble modified HA of the present invention, wherein the substituent of a substituted amide group includes an amino group, is synthesized, and a portion of the amino group is then allowed to react with N-succinimidyl 3-[2-pyridyldithio]propionate (SPDP), so as to prepare HA, into which a mercapto group has been introduced (hereinafter also referred to as "HA-SH").

At that time, redundant amino groups are preferably treated with succinic anhydride, for example, so as to convert back to carboxy groups, and thus total electric charge is changed to be anionic. On the other hand, a modifying group that specifically reacts with a mercapto group is introduced into a protein, so as to form maleimide, vinylsulfone, etc. The thus obtained product may be allowed to react with HA-SH, so as to prepare a conjugate. To the contrary, the amino group of the water-soluble modified HA of the present invention, wherein the substituent of a substituted amide group includes an amino group, is allowed to react with maleimidobutyryloxy sulfosuccinimide, so as to prepare a water-soluble modified HA into which a maleimide group has been introduced (hereinafter also referred to as "HA-AM-MI"). Further, it may be allowed to react with a drug such as a mercapto group-containing protein or peptide, so as to prepare a conjugate. Otherwise, a portion of the amino group of the water-soluble modified HA of the present invention, wherein the substituent of a substituted amide group includes an amino group, is allowed to react with a maleimide group-containing compound such as Sulfo-KMUS (which is available from Dojindo Laboratories, PIERCE, etc.), so as to form HA-AM-MI. Redundant AM groups are treated with succinic anhydride or the like, for example. On the other hand, cysteine is introduced into a protein, or a linker having a mercapto group is allowed to react with it. The resultant is then allowed to react with HA-AM-MI, so as to prepare a conjugate.

Herein, in order to effectively maintain the biological activity of the above conjugate, the length of a spacer between a drug and the main chain of a water-soluble modified HA is controlled, or a site-specific conjugate is prepared.

Moreover, the present invention also relates to a hyaluronic acid gel obtained by cross-linking the above described water-soluble modified hyaluronic acid. A drug can be encapsulated in a drug sustained-release gel obtained from the water-soluble modified hyaluronic acid of the present invention, for example, by cross-linking a hyaluronic acid derivative, into which a methacryloyl group or an acryloyl group has been introduced, with a mercapto-containing compound in a solution in the coexistence of the drug. The term "cross-link" is used herein to include an intermolecular or intramolecular cross-link via a covalent bond. There are cases where both intermolecular and intramolecular cross-links are simultaneously included.

The pH used during cross-linking is not particularly limited. It is preferable to use pH, which prioritizes the selective reaction between an unsaturated group and a mercapto group without denaturation of a protein or peptide, and prevents the reaction with a protein- or peptide-containing amino group. Such a pH can be appropriately selected by persons skilled in the art. Such a pH range is, for example, between pH 6.0 and pH 9.5, and preferably between pH 7.0 and 9.5.

As a cross-linking agent used for the water-soluble modified HA of the present invention obtained by introducing a methacryloyl group into HA, a compound containing in a single molecule two or more mercapto groups that reacts with an unsaturated bond in a nucleophilic addition reaction is used. An example of such a cross-linking agent is, dithiothreitol (hereinafter also referred to as "DTT"), butanedithiol, polyethylene glycol dithiol, a peptide containing two or more cysteine residues and the like.

The type of a solvent used in a solution in which a drug coexists is not particularly limited, as long as the modified HA of the present invention and a drug to be encapsulated are dissolved therein and such a drug to be encapsulated is not denatured therein. Examples of such a solvent may include water, ethanol, acetone, isopropyl alcohol, acetonitrile, and a mixed solvent thereof. Preferred examples may include a mixed solvent consisting of water and ethanol, and water.

The ratio of mercapto groups to groups having an unsaturated bond is not particularly limited, and it can be appropriately selected by persons skilled in the art. In order to suppress the reaction with a protein or peptide to a minimum, and also in order to prevent unsaturated groups from remaining in the gel and to promote a rapid reaction, the ratio between mercapto groups and groups having an unsaturated bond is preferably between 3:1 and 1:3, and more preferably between 2:1 and 1:2.

Moreover, in order to improve the stability of a protein or peptide during the cross-linking reaction and also improve the reaction ratio, it is preferable to add a basic compound such as triethanolamine to the reaction system. At that time, a preferred concentration of such a basic compound is 10 to 20 µl/ml.

The present invention further relates to hyaluronic acid gel particles consisting of the modified hyaluronic acid of the present invention. A preferred process for producing cross-linked hyaluronic acid gel particles using the modified hyaluronic acid of the present invention comprises the steps of:

(a) preparing a dilute solution containing the water-soluble modified hyaluronic acid of the present invention;

(b) dispersing the above solution into particulate droplets; and (c) conducting a cross-linking reaction of the above modified hyaluronic acid by concentration of a solution contained in the above droplets. The dilute solution in step (a) of the above production method is a solution that contains a substrate and a reagent necessary for the cross-linking reaction. However, since the solution is highly diluted with a solvent, the reaction does not progress in such a solution, or progression of the reaction is extremely slow therein. The concentration of the dilute solution is not particularly limited, and it is, for example, between 0.1% and 5%, and preferably between 0.2% and 3%. As a solvent used in the present invention, solvents commonly used in the present technical field or a mixture thereof can be used. The type of such a solvent is not particularly limited. Examples of a solvent may include water, DMSO, ethanol, N-methylpyrrolidone, and a supercritical carbonated solution. The cross-linked hyaluronic acid gel particles obtained by this production method are preferably injectable.

The method of dispersing the dilute solution into particulate droplets prepared in step (b) of the aforementioned production method is not particularly limited, as long as it is a method commonly used in the present technical field. Examples of such a method may include: a method of spraying the above dilute solution; and a method of mixing the above dilute solution with another liquid to form an emulsion. The method of spraying the above dilute solution is preferable. Herein, the mean particle size of particulate droplets is not particularly limited. The particulate droplet has a mean particle size of, for example, 0.01 µm to 1.5 mm, and preferably 0.1 µm to 500 µm.

The method of concentrating the solution in step (c) of the aforementioned production method is not particularly limited, as long as it is means for concentrating the solution to a concentration that promotes the cross-linking reaction. In addition, the above concentration includes a state wherein a solvent is completely eliminated, in which the above cross-linking reaction progresses as a solid phase reaction.

The cross-linked hyaluronic acid gel particles of the present invention can be produced by concentrating a solution that contains a modified hyaluronic acid having a cross-linkable functional group to a concentration in which a cross-linking reaction progresses from a diluted state wherein such a cross-linking reaction progresses slowly, so as to conduct cross-linking during concentration. In addition, a solution that contains a modified hyaluronic acid having a cross-linkable functional group and a drug is concentrated to a concentration in which a cross-linking reaction progresses from a diluted state wherein such a cross-linking reaction progresses slowly, so as to generate a cross-linking reaction during concentration. Thus, such a cross-linking reaction and drying are carried out simultaneously, so as to obtain drug-encapsulated particles, wherein the drug has been encapsulated in a hyaluronic acid cross-linked body.

More specifically, the process for producing cross-linked hyaluronic acid gel particles of the present invention is not particularly limited, as long as it is a production method wherein drying of particles by solvent evaporation and a cross-linking reaction are carried out simultaneously. For example, a solution that contains a modified hyaluronic acid having a cross-linkable functional group and a drug is subjected to spray drying using a spray dryer, so as to cross-link a modified hyaluronic acid during concentration and drying, and so as to encapsulate a drug in a hyaluronic acid cross-linked body, thereby obtaining drug-deposited particles. When spray drying is used, a drying temperature is preferably 100° C. or lower in order to prevent denaturation of a drug.

Thus, hyaluronic acid gel particles, regarding which a dilute solution contains a drug before a cross-linking reaction and the drug is deposited in particles obtained after the cross-linking reaction, can be obtained using the water-soluble modified hyaluronic acid of the present invention as a substrate.

Otherwise, a cross-linkable modified HA (tetrabutylammonium salt) and a drug have previously been dissolved in a polar organic solvent such as DMSO. Thereafter, the polar organic solvent is extracted by addition of a supercritical fluid such as carbon dioxide, and the modified hyaluronic acid is concentrated, so as to generate the cross-linking reaction of the modified hyaluronic acid, thereby obtaining particles. When such a microparticulation method is used, a surfactant such as Tween-20 or Tween-80 is added (approximately 1% to 2%), so as to increase the recovery ratio of particles generated. In the above production method, a solution containing a modified hyaluronic acid before concentration should have a concentration that does not promote a cross-linking reaction. Specifically, the concentration of a modified hyaluronic acid is preferably between 0.1% and 5%.

Moreover, as another process, an aqueous solution that contains a modified hyaluronic acid having a cross-linkable functional group and a drug is emulsified in a liquid having dewaterability (for example, polyethylene glycol having a molecular weight of 400 daltons, etc.), so as to cross-link the hyaluronic acid during dehydration and concentration, and thus to encapsulate the drug in a hyaluronic acid cross-linked body, thereby obtaining drug-deposited particles. When this process is applied, in order to increase an encapsulation ratio, a cationic or nonionic drug is preferably used.

Furthermore, it is preferable that particles be subjected to heat treatment after formation of the particles, so as to further decrease the moisture content, and that the cross-linking reaction be completely terminated. In this case, a cross-linking density is enhanced, and extension of a sustained-release period is also anticipated.

Still further, cross-linked hyaluronic acid gel particles can be produced by a production method comprising the steps of:
  (a) cross-linking the modified hyaluronic acid of the present invention, so as to obtain a hyaluronic acid gel;
  (b) drying the obtained hyaluronic acid gel;
  (c) freezing the obtained dry product; and
  (d) crushing the obtained frozen product.

By encapsulating a drug during the cross-linking in step (a) of the above production method, a drug-deposited gel can be obtained. Using the above gel, a drug is encapsulated in a hyaluronic acid cross-linked body, so as to obtain drug-deposited gel particles.

Examples of the drying method in step (b) of the above production method may include through circulation drying, drying by sunlight irradiation, drying in a thermostatic bath, drying under reduced pressure, and circulating hot air drying. Taking into consideration the properties of a drug to be encapsulated in a gel, a drying method is appropriately selected. Wind speed, drying time, temperature, and pressure are appropriately selected within a range in which the hyaluronic acid gel of the present invention is not decomposed or denatured. In the case of drying in a thermostatic bath, the temperature is preferably between 30° C. and 60° C., and more preferably between 30° C. and 45° C. In step (b), the sustained-release property of the hyaluronic acid gel obtained in step (a) can be further enhanced.

The freezing method in step (c) of the above production method is not particularly limited, as long as it is a method capable of freezing the dried hyaluronic acid gel. An example of such a method is a method of allowing the above gel to come into contact with dry ice, liquid nitrogen, liquid oxygen, or liquid helium. In addition, it is also possible to allow the above gel to come into contact with metal cooled with these components. The time necessary for allowing the gel to come into contact with the above components is not particularly limited. It is preferably between 3 and 30 minutes, and more preferably between 10 and 15 minutes.

Examples of the crushing method in step (d) of the above production method may include a crushing method using a pestle and a mortar and a crushing method using a mill. Crushing using a mill is preferable. Examples of a mill crushing device may include: rotating disk crushing devices such as a centrifugal crushing device (Nihonseiki Kaisha Ltd.) or an impact mill (Dalton Co., Ltd.); screen mill crushing devices such as Atomizer (Tokyo Atomizer Seizo), Sample Mill (Tokyo Atomizer Seizo), Bantam Mill (Tokyo Atomizer Seizo), or SK Mill (Tokken Inc.); jet crushing devices such as an ultratrace labo jet mill (A-O Jet Mill; Seishin Enterprise Co., Ltd.); and Linrex Mill that enables crushing at an extremely low temperature (Liquid Gas Co., Ltd.). Of these, SK Mill and Linrex Mill are preferable.

Moreover, the freezing process in step (c) and the crushing process in step (d) may be repeated 2 to 10 times, and preferably 3 to 5 times.

The particle size of the hyaluronic acid gel particles obtained by these process may be optimized depending on intended purpose. In order to make it injectable, normally the particle size is preferably between 0.01 and 150 μm. When the above particles are administered via a percutaneous route, the particle size is preferably between 0.01 and 150 μm. When they are administered via transnasal or transpulmonary route, it is preferably between 0.01 and 5 μm in terms of absorption efficiency. When they are administered via an intravenous injection, it is preferably between approximately 0.01 and 0.2 µm in terms of kinetics in blood.

Furthermore, the water-soluble modified HA of the present invention can be used not only for conjugation to a drug, but it can also be used for surface modification of particulate drug carrier such as a polymer micelle, liposome, or nanoparticle, for the purpose of elongation of the residence time in blood. The term "surface modification" is used herein to mean that the water-soluble modified HA of the present invention is allowed to chemically bind to or is physically adsorbed on the surface of a substance consisting of another synthetic polymer, natural polymer, lipid, metal, ceramic, or a complex thereof, or the thus chemically bound or physically adsorbed water-soluble modified HA of the present invention is further cross-linked, so that the water-soluble modified HA of the present invention or a cross-linked body can be present on the outermost surface of the above substance. Examples may include: a polymer micelle comprising a compound obtained by allowing the water-soluble modified HA of the present invention to bind to a hydrophobic polymer such as PLGA; a liposome obtained by allowing the water-soluble modified HA of the present invention to bind to a phospholipid; a particle obtained by allowing the water-soluble modified HA of the present invention to bind to a hydrophobic molecule and then coating the surface of the hydrophobic particle via a hydrophobic interaction; and a particle drug carrier obtained by coating the surface of the hydrophobic particle and then cross-linking the resultant.

Still further, the hyaluronic acid gel particles of the present invention can also be used as a drug carrier, as with the modified hyaluronic acid of the present invention. Herein, such a drug carrier consisting of the hyaluronic acid gel particles of the present invention means a particulate drug carrier used for the treatment or diagnosis of diseases. The particle size of the above carrier is not particularly limited. It is between 1 nm and 200 µm, for example.

The hyaluronic acid gel particles of the present invention are preferably a drug sustained-release carrier.

Since the sustained-release property of a drug to be deposited largely depends on the cross-link density of the cross-linked water-soluble modified hyaluronic acid of the present invention, the sustained-release property of the drug can be regulated by controlling a carboxy group modification ratio.

Still further, the water-soluble modified HA of the present invention and an HA gel obtained by cross-linking the above modified product can be used as components of a medical device, such as an adhesion-preventing agent used after surgical operations. The medical device in the present invention is not particularly limited, as long as it is used for the treatment or diagnosis of diseases, or as assistance therefor. Examples of such a medical device may include an artificial organ, an implant, a catheter, a drug-encapsulating gel, and a drug-encapsulating pellet.

A specific example of the aforementioned medical device is a medical device, the surface of which is modified with the water-soluble modified HA of the present invention.

Examples of a drug allowed to bind to the modified hyaluronic acid of the present invention and a drug encapsulated in the hyaluronic acid gel of the present invention (a low-molecular-weight compound, a protein, a peptide, and nucleic acid) may include the following substances.

Examples of a low-molecular-weight compound may include: anticancer agents (e.g. an alkylating agent, an antimetabolite, an alkaloid, etc.); immunosuppressive agents; anti-inflammatory agents (e.g. a steroid drug, a nonsteroidal anti-inflammatory drug, etc.); antirheumatic drugs; and antibacterial agents (e.g. a β-lactam antibiotic, an aminoglycoside antibiotic, a macrolide antibiotic, a tetracycline antibiotic, a new quinolone antibiotic, a sulfa drug, etc.).

Examples of a protein or peptide may include erythropoietin (EPO), a granulocyte colony-stimulating factor (G-CSF), interferon-α, β, and γ (INF-α, β, and γ), thrombopoietin (TPO), a ciliary neurotrophic factor (CNTF), a tumor necrosis factor (TNF), a tumor necrosis factor-binding protein (TNFbp), interleukin-10 (IL-10), FMS-like tyrosine kinase (Flt-3), growth hormone (GH), insulin, insulin-like growth factor-1 (IGF-1), a platelet-derived growth factor (PDGF), an interleukin-1-receptor antagonist (IL-Ira), a brain-derived neurotrophic factor (BDNF), a keratinocyte growth factor (KGF), a stem cell factor (SCF), a megakaryocyte growth and development factor (MGDF), osteoprotegerin (OPG), leptin, parathyroid hormone (PTH), a basic fibroblastic growth factor (b-FGF), a bone morphogenetic protein (BMP), an atrial natriuretic peptide (ANP), a brain natriuretic peptide (BNP), a C-type natriuretic peptide (CNP), a glucagon-like peptide-1 (hereinafter also referred to as "GLP-1"), an antibody, a diabody, a minibody, and a fragmented body.

Examples of nucleic acid may include DNA, RNA, antisense, decoy, ribozyme, and small interfering RNA.

In addition, a drug to be encapsulated in the hyaluronic acid gel of the present invention is preferably a conjugate consisting of the aforementioned drug and a polymer. The type of a polymer used in this case is not particularly limited. Examples of such a polymer may include PEG, HA, a modified HA, dextran, pullulan, polyglutamate, and polysialic acid.

The water-soluble modified HA, hyaluronic acid gel, and hyaluronic acid gel particle of the present invention can be administered in the form of a conjugate with a drug, or in the form of a pharmaceutical composition, which encapsulates a drug therein and comprises one or more pharmacologically acceptable agents such as a diluent, a wetting agent, an emulsifying agent, a dispersing agent, an adjuvant, an antiseptic, a buffer, a binder, or a stabilizer, depending on an administration route of interest, in the form of a suitable, any given form. Such an administration route may be either a parenteral route, or an oral route.

The present invention enables production of the water-soluble modified HA, the residence time in blood of which is elongated to a practical level, which cannot be achieved by the conventional process. In addition, by conjugating a drug using the water-soluble modified HA of the present invention as a carrier, it becomes possible to provide a practical and safe pharmaceutical composition, which could not achieved by the prior art techniques.

Moreover, using the water-soluble modified HA of the present invention, it becomes possible to provide a hyaluronic acid gel sustained-release agent and a pharmaceutical composition, which are highly safe and enable a long-term sustained-release of drug, and which encapsulate a protein, a peptide, nucleic acid, a low-molecular-weight compound, or a conjugate comprising these components and a polymer, which cannot be obtained by the conventional modified HA.

EXAMPLES

Preferred examples of the present invention will be described more in detail below. However, these examples are not intended to limit the scope of the present invention.

NMR measurement was carried out using a nuclear magnetic resonance apparatus JNM-ECA500 (manufactured by JEOL Ltd.). Measurement conditions for $^1$H-NMR are as follows:

NMR Measurement Conditions
Data point: 16384
Spectral width (X sweep): 15 ppm
Acquisition time (X acq time): 1.749 s
Pulse delay (Relaxation delay): 30 s
Transients (Scans): 64
Temperature: room temperature
Measurement solvent: $D_2O$ Moreover, the HA unit described below means a repeating unit (1 unit) of N-acetylglucosamine-glucuronic acid in hyaluronic acid.

Example 1

Synthesis of Modified Hyaluronic Acid in Aprotic Polar Solvent (Condensing Agent, Solvent Mixing Ratio, Enzymatic Degradability)

Various synthetic conditions were studied in an aprotic polar solvent, and modified hyaluronic acids obtained under individual conditions were then evaluated in terms of enzyme resistance.

Example 1-1

DOWEX 50WX8-400 (manufactured by Sigma-Aldrich), which had been converted to tetrabutylammonium (TBA) salts using tetrabutyl hydroxide (manufactured by Sigma-Aldrich), were used to convert hyaluronic acid sodium salt having a molecular weight of 200 kDa (HA: manufactured by Denki Kagaku Kogyo Kabushiki Kaisha) to TBA salts. Thereafter, 29.1 mg of the obtained hyaluronic acid tetrabutylammonium salt (hereinafter also referred to as "HA-TBA") was dissolved in DMSO (manufactured by Wako Pure Chemical Industries, Ltd.), resulting in a concentration of 2.0 mg/ml. Based on an equivalent ratio of HA unit/BOP (manufactured by Wako Pure Chemical Industries, Ltd.)/ethylenediamine (hereinafter also referred to as "EDA": manufactured by Sigma-Aldrich)=1/2.5/100 (mol/mol/mol), EDA and BOP were added in this order to the solution, and the mixture was reacted at room temperature overnight. Thereafter, 10 ml of a 1 M NaCl aqueous solution was added to the reaction solution, and 5N HCl solution was then added thereto, so as to decrease pH to 3. Furthermore, the resultant was neutralized with 2N NaOH solution. Thereafter, the resultant was dialyzed against large excess amount of distilled water (Milli Q water) for purification (Spectrapore 4; molecular weight cut off (hereinafter also referred to as "MWCO"): 12 k-14 kDa), followed by ultrafiltration (YM-10; manufactured by MILLIPORE). Thereafter, the resultant was freeze-dried, so as to obtain 25.8 mg of the captioned hyaluronic acid into which an amino group had been introduced (hereinafter also referred to as "HA-AM").

Example 1-2

The same method as that described in Example 1-1 was applied with the exceptions that 2,2'-(ethylenedioxy)bis(ethylamine) (hereinafter also referred to as "EDOBEA"; manufactured by Sigma-Aldrich) was used instead of ethylenediamine, and that using 35.1 mg of HA-TBA, the reaction was carried out at an equivalent ratio of HA unit/BOP/EDOBEA=1/2.5/50 (mol/mol/mol), so as to obtain 27.2 mg of hyaluronic acid into which an amino group had been introduced (HA-AM).

Example 1-3

The same method as that described in Example 1-2 was applied with the exceptions that hexamethylenediamine (HMDA; manufactured by Sigma-Aldrich) was used instead of EDOBEA, and that 62.0 mg of HA-TBA was used, so as to obtain 41.1 mg of hyaluronic acid into which an amino group had been introduced (HA-AM).

Example 1-4

The same method as that described in Example 1-2 was applied with the exceptions that PyBOP (manufactured by Kokusan Chemical Co., Ltd.) was used instead of BOP, and that 51.8 mg of HA-TBA was used, so as to obtain 39.0 mg of hyaluronic acid into which an amino group had been introduced (HA-AM).

Comparative Example 1-1

Water was used instead of DMSO. EDC (manufactured by Sigma-Aldrich) was used instead of BOP. 50.0 mg of HA (sodium salts) was used in a concentration of 1.0 mg/ml, and HA unit/EDC/ethylenediamine.2HCl (hereinafter also referred to as "EDA.2HCl"; manufactured by Wako Pure Chemical, Ltd.) was set to an equivalent ratio of 1/4/100 (mol/mol/mol). The pH was adjusted to be 7.0, and the reaction was carried out overnight. The same method as that described in Example 1-1 was applied with the aforementioned exceptions, so as to obtain 36.1 mg of hyaluronic acid into which an amino group had been introduced (HA-AM).

Comparative Example 1-2

The same method as that described in Comparative Example 1-1 was applied with the exception that water/ethanol (90/10) was used instead of DMSO, so as to obtain 36.0 mg of hyaluronic acid into which an amino group had been introduced (HA-AM).

Comparative Example 1-3

The same method as that described in Comparative Example 1-1 was applied with the exception that water/ethanol (70/30) was used instead of DMSO, so as to obtain 38.3 mg of hyaluronic acid into which an amino group had been introduced (HA-AM).

Comparative Example 1-4

The same method as that described in Comparative Example 1-3 was applied with the exceptions that EDC/HODhbt (manufactured by Watanabe Chemical Industries, Ltd.) was used instead of EDC, and that HA unit/EDC/HODhbt/EDA.2HCl was set to an equivalent ratio of 1/4/4/100 (mol/mol/mol/mol), so as to obtain 49.3 mg of hyaluronic acid into which an amino group had been introduced (HA-AM).

Comparative Example 1-5

The same method as that described in Comparative Example 1-1 was applied with the exceptions that water/DMSO (60/40) was used instead of DMSO, and that HA unit/EDC/EDA.2HCl was set to an equivalent ratio of 1/2/50 (mol/mol/mol), so as to obtain 44.0 mg of hyaluronic acid into which an amino group had been introduced (HA-AM).

Comparative Example 1-6

The same method as that described in Comparative Example 1-5 was applied with the exception that BOP was used instead of EDC, so as to obtain 42.1 mg of hyaluronic acid into which an amino group had been introduced (HA-AM).

Comparative Example 1-7

The same method as that described in Comparative Example 1-1 was applied with the exception that hexamethylenediamine.2HCl (HMDA.2HCl; manufactured by Tokyo Chemical Industry, Co. Ltd.) was used instead of EDA.2HCl, so as to obtain 35.2 mg of hyaluronic acid into which an amino group had been introduced (HA-AM).

Comparative Example 1-8

The same method as that described in Comparative Example 1-3 was applied with the exception that HMDA.2HCl was used instead of EDA.2HCl, so as to obtain 33.3 mg of hyaluronic acid into which an amino group had been introduced (HA-AM).

Comparative Example 1-9

The same method as that described in Comparative Example 1-3 was applied with the exceptions that HMDA.2HCl was used instead of EDA.2HCl, and that water/ethanol (60/40) was used, so as to obtain 33.6 mg of hyaluronic acid into which an amino group had been introduced (HA-AM).

Comparative Example 1-10

The same method as that described in Comparative Example 1-4 was applied with the exceptions that HMDA.2HCl was used instead of EDA.2HCl, and that water/ethanol (60/40) was used, so as to obtain 48.4 mg of hyaluronic acid into which an amino group had been introduced (HA-AM).

Comparative Example 1-11

The same method as that described in Comparative Example 1-5 was applied with the exceptions that water/DMSO (50/50) was used instead of water/DMSO (60/40), and that 51.9 mg of HA was used, so as to obtain 47.5 mg of hyaluronic acid into which an amino group had been introduced (HA-AM).

Comparative Example 1-12

The same method as that described in Example 1-2 was applied with the exceptions that DCC (Wako Pure Chemical Industries. Ltd.) was used instead of BOP, that 69.9 mg of HA-TBA was used in a concentration of 4.0 mg/ml, and that HA unit/DCC/EDOBEA was set to an equivalent ratio of 1/4/100 (mol/mol/mol), so as to obtain 54.5 mg of hyaluronic acid into which an amino group had been introduced (HA-AM).

Comparative Example 1-13

The same method as that described in Example 1-1 was applied with the exceptions that DCC was used instead of BOP, and that 54.1 mg of HA-TBA was used, so as to obtain 40.7 mg of hyaluronic acid into which an amino group had been introduced (HA-AM).

Comparative Example 1-14

The same method as that described in Example 1-1 was applied with the exceptions that CDI (manufactured by Sigma-Aldrich) was used instead of BOP, and that 50.0 mg of HA-TBA was used, so as to obtain 31.6 mg of hyaluronic acid into which an amino group had been introduced (HA-AM).

Comparative Example 1-15

The same method as that described in Example 1-2 was applied with the exceptions that EDC was used instead of BOP, and that 46.4 mg of HA-TBA was used, so as to obtain 30.4 mg of hyaluronic acid into which an amino group had been introduced (HA-AM).

Comparative Example 1-16

The same method as that described in Example 1-2 was applied with the exceptions that EEDQ (manufactured by Wako Pure Chemical Industries, Ltd.) was used instead of BOP, and that 58.4 mg of HA-TBA was used, so as to obtain 39.5 mg of hyaluronic acid into which an amino group had been introduced (HA-AM).

Comparative Example 1-17

The same method as that described in Example 1-2 was applied with the exceptions that DMT-MM (manufactured by Wako Pure Chemical Industries, Ltd.) was used instead of EEDQ, and that 53.5 mg of HA-TBA was used, so as to obtain 33.2 mg of hyaluronic acid into which an amino group had been introduced (HA-AM).

Comparative Example 1-18

The same method as that described in Example 1-2 was applied with the exceptions that TBTU (manufactured by Wako Pure Chemical Industries, Ltd.) was used instead of DMT-MM, and that 56.0 mg of HA-TBA was used, so as to obtain 30.0 mg of hyaluronic acid into which an amino group had been introduced (HA-AM).

Test Example 1

Evaluation of Enzymatic Degradability

Each of HA-AM obtained in Examples 1-1 to 1-4 and Comparative Examples 1-1 to 1-18 was dissolved in distilled water (Milli Q water), resulting in a concentration of 2 mg/ml. Thereafter, 132 µl of a 0.2 M phosphate buffer (pH 6.2) and 77 µl of water were added to 55 µl of the obtained solution. Thereafter, 44 µl of 1 U/ml hyaluronidase SD (manufactured by Seikagaku Corporation) solution (0.05 M phosphate buffer containing 0.01% BSA (pH 6.2)) was then added thereto, and the obtained mixture was incubated at 37° C. for 24 hours. 100 µl of each sample was fractionated, and 720 µl of a 50 mM acetic acid solution was then added thereto, so as to terminate the reaction. As a control, a no enzyme addition group was subjected to the same above operations (data is omitted). Each sample was subjected to gel permeation chromatography (hereinafter also referred to as "GPC"), and a change in the molecular weight of HA-AM and a pattern of generation of a decomposition product were observed (absorption at 232 nm). Conditions for GPC are described below.

GPC Measurement Conditions
GPC column: Superdex200 10/300 GL, Superdex 75HR 10/30, Superdex Peptide HR 10/30 (manufactured by Amersham Biosciences) (3 columns connected)
Eluent: PBS (pH 7.4)
Flow Ratio: 0.4 ml/min Furthermore, in the present test example, resistance to digestion by hyaluronidase was not obtained, also when two conditions, namely, (a) a single use of DMSO as a solvent and (b) the use of BOP or PyBOP as a condensing agent, were not satisfied. Thus, it became clear that these conditions are unsuitable for introduction of an amino compound into HA.

TABLE 1

Synthetic results

| Substituent | Solvent | Condensing agent | Organic solvent % | HA concentration | Hydase SD assay | HA:Condensing agent | HA:Substituent | |
|---|---|---|---|---|---|---|---|---|
| EDA 2HCl | H$_2$O | EDC | 0% | 1 mg/mL | x | 1:4 | 1:100 | Com. Ex. 1-1 |
| | H$_2$O/EtOH | EDC | 10% | 1 mg/mL | x | 1:4 | 1:100 | Com. Ex. 1-2 |
| | H$_2$O/EtOH | EDC | 30% | 1 mg/mL | x | 1:4 | 1:100 | Com. Ex. 1-3 |
| | H$_2$O/EtOH | EDC/HODhbt | 30% | 1 mg/mL | x | 1:4:4 | 1:100 | Com. Ex. 1-4 |
| | H$_2$O/DMSO | EDC | 40% | 1 mg/mL | x | 1:2 | 1:50 | Com. Ex. 1-5 |
| | H$_2$O/DMSO | BOP | 40% | 1 mg/mL | x | 1:2 | 1:50 | Com. Ex. 1-6 |
| EDA | DMSO | DCC | — | 2 mg/mL | x | 1:2.5 | 1:100 | Com. Ex. 1-13 |
| | DMSO | CDI | — | 2 mg/mL | x | 1:1.2 | 1:50 | Com. Ex. 1-14 |
| | DMSO | BOP | — | 2 mg/mL | ○ | 1:2.5 | 1:100 | Ex. 1-1 |
| | DMSO | EDC | — | 2 mg/mL | x | 1:2.5 | 1:50 | Com. Ex. 1-15 |
| EDA | DMSO | EEDQ | — | 2 mg/mL | x | 1:2.5 | 1:50 | Com. Ex. 1-16 |
| | DMSO | DMT-MM | — | 2 mg/mL | x | 1:2.5 | 1:50 | Com. Ex. 1-17 |
| | DMSO | TUTB | — | 2 mg/mL | x | 1:2.5 | 1:50 | Com. Ex. 1-18 |
| | DMSO | PyBOP | — | 2 mg/mL | ○ | 1:2.5 | 1:50 | Ex. 1-4 |
| HMDA 2HCl | H$_2$O | EDC | 0% | 1 mg/mL | x | 1:4 | 1:100 | Com. Ex. 1-7 |
| | H$_2$O/EtOH | EDC | 30% | 1 mg/mL | x | 1:4 | 1:100 | Com. Ex. 1-8 |
| | H$_2$O/EtOH | EDC | 40% | 1 mg/mL | x | 1:4 | 1:100 | Com. Ex. 1-9 |
| | H$_2$O/EtOH | EDC/HODhbt | 40% | 1 mg/mL | x | 1:4:4 | 1:100 | Com. Ex. 1-10 |
| | H$_2$O/DMSO | EDC | 50% | 1 mg/mL | x | 1:2 | 1:50 | Com. Ex. 1-11 |
| HMDA | DMSO | BOP | — | 2 mg/mL | ○ | 1:2.5 | 1:50 | Ex. 1-3 |
| EDOBEA | DMSO | BOP | — | 2 mg/mL | ○ | 1:2.5 | 1:50 | Ex. 1-2 |
| | DMSO | DCC | — | 4 mg/mL | x | 1:4 | 1:100 | Com. Ex. 1-12 |

Figure 2:
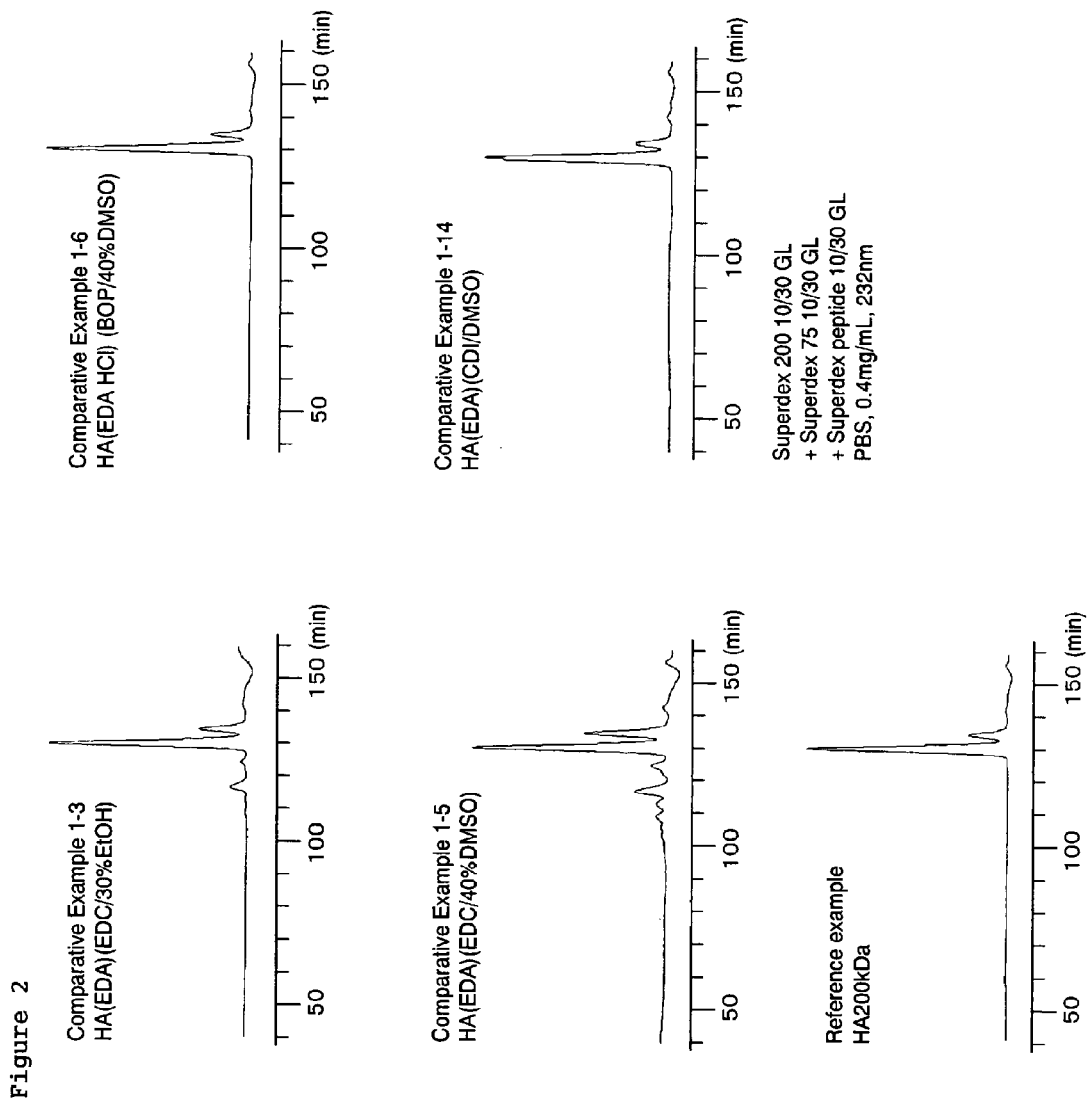
FIG. 2 shows an example of GPC charts obtained after treating the water-soluble modified hyaluronic acid and hyaluronic acid of comparative example with hyaluronidase. The scale in the longitudinal axis direction is the same as that of FIG. 1.

Injection Volume: 50 μl
Detection: UV (232 nm)
HA-AM wherein a disaccharide decomposition peak (Retention time: 130 minutes) was observed was evaluated as x, and HA-AM wherein such a peak was not observed was evaluated as ○. Such results are shown in Table 1. In addition, typical GPC charts are shown in FIGS. 1 and 2 (Examples 1-1 to 1-4, Comparative Examples 1-3, 1-5, 1-6, and 1-14, and Reference example).

Figure 3:
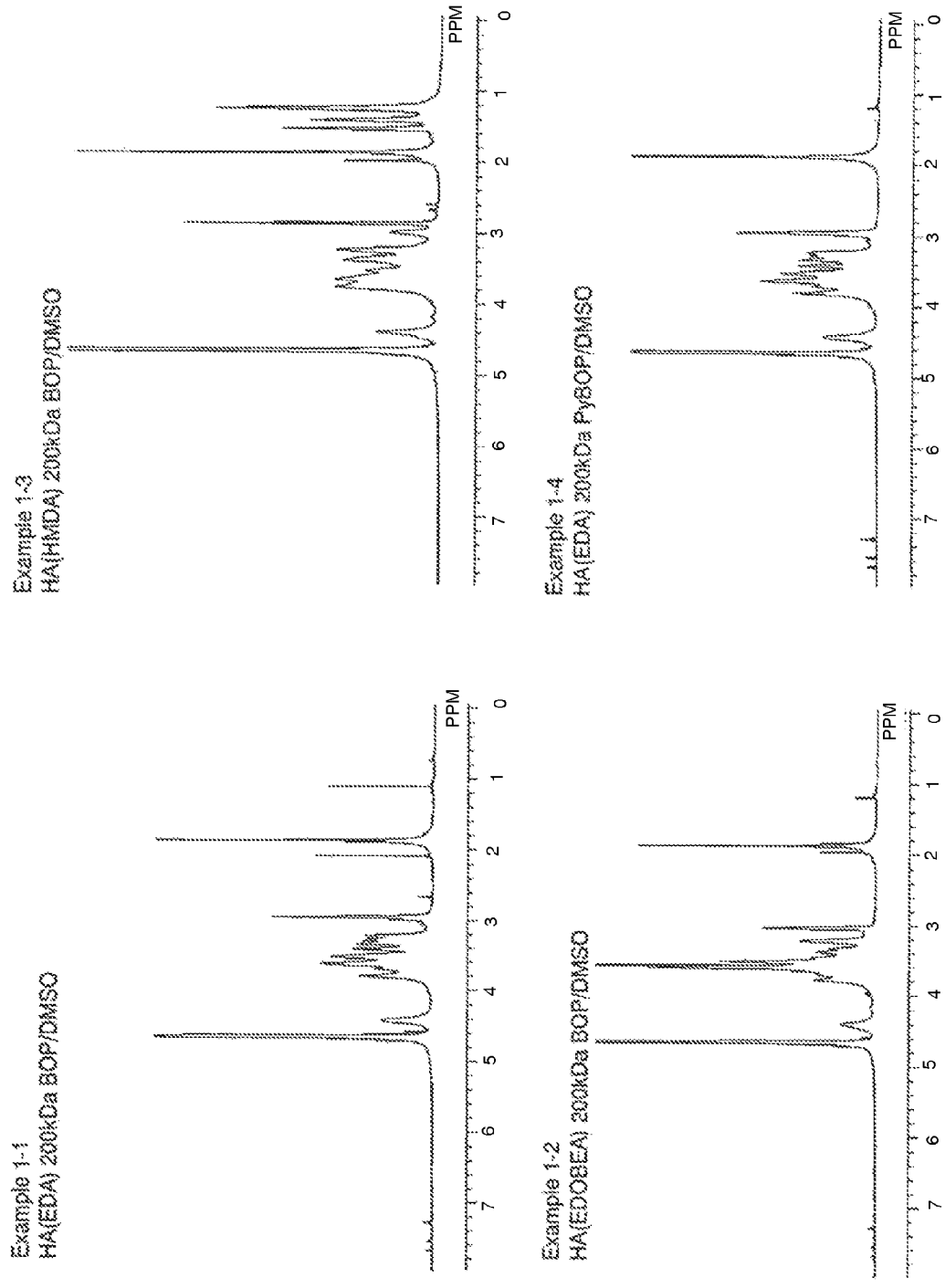
FIG. 3 shows an example of the $^1$H-NMR spectra of the water-soluble modified hyaluronic acid of the present invention.

Moreover, the amino group introduction ratio of HA of each of Examples 1-1 to 1-4 was quantified by the $^1$H-NMR method (HA: methyl proton of N-acetyl group, 1.8 to 1.9 ppm; AM: methylene proton of ethylenediamine portion, 2.9 to 3.1 ppm). $^1$H-NMR spectra are shown in FIG. 3. The amino group introduction rates are 97.5%, 75.5%, 88.3%, and 84.5%, respectively.

Figure 4:
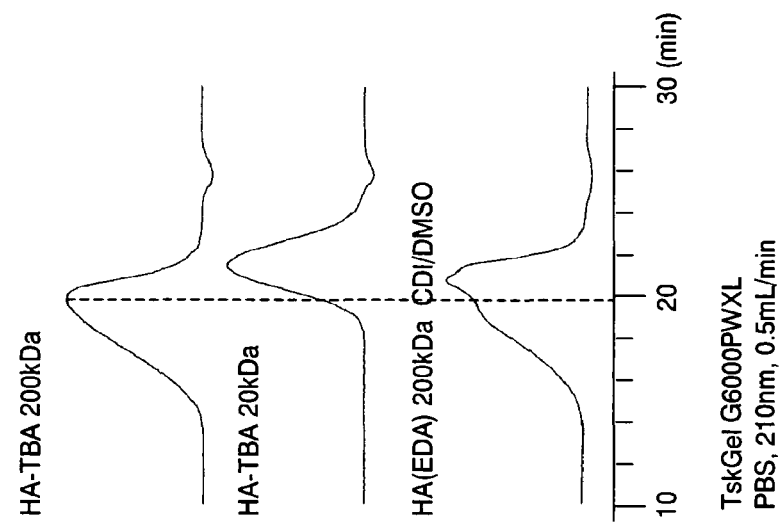
FIG. 4 shows an example of GPC charts obtained before and after the reaction in the case of introduction using CDI (Comparative Example 1-14)

A gel permeation chromatogram obtained before and after an introduction reaction using CDI (Comparative Example 1-14) is shown in FIG. 4. In addition, GPC conditions are described below.

GPC Measurement Conditions
GPC column: TSKgel G6000PW$_{XL}$ (manufactured by TOSOH)
Eluent: PBS (pH 7.4)
Flow Ratio: 0.5 ml/min
Injection Volume: 50 μl
Detection: UV (210 nm)

When CDI was used as a condensing agent, a clear decomposition was observed. Thus, it was confirmed that the molecular weight of HA was significantly decreased in condensation using CDI. Moreover, since resistance to digestion by hyaluronidase was not obtained, it became clear that the use of CDI as a condensing agent is unsuitable for introduction of an amino compound into HA.

Example 2

Control of Introduction Ratio of Diamine Compound Due to Addition Ratio of BOP

In order to control the introduction ratio of a diamine compound, a condensing agent was added at various rates, so as to evaluate enzyme resistance.

Three solutions were prepared by dissolving 2.0 mg/ml HA (200 kDa)-TBA in DMSO. EDA was added to each solution at an equivalent ratio of HA unit/ethylenediamine (EDA)=1/50 (mol/mol). A BOP reagent was added at an equivalent ratio of 1.08, 1.5, or 2.0 to the HA unit, respectively, and the obtained mixture was then reacted overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against large excess amount of distilled water (Milli Q water) for purification (Spectrapore 4; molecular weight cut off (MWCO): 12 k-14 kDa), followed by ultrafiltration (YM-10; manufactured by MILLIPORE). Thereafter, the resultant was freeze-dried.

Moreover, three solutions were prepared by dissolving 2.0 mg/ml HA (23 kDa)-TBA in DMSO. EDOBEA was added to each solution at an equivalent ratio of HA unit/2,2'-(ethylenedioxy)bis(ethylamine) (EDOBEA)=1/50 (mol/mol). A BOP reagent was added at an equivalent ratio of 1.0, 1.5, or 2.0 to the HA unit, and the obtained mixture was then reacted overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against large excess amount of distilled water (Milli Q water) for purification (Spectrapore 4; molecular weight cut off (MWCO): 12 k-14 kDa), followed by ultrafiltration (YM-10; manufactured by MILLIPORE). Thereafter, the resultant was freeze-dried.

Figure 5:
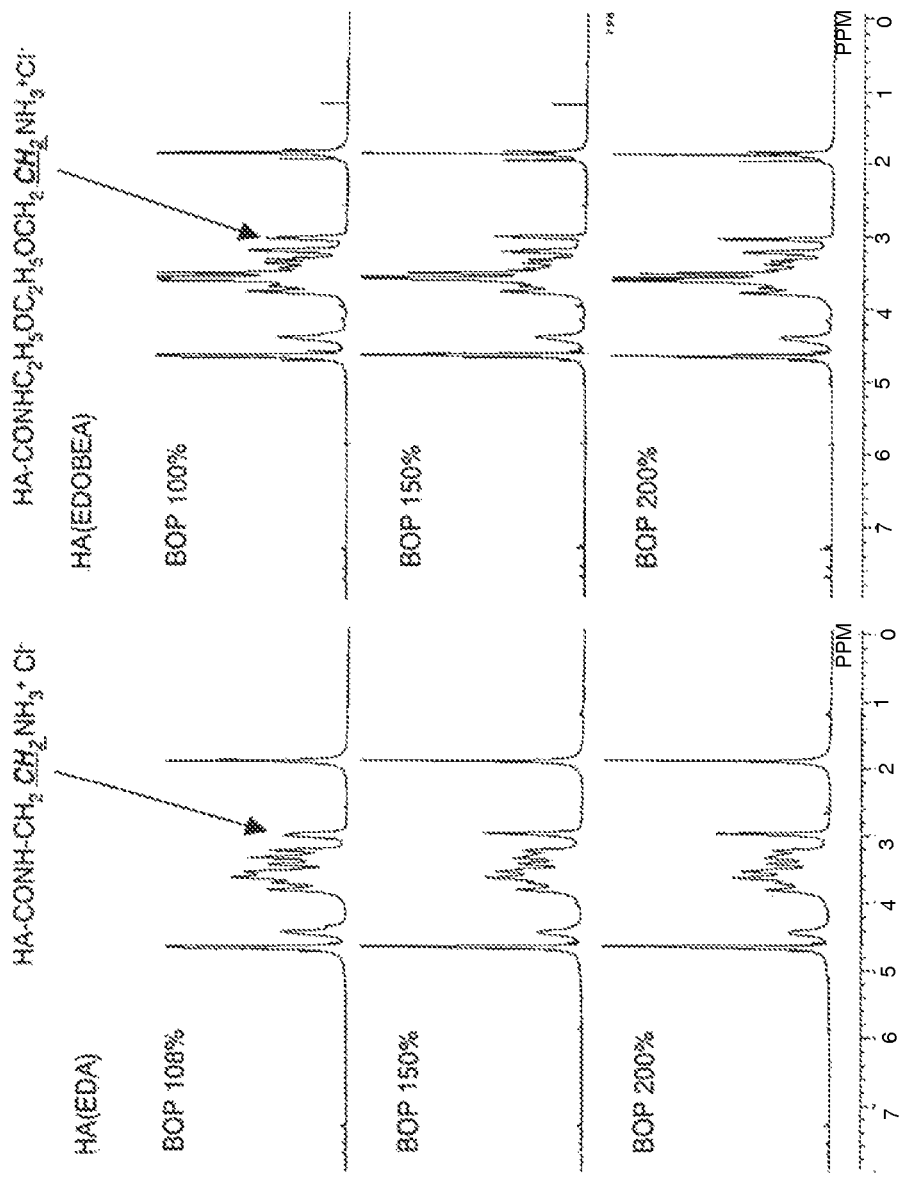
FIG. 5 shows an example of the $^1$H-NMR spectra regarding the control of the introduction ratio of a diamine compound due to the additive amount of BOP (Example 2)

The amino group introduction ratio of Example 2 was quantified by the $^1$H-NMR method (HA: methyl proton of N-acetyl group, 1.8 to 1.9 ppm; AM: methyl proton of EDA portion, 2.9 to 3.1 ppm; and methylene proton of EDOBEA portion, 2.9 to 3.1 ppm). $^1$H-NMR spectra are shown in FIG. 5. In addition, the hyaluronidase resistance of each modified HA was evaluated by the same method as that in Test Example 1. The results regarding the amino group introduction ratio and the hyaluronidase resistance evaluation are shown in Table 2. It was revealed that the amino group introduction ratio can be controlled by addition of BOP, and that using a BOP reagent as a condensing agent in an aprotic polar organic solvent, it becomes possible to uniformly introduce amino groups at a high introduction ratio.

TABLE 2

Amino group introduction ratio and hyaluronidase resistance evaluation

| Substituent | HA molecular weight | Reaction time | Hydase SD assay | HA:condensing agent | Introduction ratio (%) (NMR) |
|---|---|---|---|---|---|
| EDA | 200 kDa | overnight | ○ | 100:107.8 | 68.0 |
| | 200 kDa | overnight | ○ | 100:150 | 84.5 |
| | 200 kDa | overnight | ○ | 100:200 | 88.0 |
| EDOBEA | 23 kDa | 9 h | ○ | 100:100 | 58.0 |
| | 23 kDa | 9 h | ○ | 100:150 | 69.0 |
| | 23 kDa | 9 h | ○ | 100:200 | 71.0 |

It has been known that HA forms an intramolecular hydrogen bond, and the secondary and tertiary structures as a result of intramolecular and intermolecular hydrophobic interactions, in water (The Biology of Hyaluronan. Chiba Foundation Symposium, Vol. 143, pp. 6-14 (1989)). Thus, it is considered that uniform chemical modification becomes difficult. Accordingly, even though many carboxy groups of HA are modified in water, a portion of an unmodified domain consisting of contiguous tetrasaccharide to hexasaccharide, which can be recognized by an HA receptor, remains. It is predicted that such a domain binds to the HA receptor in a body, so that it is cleared from the blood in a relatively short time.

The hydrogen bond of HA and hydrophobic interaction are attenuated in an aprotic polar solvent, so that the higher structure of HA is destroyed, so that unevenness of the environment around carboxy groups due to formation of a higher structure is solved, and so that more uniform chemical modification can be achieved, thereby obtaining enzyme resistance.

Example 3

Evaluation of Hyaluronidase Resistance of Modified HA Involving Carboxylic Acid Conversion In order to evaluate enzyme resistance more in detail, a modified HA (HA-AM-SUC) wherein the introduced primary amine had been converted to carboxylic acid was synthesized. The enzyme resistance of the obtained modified HA was evaluated.

Example 3-1

Synthesis of HA-AM

Six solutions were prepared by dissolving 4.0 mg/ml HA (200 kDa)-TBA in DMSO. Thereafter, 2,2'-(ethylenedioxy)bis(ethylamine) (EDOBEA) was added to each solution at an equivalent ratio of HA unit/EDOBEA=1/50 (mol/mol). A BOP reagent was added at an equivalent ratio of 0.4, 0.6, 1.0, 1.5, 1.85, or 2.5 to the HA unit, and the obtained mixture was then reacted overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against a 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying, so as to obtain an EDOBEA-introduced modified HA.

Example 3-2

Conversion of Primary Amine to Carboxylic Acid

Figure 6:
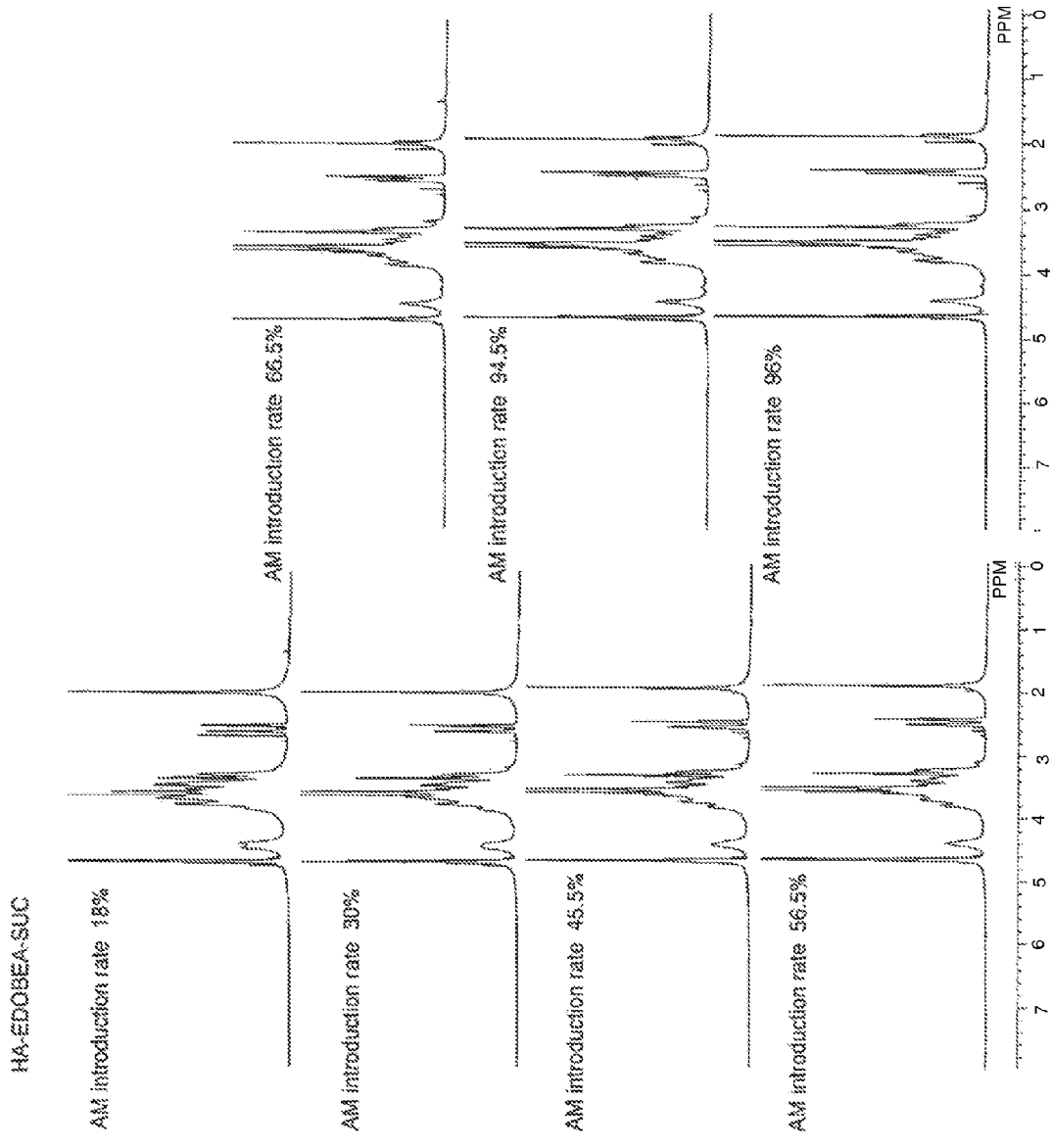
FIG. 6 shows an example of the $^1$H-NMR spectra of a water-soluble modified hyaluronic acid obtained by converting the amino group of the water-soluble modified hyaluronic acid of the present invention and introducing a carboxy group therein (Example 3-2)

Distilled water (Milli Q water) was added to the sample as obtained above (Example 3-1) to prepare a solution having a concentration of 20.0 mg/ml. Thereafter, a 0.2 M carbonate buffer (pH 9.0) was added to the prepared solution, resulting in a concentration of 10.0 mg/ml. Thereafter, succinic anhydride (manufactured by Wako Pure Chemical Industries, Ltd.) that was 20 mole times to an HA unit (1 unit=a repeating unit, N-acetylglucosamine-glucuronic acid) was dissolved in DMSO that was 1/10 the volume of an HA-AM solution. The DMSO solution was then added to the above HA-AM solution, and the obtained mixture was then stirred at room temperature for 30 minutes. Thereafter, the resultant was dialyzed against a 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying, so as to obtain HA-AM-SUC. The NMR spectra are shown in FIG. 6. The peak of methylene (2.9 to 3.1) adjacent to an amino group completely disappeared, and a peak derived from succinic acid was newly observed (2.4 to 2.6 ppm). Thus, it was revealed that the amino groups were converted to carboxy groups.

Example 3-3

Evaluation of Enzymatic Degradability

Figure 7:
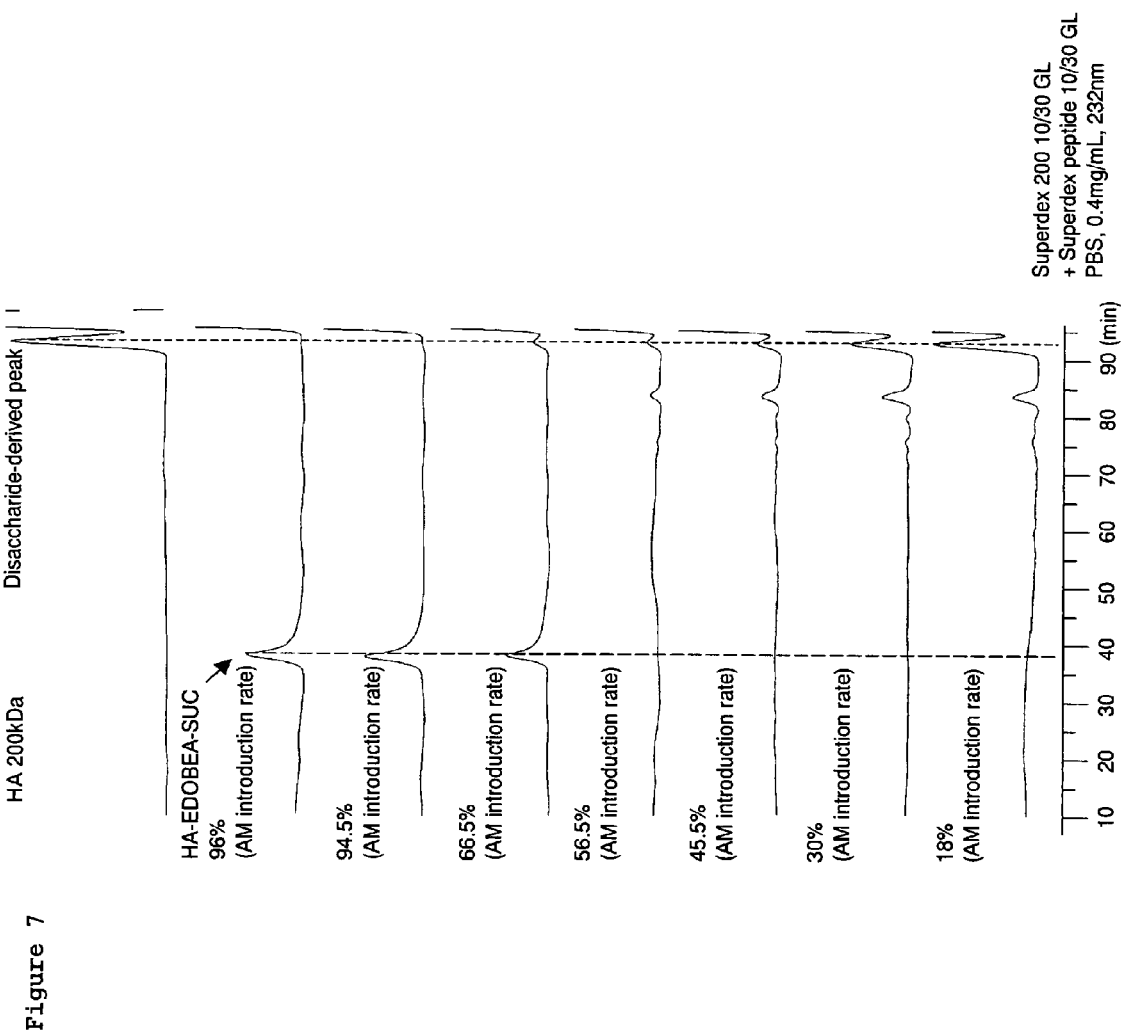
FIG. 7 shows an example of GPC charts obtained after treating with hyaluronidase of a water-soluble modified hyaluronic acid obtained by converting the amino group of the water-soluble modified hyaluronic acid of the present invention and introducing a carboxy group therein.

HA-AM-SUC obtained in Example 3-2 was dissolved in distilled water (Milli Q water), resulting in a concentration of 4 mg/ml. Thereafter, 200l of a 0.1 M phosphate buffer (pH 6.2) and 25 µl of water were added to 25 µl of the obtained solution. Thereafter, 50 µl of 1 U/ml hyaluronidase SD (Seikagaku Corporation) solution (0.2 M phosphate buffer, pH 6.2) was then added thereto, and the obtained mixture was incubated at 37° C. for 24 hours. 100 µl of each sample was fractionated, and 700 µl of a 50 mM acetic acid solution was then added thereto, so as to terminate the reaction. As a control, a no-enzyme-addition group was subjected to the same above operations (data is omitted). Each sample was subjected to gel permeation chromatography (hereinafter also referred to as "GPC"), and a change in the molecular weight of HA-AM-SUC and a pattern of generation of a decomposition product were observed (absorption at 232 nm). The results are shown in FIG. 7 and Table 3. In addition, conditions for GPC are described below.

GPC Measurement Conditions

GPC column: Superdex200 10/300 GL, Superdex PeptideHR 10/30 (manufactured by Amersham Biosciences) (2 columns connected)

Eluent: PBS (pH 7.4)

Flow Ratio: 0.4 ml/min

Injection Volume: 50 µl

Detection: UV (232 nm)

TABLE 3

Correlation between amino group modification ratio and hyaluronidase resistance

| Introduction ratio | Ratio of peak area of disaccharide to entire peak area (%) |
| --- | --- |
| 18.0 | 88.9 |
| 30.0 | 52.5 |
| 45.5 | 22.5 |
| 56.5 | 11.9 |
| 66.5 | 12.9 |
| 94.5 | 0.0 |
| 96.0 | 0.0 |

Herein, the percentage of disaccharide in the decomposition product was calculated based on the formula 100×(peak area of disaccharide)/(the entire peak area–the entire peak area during no addition of enzyme), within a range in which a peak derived from a solvent was excluded (Retention Time: 90 minutes). With regard to enzyme resistance, it was revealed that enzyme resistance is enhanced in response to the introduction ratio of amine, that is, the modification ratio of carboxylic acid of HA.

Example 4

Synthesis of Modified HA into which Various Functional Groups have been Introduced, and Control of Introduction Ratio of Functional Groups by Two Components Introduction of various functional groups was studied. In addition, in order to maintain a long-term retention ability in blood and to control the introduction ratio of reactive functional groups, two compounds were introduced.

Example 4-1

Synthesis of Hydroxyl Group-Introduced Modified HA (HA-OH)

Example 4-1-1

Synthesis of Aminoethanol (AEtOH)-Introduced Modified HA

Figure 8:
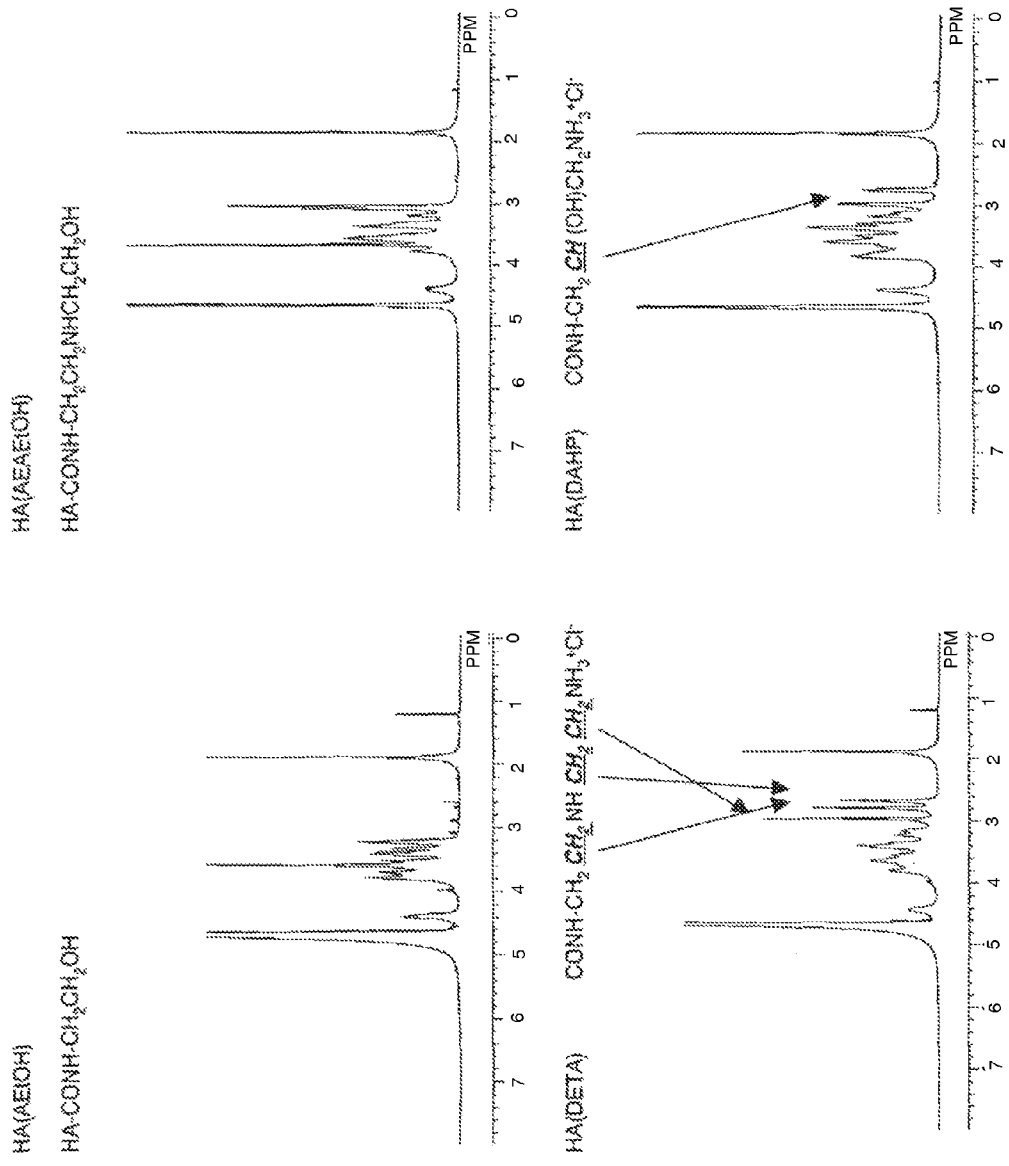
FIG. 8 shows an example of the $^1$H-NMR spectra of the water-soluble modified hyaluronic acid of the present invention.

HA (200 kDa)-TBA was dissolved in DMSO, so as to prepare a 5.0 mg/ml solution. Thereafter, aminoethanol (hereinafter also referred to as "AEtOH"; manufactured by Sigma-Aldrich) was added thereto at an equivalent ratio of HA unit/primary amine=1/50 (mol/mol). Thereafter, a BOP reagent was further added at an equivalent ratio of 2.5 to the HA unit, and the obtained mixture was then stirred overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH. Thereafter, the resultant was dialyzed against large excess amount of 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying. The $^1$H-NMR spectrum of the obtained sample is shown in FIG. 8.

Example 4-1-2

Synthesis of Modified HA into which 2-(2-Aminoethylamino)Ethanol (AEAEtOH) has Been Introduced The same method as that described in Example 4-1-1 was applied with the exception that 2-(2-aminoethylamino)ethanol (hereinafter also referred to as AEAEtOH; manufactured by Sigma-Aldrich) was used instead of AEtOH. The $^1$H-NMR spectrum of the obtained sample is shown in FIG. 8.

In the $^1$H-NMR measurement of each of the samples of Examples 4-1-1 and 4-1-2, a new peak was observed, and thus it was confirmed that conversion of interest had been achieved. However, since the peak of the introduced compound overlapped with the peak derived from HA, the introduction rates of AEtOH and AEAEtOH could not be calculated.

Example 4-2

Introduction of Secondary Amine and Amine Compound Having Hydroxyl Group

Example 4-2-1

Synthesis of Modified HA Having Diethylenetriamine (DETA)

HA (200 kDa)-TBA was dissolved in DMSO, so as to prepare a 5.0 mg/ml solution. Thereafter, diethylenetriamine (hereinafter also referred to as "DETA"; manufactured by Sigma-Aldrich) was added thereto at an equivalent ratio of HA unit/diethylenetriamine=1/100 (mol/mol). Thereafter, a BOP reagent was further added at an equivalent ratio of 1.5 to the HA unit, and the obtained mixture was then stirred for 3 hours. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH. Thereafter, the resultant was dialyzed against large excess amount of 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying. The introduction ratio was quantified by the $^1$H-NMR method (HA: methyl proton of N-acetyl group, 1.8 to 1.9 ppm; AM: three methylene protons of diethylenetriamine portion, 2.6 to 3.1 ppm). The introduction ratio was found to be 89.8%. The ¹H-NMR spectrum of the obtained sample is shown in FIG. 8.

Example 4-2-2

Synthesis of Modified HA Having 1,3-Diamino-2-Hydroxypropane (DAHP)

The same method as described in Example 4-2-1 was applied with the exceptions that 1,3-diamino-2-hydroxypropane (hereinafter also referred to as "DAHP"; manufactured by Sigma-Aldrich) was used instead of DETA, and DAHP was added at an equivalent ratio of HA unit/DAHP=1/50 (mol/mol) and that a BOP reagent was further added at an equivalent ratio of 2.5 to the HA unit, followed by stirring overnight. The introduction ratio was quantified by the ¹H-NMR method (HA: methyl proton of N-acetyl group, 1.8 to 1.9 ppm; AM: methine proton of 1,3-diamino-2-hydroxypropane portion, 2.6 to 2.8 ppm). The introduction ratio was found to be 99.0%. The ¹H-NMR spectrum of the obtained sample is shown in FIG. 8.

As a result of the ¹H-NM R measurement in Examples 4-2-1 and 4-2-2, it became clear that a diamine compound wherein a hydroxyl group is added to alkyl and an amine compound having a secondary amine can also be introduced.

Example 4-3

Synthesis of (HA-AM/OH) into which Hydroxyl Group and Amino Group have been Introduced Example 4-3-1

Figure 9:
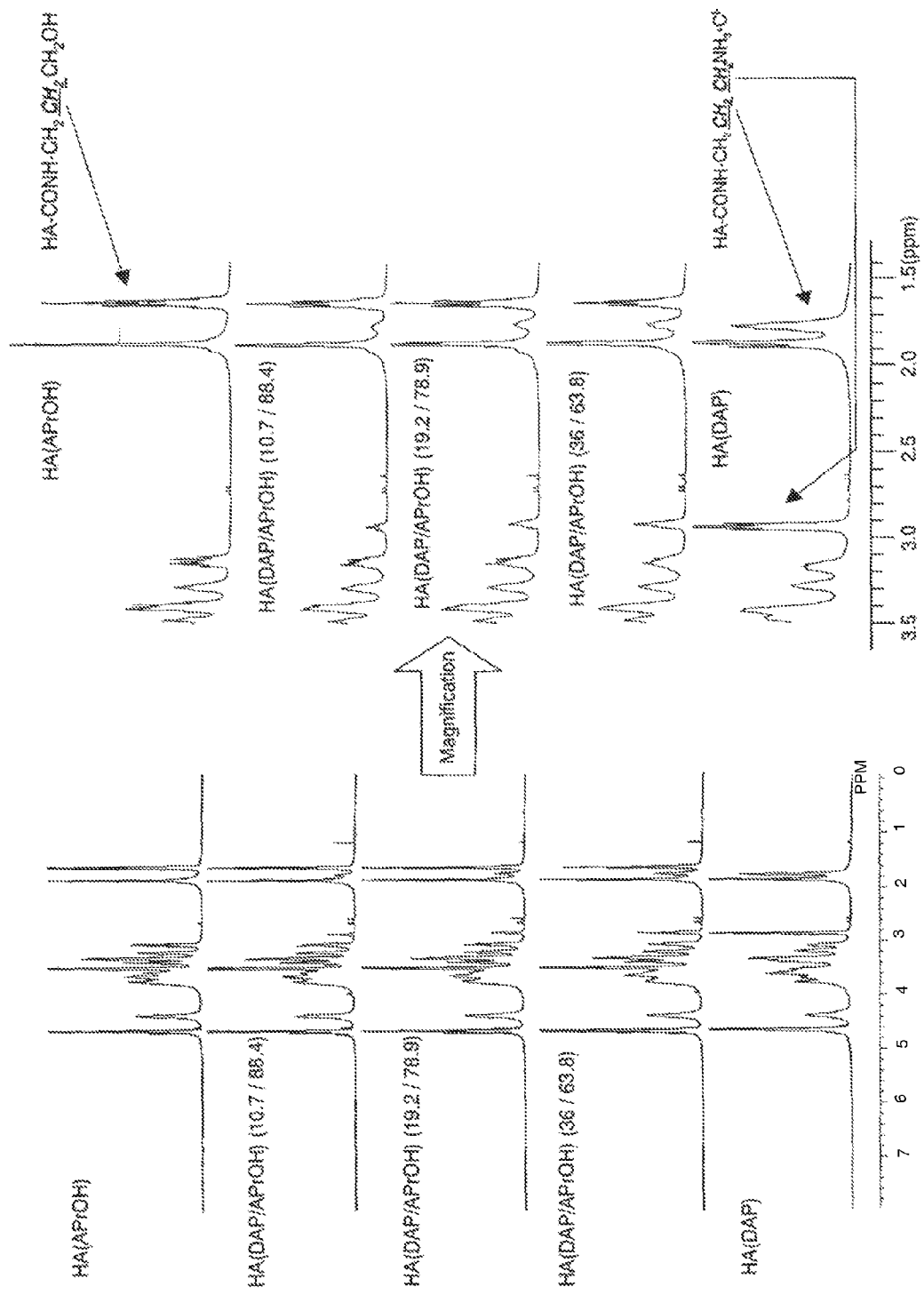
FIG. 9 shows an example of the $^1$H-NMR spectra of the water-soluble modified hyaluronic acid of the present invention.

Synthesis of Modified HA into which 3-Aminopropanol and 1,3-Diaminobutane have been Introduced Five solutions were prepared by dissolving HA (200 kDa)-TBA in DMSO resulting in a concentration of 5.0 mg/ml. As reaction reagents, 3-aminopropanol (hereinafter also referred to as "APrOH"; manufactured by Sigma-Aldrich) and 1,3-diaminopropane (hereinafter also referred to as "DAP"; manufactured by Sigma-Aldrich) were used. The reaction reagents were immobilized at an equivalent ratio of HA unit/the amino groups of the reaction reagents (APrOH+DAP)=1/50 (mol/mol). Thereafter, the reaction reagents were added to each solution, so that the molar ratio of APrOH:DAP (mol:mol) became 100:0, 95:2.5, 90:5, 80:10, and 0:100. Thereafter, a BOP reagent was further added to each solution at an equivalent ratio of 2.5 to the HA unit. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against large excess amount of 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying. The introduction rates of amino groups and hydroxyl groups were quantified by the ¹H-NMR method. The ¹H-NMR spectra are shown in FIG. 9 (HA: methyl proton of N-acetyl group, 1.8 to 1.9 ppm; AM: methylene proton of diaminopropane portion, 1.7 to 1.8, 2.9 to 3.0 ppm; OH: methylene proton of aminopropanol, 1.55 to 1.65 ppm).

Figure 10:
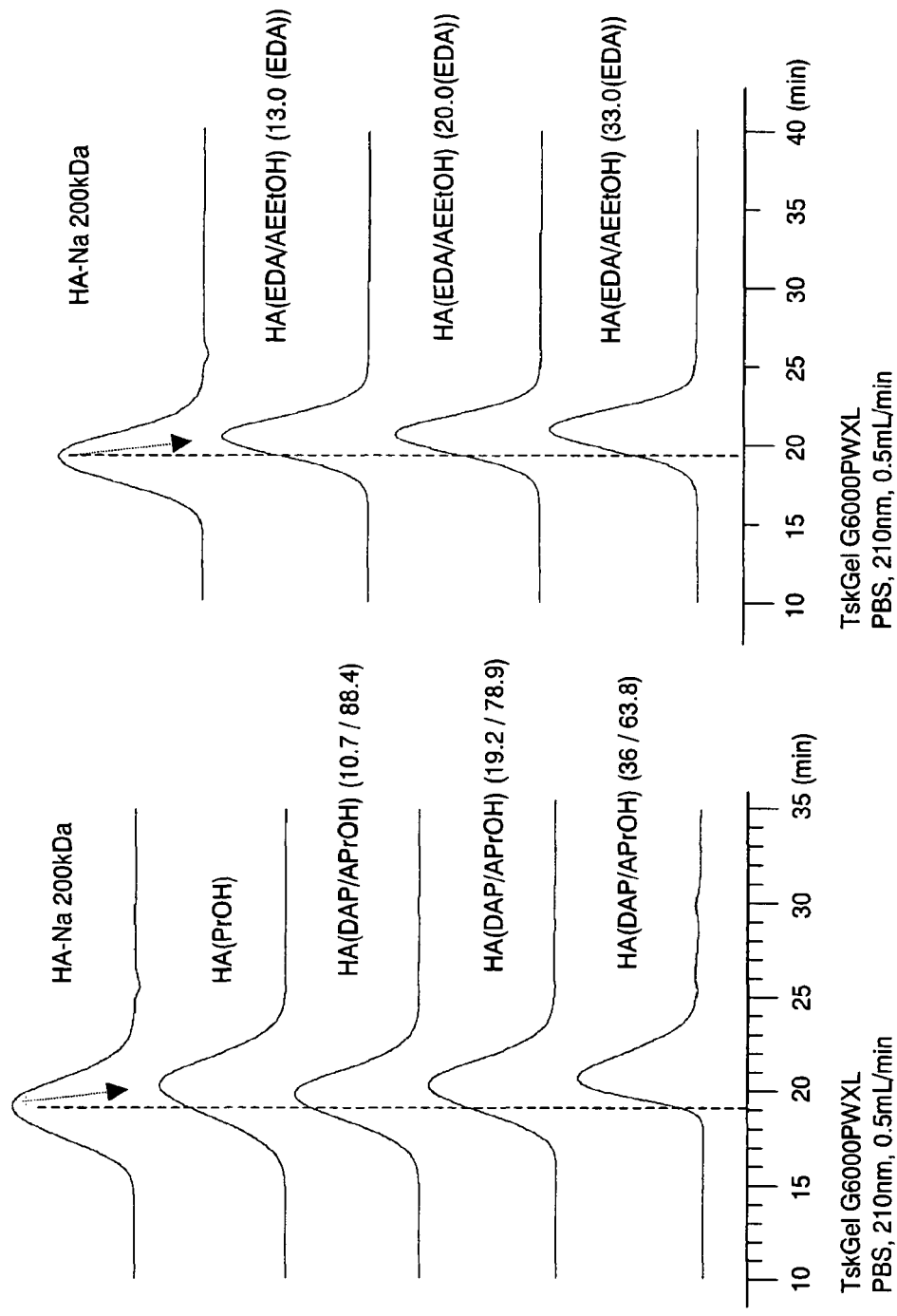
FIG. 10 shows an example of the GPC charts of the water-soluble modified hyaluronic acid of the present invention.

The introduction rates were as follows: 100:0 (APrOH:DAP)=100 mole %; 95:2.5 (APrOH: DAP)=88.4:10.7 mole %; 90:5 (APrOH:DAP)=78.9:19.2 mole %; 80:10 (APrOH: DAP)=63.8:36.0 mole %; 0:100 (APrOH:DAP)=93.2 mole % (hereinafter, a modified HA wherein the introduction ratio is 0:100 (APrOH:DAP)=93.2 mole % is also referred to as "HA-DAP"). In addition, the GPC chart is shown in FIG. 10 (control: sodium hyaluronate (HA-Na) of 200 kDa). By introducing a functional group that was not an ionic group, a phenomenon whereby a peak shifted to the low-molecular-weight side on the GPC chart and an apparent molecular weight was decreased was observed. Thus, it was suggested that an electrostatic or hydrogen bonding, intramolecular interaction should be changed. Moreover, it was observed that as a result of interaction with the column due to introduction of AM, the peak shifted to the low-molecular-weight side. From the results of Example 4-3-1, it became clear that a water-soluble modified HA having an amino group and a hydroxyl group can be synthesized, and that the introduction ratio thereof can be controlled.

Example 4-3-2

Synthesis of Modified HA into which (2-Aminoethoxy) Ethanol (AEEtOH) and Ethylenediamine (EDA) Have Been Introduced Instead of reaction reagents, amino propanol (APrOH) and diaminopropane (DAP), reaction reagents, (2-aminoethoxy) ethanol (hereinafter also referred to as "AEEtOH"; manufactured by Sigma-Aldrich) and ethylenediamine (EDA; manufactured by Sigma-Aldrich), were used.

Figure 11:
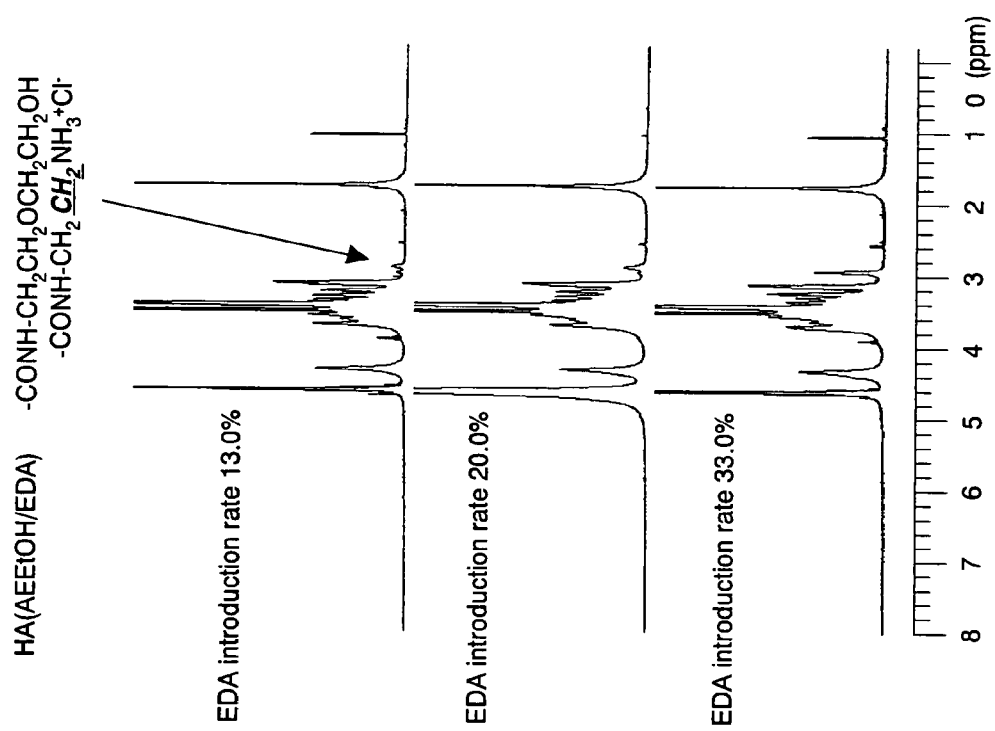
FIG. 11 shows an example of the $^1$H-NMR spectra of the water-soluble modified hyaluronic acid of the present invention.

The reaction reagents were immobilized at an equivalent ratio of HA unit/the amino groups of the reaction reagents (AEEtOH+EDA)=1/50 (mol/mol). Thereafter, the reaction reagents were added to each solution, so that the molar ratio of AEEtOH:EDA (mol:mol) became 95:2.5, 90:5, and 80:10, and the obtained mixture was then reacted. The same method as that described in Example 4-3-1 was applied with the above described exceptions. The introduction ratio of an amino group was quantified by the ¹H-NMR method. The ¹H-NMR spectra are shown in FIG. 11 (HA: methyl proton of N-acetyl group, 1.8 to 1.9 ppm; AM: methylene proton of ethylenediamine portion, 2.9 to 3.1 ppm). Each of the introduction rates of AM(EDA) were as follows: 95:2.5 (AEEtOH:EDA)=13.0 mole %; 90:5 (AEEtOHH:EDA)=20 mole %; and 80:10 (AEEtOH:EDA)=33.0 mole %. In addition, the GPC chart is shown in FIG. 10. As with Example 4-3-1, by introducing a functional group that was not an ionic group, a phenomenon whereby a peak shifted to the low-molecular-weight side on the GPC chart and an apparent molecular weight was decreased was observed. Thus, it was suggested that an electrostatic or hydrogen bonding, intramolecular interaction should be changed. Moreover, it was observed that as a result of interaction with the column due to introduction of AM, the peak shifted to the low-molecular-weight side.

Example 4-4

Evaluation of Enzymatic Degradability

Figure 12:
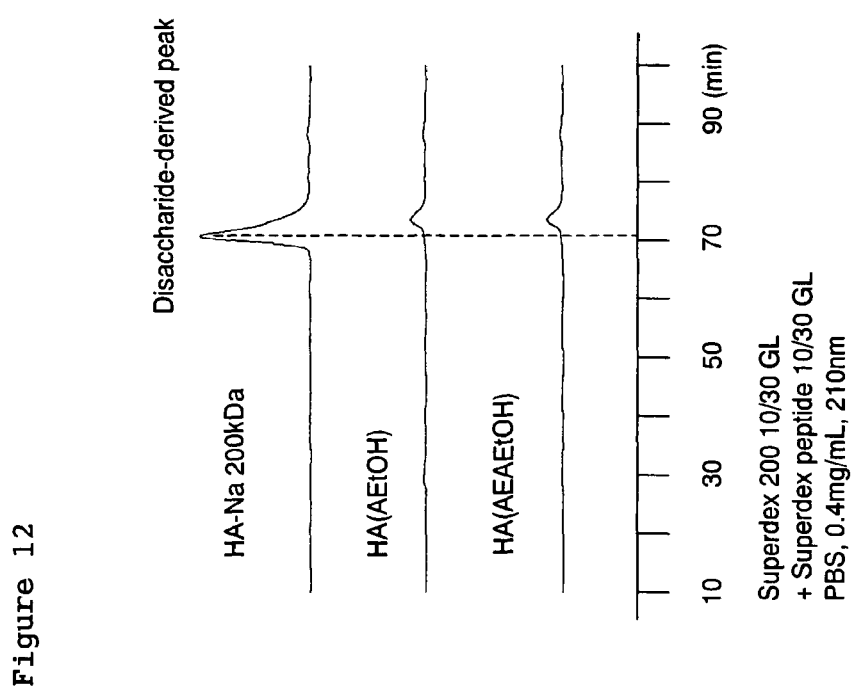
FIG. 12 shows an example of GPC charts obtained after treating the water-soluble modified hyaluronic acid of the present invention with hyaluronidase.
Figure 13:
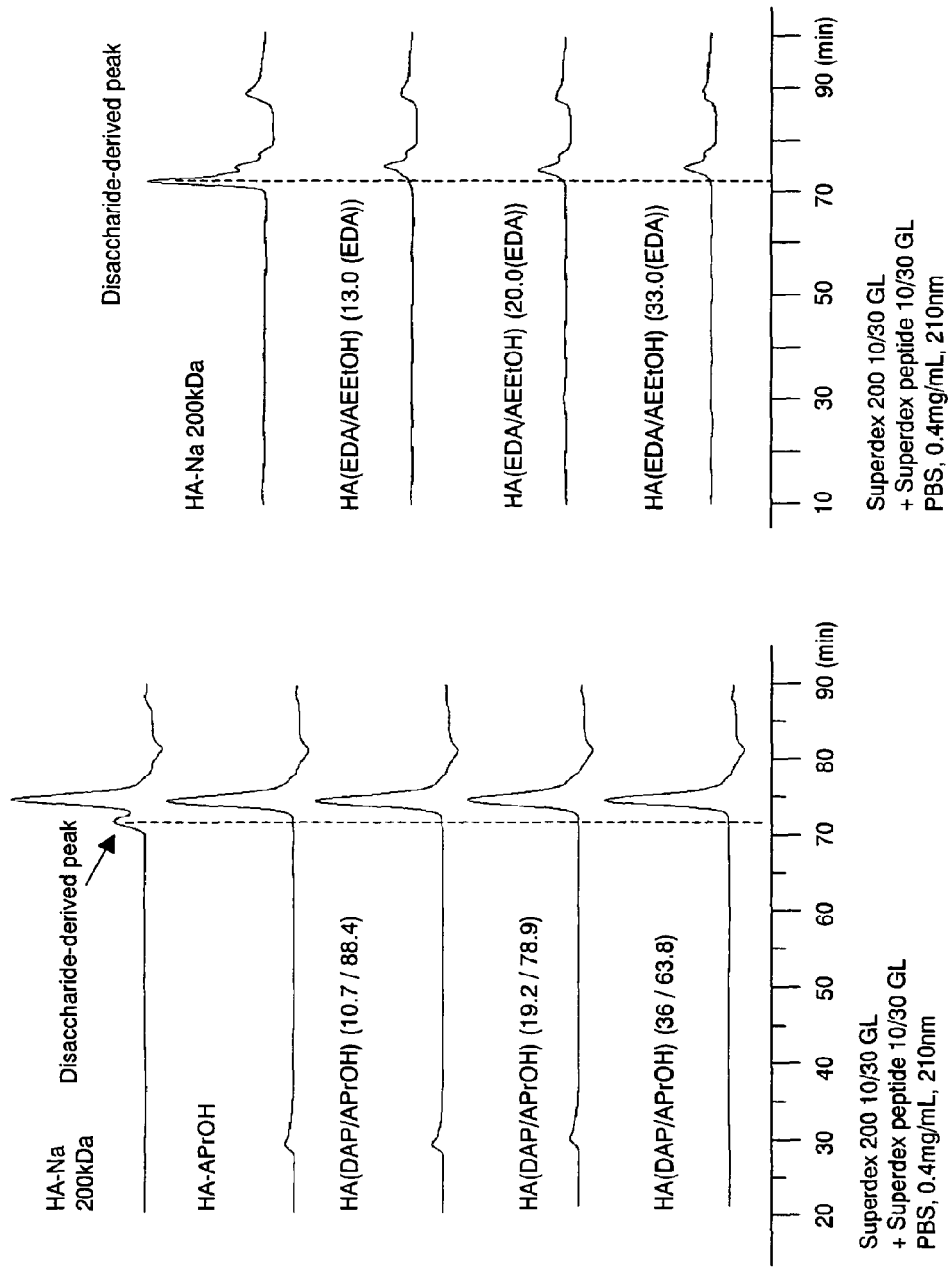
FIG. 13 shows an example of GPC charts obtained after treating the water-soluble modified hyaluronic acid of the present invention with hyaluronidase.

Enzymatic degradability was evaluated in the same manner as that in Example 3-3 with the exception that the samples obtained in Examples 4-1 and 4-3 were dissolved in distilled water (Milli Q water), resulting in a concentration of 4 mg/ml. In addition, because of the influence of an AM group upon analysis, evaluation of the percentage of disaccharide was not conducted. The results are shown in FIGS. 12 and 13.

In all the samples, the decomposition product of disaccharide was not observed, and thus it was suggested that a modified HA having enzyme resistance, which is capable of controlling electric charge and the introduction ratio of a reactive functional group, can be synthesized. The fact that no decomposition products of disaccharide were observed means that the percentage of a peak area derived from disaccharide to the entire peak area derived from a decomposition product was 30% or less, when the absorption at 232 nm of the decomposition product obtained from digestion by hyaluronidase was measured.

Example 5

Correlation Between Molecular Weight of Modified Hyaluronic Acid (HA-AM-SUC) and Residence Time in Blood (Molecular Weight Dependency)

In order to analyze the retention ability of a modified hyaluronic acid (HA-AM-SUC) in blood from the viewpoint of molecular weight, modified HAs were synthesized from HA having molecular weights of 23 k, 100 k, and 200 kDa, and FITC used as a fluorochrome was then introduced into the modified HAs, so as to prepare samples. Thereafter, the retention ability of each modified HA in blood was observed. (Example 5-1)

Synthesis of HA-AM

Figure 14:
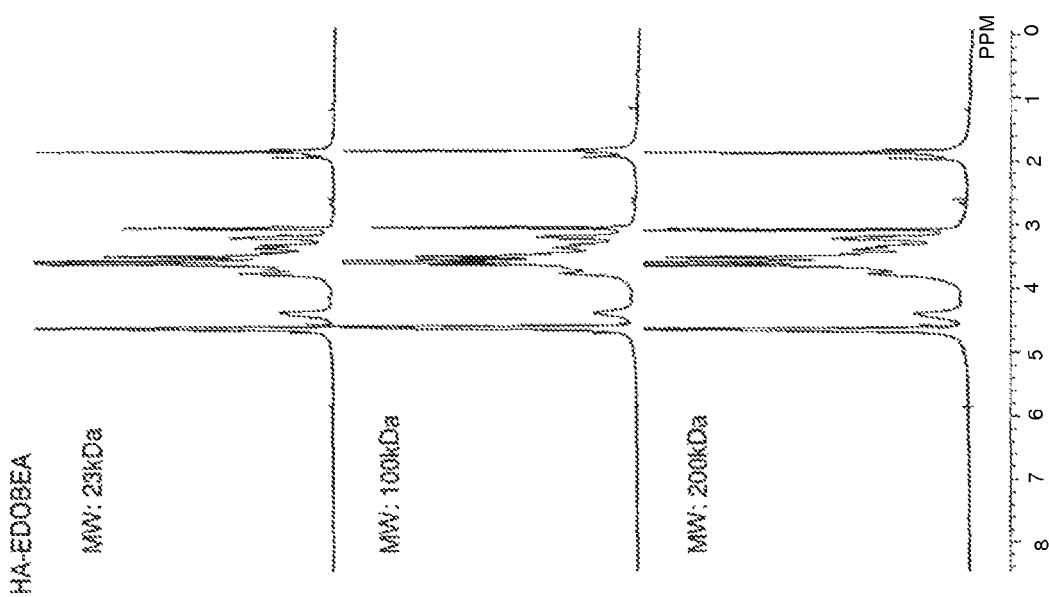
FIG. 14 shows an example of the $^1$H-NMR spectra of the water-soluble modified hyaluronic acid of the present invention.

HA (23 kDa)-TBA was dissolved in DMSO, resulting in a concentration of 2 mg/ml, so as to prepare a solution. In addition, HA (100 kDa)-TBA and HA (200 kDa)-TBA were dissolved in DMSO, resulting in a concentration of 4 mg/ml, so as to prepare solutions. Thereafter, 2,2'-(ethylenedioxy)bis(ethylamine)(EDOBEA) and BOP were added in this order to each of the above solutions at an equivalent ratio of HA unit/BOP/EDOBEA=1/2.5/50 (mol/mol/mol). The obtained mixture was then reacted at room temperature overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against large excess amount of distilled water (Milli Q water) for purification (Spectrapore 4; molecular weight cut off (MWCO): 12 k-14 kDa), followed by ultrafiltration (YM-10; manufactured by MILLIPORE). Thereafter, the resultant was freeze-dried, so as to obtain the captioned hyaluronic acid into which an amino group had been introduced (HA-AM). The introduction ratio of an amino group was quantified by the $^1$H-NMR method. The $^1$H-NMR spectra are shown in FIG. 14 (HA: methyl proton of N-acetyl group, 1.8 to 1.9 ppm; AM: methylene proton of EDOBEA portion, 2.9 to 3.1 ppm). Each of the introduction rates were as follows: 23 kDa:87 mole %, 10 kDa:92.5 mole %, 200 kDa:93.5 mole %.

Example 5-2

Synthesis of Fluorescein-Labeled Modified HA

The HA-AM obtained in the aforementioned (Example 5-1) was dissolved in distilled water (Milli Q water), so as to prepare a solution of a concentration of 20.0 mg/ml. Thereafter, a 0.2 M carbonate buffer (pH 9.0) was added to the prepared solution, resulting in a concentration of 10.0 mg/ml. Thereafter, fluorescein isothiocyanate (hereinafter also referred to as "FITC"; manufactured by Pierce) that was 0.07 mole times to an HA unit (1 unit=a repeating unit, N-acetyl-glucosamine-glucuronic acid) was dissolved in DMSO that was 1/10 the volume of an HA-AM solution. The DMSO solution was then added to the above solution, and the obtained mixture was then stirred in the dark at room temperature for 1 hour. Thereafter, succinic anhydride (manufactured by Wako Pure Chemical Industries, Ltd.) that was 40 mole times to the HA unit was dissolved in DMSO that was 1/10 the volume of the HA-AM solution. The DMSO solution was then added to the above solution, and the obtained mixture was then stirred in the dark at room temperature for 30 minutes. Thereafter, the resultant was roughly purified by gel filtration using a PD-10 column (manufactured by Amersham Biosciences), and it was then dialyzed against large excess amount of 0.5 M NaCl aqueous solution for purification (Spectrapore 4; molecular weight cut off (MWCO): 12 k-14 kDa). Furthermore, the external dialysis solution was exchanged with large excess amount of distilled water (Milli Q water), and dialysis was carried out in the dark for purification. The obtained aqueous solution was freeze-dried, so as to obtain fluorescein-labeled HA-AM-SUC.

Each of the thus obtained fluorescein-labeled HA-AM-SUC was dissolved in a 50 mM carbonate buffer (pH 9.0), resulting in a concentration of 0.25 mg/ml. Based on the absorbance of the solution at 494 nm, the molar concentration of an N-fluorosceinylthiocarbamoyl group derived from FITC was quantified, and the concentration of each unit was then calculated in accordance with the following formula. Moreover, conversion to a molar percentage, and calculation of a weight percentage derived from HA in the modified HA, were carried out.

Unmodified HA Unit: x μmol/ml

HA-AM-SUC unit: y μmol/ml (the unit wherein AM was treated with succinic anhydride) Based on the above definitions, the percentage was calculated according to the following formulas:

[Formula 8]

$(401.3 \times x)+(631.58 \times y)+(544.97 \times (\text{remaining AM conc.}))+(898.9 \times (\text{FITC conc.}))=250$ mg      Equation 1:

$x/(y+(\text{remaining AM conc.})+(\text{FITC conc.}))=(100-\text{AM}(\%))/\text{AM}(\%)$      Equation 2:

It is to be noted that in the above formulas, the remaining AM conc. means the molar concentration of a unit having an unreacted amino group, and that FITC conc. means the molar concentration of a unit having an FITC group.

The obtained results are summarized in Table 4.

TABLE 4

| FITC-labeled HA-AM-SUC used in pharmacokinetic studies | | | | | | |
|---|---|---|---|---|---|---|
| Molecular weight (kDa) | AM (%) NMR | Remaining AM (%) TNBS | HA-AM-FITC unit (mole %) | HA-AM-SUC unit (mole %) | Unmodified HA unit (mole %) | HA (weight %) |
| 23 | 87.0 | — | 1.0 | 86.0 | 13.0 | 63.7 |
| 100 | 92.5 | — | 0.9 | 91.6 | 7.5 | 62.3 |
| 200 | 93.5 | 1.5 | 0.7 | 91.3 | 6.5 | 62.9 |

—: less than quantitative limit

Comparative Example 5-1

Synthesis of Fluorescein-Labeled HA-HZ-SUC

Hyaluronic acid sodium salt of 580 kDa (manufactured by Denki Kagaku Kogyo Kabushiki Kaisha) was dissolved in a concentration of 0.25% (w/v) in distilled water, and the pH was then adjusted to pH 4.7 to 4.8 by addition of 5N hydrochloric acid solution. Thereafter, 1-ethyl-3-(3-dimethylaminopropyl)carbodiimide (EDC) and adipic acid dihydrazide (hereinafter also referred to as "ADH") were added thereto, resulting in a molar ratio of HA unit: EDC: ADH=1:5:40. Thereafter, while maintaining the pH at pH 4.7 to 4.8 by addition of 5N hydrochloric acid solution, the obtained mixture was reacted at room temperature for 2 hours. Thereafter, the reaction solution was dialyzed against large excess amount of 10 mM sodium chloride solution, a 25% ethanol aqueous solution, and distilled water (Milli Q water) in this order (Spectrapore 7; molecular weight cut off (MWCO): 12 k-14 kDa), followed by freeze-drying, so as to obtain hyaluronic acid into which a hydrazide group had been introduced (HA-HZ). The HZ introduction ratio in HA-HZ was quantified in terms of an ADH introduction ratio by the $^1$H-NMR method. As a result, it was found to be 73% of carboxy groups of HA.

This HA-HZ was dissolved in distilled water (Milli Q water), and an equal amount of 100 mM carbonate buffer (Ph 9.0) was then added thereto to a final concentration of 1 mg/ml. Thereafter, FITC dissolved in DMSO that was 1/10 the volume of the HA-HZ solution was added to the mixture at an additive ratio of FITC/HA unit=3.0 mol/mol, and the obtained mixture was then reacted in the dark at room temperature for 1 hour. Thereafter, 25 ml of the reaction solution was poured in PD-10 columns (10 columns) that had previously been equilibrated with a 50 mM carbonate buffer (pH 9.0), so as to remove unreacted FITC. Succinic anhydride dissolved in DMSO (3.5 ml) was added to the thus roughly purified solution at an additive ratio of succinic anhydride/HZ=250 mol/mol, and the same above reaction was carried out. The reaction mixture was dialyzed against large excess amount of distilled water (Milli Q water) for purification, followed by freeze-drying, so as to obtain fluorescein-labeled HA-HZ-SUC, which was formed by labeling HA-HZ with FITC.

Each of the obtained fluorescein-labeled HA-HZ was dissolved in a concentration of 0.25 mg/ml in a 50 mM carbonate buffer (pH 9.0). The concentration of FITC was quantified based on the absorbance at 494 nm of the obtained solution, and the concentration of each unit was then calculated according to the following formulas. Further, conversion to a molar percentage, and calculation of a weight percentage derived from HA in the modified HA, were carried out.

Unmodified HA unit: x μmol/ml

HA-HZ-SUC unit: y μmol/ml (the unit wherein HZ was treated with succinic anhydride)

Based on the above definitions, the percentage was calculated according to the following formulas:

[Formula 9]

$$(379.3 \times x)+(635.57 \times y)+(924.88 \times (\text{FITC conc.}))=250 \text{ mg} \quad \text{Equation 1:}$$

$$x/(y+(\text{FITC conc.}))=(100-\text{HZ (\%)})/\text{HZ (\%)} \quad \text{Equation 2:}$$

It is to be noted that in the above formulas, FITC conc. means the molar concentration of a unit having an FITC group. The obtained results are summarized in Table 5.

TABLE 5

FITC-labeled HA-HZ-SUC used in pharmacokinetic studies

| HZ (%) NMR | Remaining HZ (%) TNBS | HA-FITC unit (mole %) | HA-SUC unit (mole %) | Unmodified HA unit (mole %) | HA (weight %) |
|---|---|---|---|---|---|
| 73 | — | 1.1 | 71.9 | 27.0 | 67.8 |

—: less than quantitative limit

Example 5-3

Evaluation of Residence Time in Blood

HA-Administered Rat Plasma Sample

Each of the fluorescein-labeled modified HAs of Example 5-2 and Comparative Example 5-1 was administered in a dosage of 10 mg/kg into the vein (iv) and subcutis (sc) of a rat as a single dose. The blood was collected (heparin treatment) before administration and 0.0833, 0.25, 0.5, 1.2, 2, 4, 6, 8, 10, 12, 24, 48, 72, 96, and 168 hours after administration. Thereafter, plasma was obtained by centrifugation (0.25, 1.2, 6, 10, and 12 hours after administration, the blood was collected regarding only the sample of Comparative Example 5-1). This plasma sample was cryopreserved at −20° C. (or lower until the measurement was carried out.

Measurement Method

A standard sample used for calibration curve and a measurement sample were analyzed by GPC. Conditions for measurement are described below:

GPC Column: TSKgel G6000PW$_{XL}$ (manufactured by TOSOH)

Mobile phase: PBS (pH 7.4)

Elution mode: Isocratic

Flow ratio: 0.5 ml/min

Injection volume: 40 μl

Detection: Fluorescence (EX: 494 nm, EM: 518 nm)

Preparation of Measurement Sample

Sample Used for Calibration Curve

Each fluorescein-labeled modified HA was diluted with PBS (pH 7.4), so as to prepare standard solutions having concentrations of 1, 5, 10, 50, 100, 500 μg/ml and 0 μg/ml (control, PBS (pH 7.4)). Thereafter, an equal volume of normal rat plasma was added to each standard solution, so as to prepare a sample used for calibration curve.

Preparation of Measurement Sample

An equal volume of PBS (pH 7.4) was added to a modified HA-administered rat plasma sample, so as to prepare a measurement sample.

Calculation of Concentration of Modified HA in Plasma

A peak area was calculated using analysis software Millenium Ver 3.21 (manufactured by Waters). The concentration of the modified HA in plasma was calculated based on the calibration curve obtained from the peak area of each standard sample.

Pharmacokinetic Data

With regard to data of changes in the concentrations in blood of the fluorescein-labeled modified HAs of Example 5-2 and Comparative Example 5-1, pharmacokinetic parameters were calculated using WinNonlin Ver 4.0.1 (manufactured by Pharsight). Model-independent analysis was carried out using data of the final 3 measurement points of individuals, so as to calculate the half-life (t½) and the mean residence time in blood (MRT). In addition, bioavailability (BA) after subcutaneous administration was calculated from the area under the curve after subcutaneous administration (AUCsc)

and the area under the curve after intravenous administration (AUCiv) according to the following formula:

BA (%)=AUCsc/AUCiv×100          [Formula 10]

Figure 15:
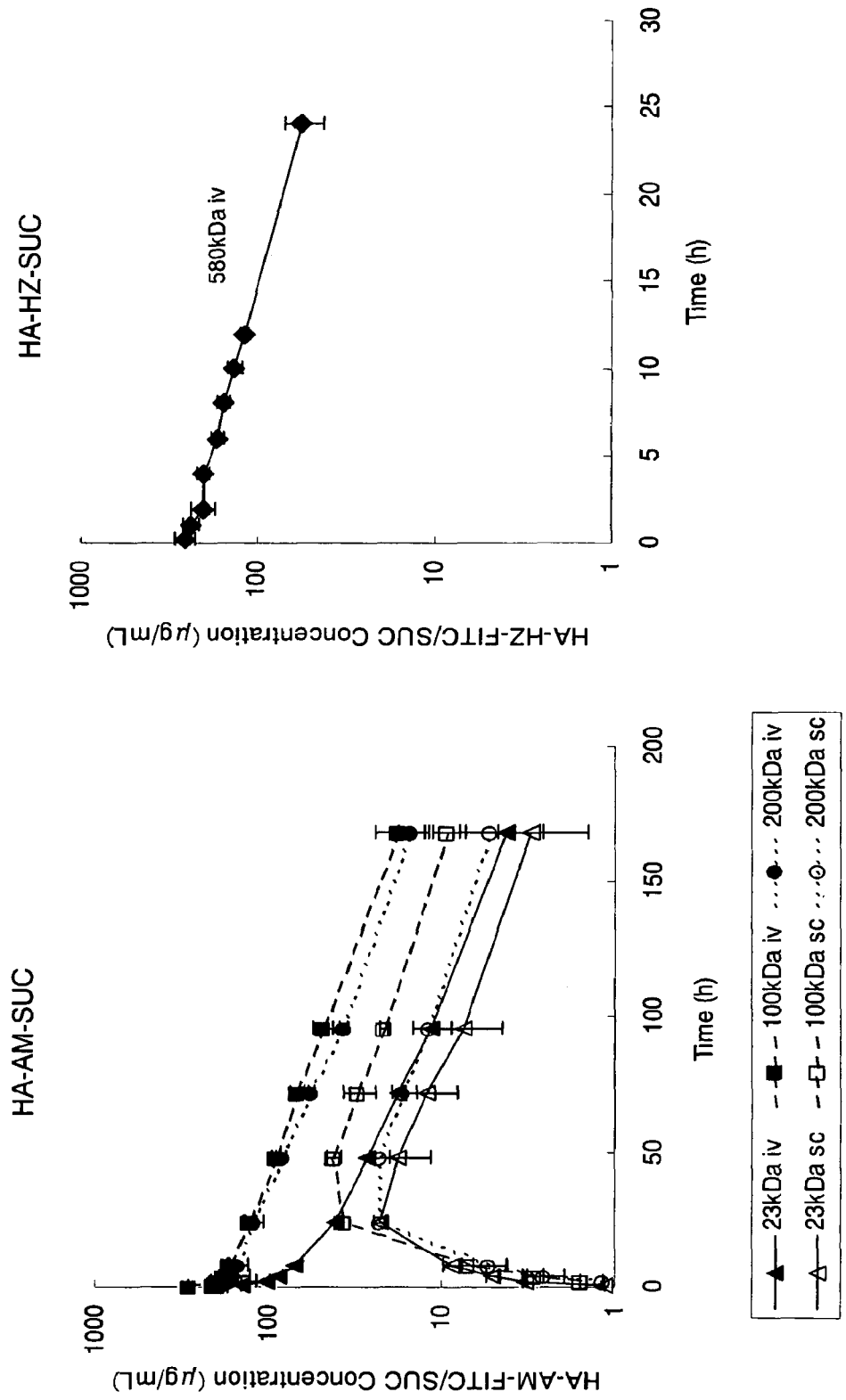
FIG. 15 is a view showing changes in the blood concentrations of fluorescein-labeled modified HAs having different molecular weights, HA-AM-SUC and HA-HZ-SUC.

Changes in the concentrations of the fluorescein-labeled modified HAs in blood are shown in FIG. 15, and the calculated pharmacokinetic parameters are shown in Table 6.

TABLE 6

Pharmacokinetic parameters of FITC-labeled modified HAs

| Molecular weight (kDa) | AM (HZ) (%: NMR) | Cl (mL/hr/kg) | BA (%) | MRT (h) | t½ |
|---|---|---|---|---|---|
| 23 (iv) | 87.0 | 2.44 | — | 86.0 | 47.3 |
| 100 (iv) | 92.5 | 0.76 | — | 91.6 | 49.3 |
| 200 (iv) | 93.5 | 0.87 | — | 91.3 | 44.7 |
| 23 (sc) | 87.0 | 5.40 | 46.4 | 83.9 | 50.8 |
| 100 (sc) | 92.5 | 2.18 | 37.2 | 101.4 | 56.5 |
| 200 (sc) | 93.5 | 3.76 | 23.3 | 98.7 | 57.6 |
| 580 (iv) | 73.0 (HZ) | 2.52 | — | 16.3 | 11.2 |

As a result of the pharmacokinetic studies using fluorescein-labeled modified HAs, it was confirmed that when compared with HA and the previously reported HA derivatives (refer to Patent Documents 4, 5, and 6), the use of the modified HA of the present invention synthesized in an aprotic polar organic solvent (Example 5-2) significantly improves the residence time in blood after intravenous administration of the above modified product to a rat as a single dose. Moreover, the mean residence time in blood (MRT) after intravenous administration of the modified HA of Comparative Example 5-1 (modified HA having a molecular weight of 580 kDa (73 mole % modification (HZ)) to a rat as a single dose was approximately 16 hours. In contrast, in the case of the modified HA of the present invention, it was clarified that the retention ability in blood was extended by approximately 5.5 times. With regard to the modified HA of 23 kDa, a reduction in the blood concentration was observed at the initial stage, and thus it was suggested that a portion of a low-molecular-weight modified HA might be subjected to renal excretion. With regard to the modified HAs of 100 kDa and 200 kDa, characteristics regarding retention ability in blood (CL, MRT, t1/2) were almost the same values. However, bioavailability (BA) obtained after subcutaneous administration decreased molecular-weight-dependently, and thus it was found that as the molecular weight of a modified HA becomes higher, the modified HA is hardly transferred into the blood.

Example 6

Correlation Between Modification Ratio of Modified Hyaluronic Acid (HA-AM-SUC) and Residence Time in Blood In order to analyze the retention ability in blood of the modified hyaluronic acid (HA-AM-SUC) from the viewpoint of modification ratio, modified HAs having various modification rates were synthesized from HA of 200 kDa, and samples into which FITC used as a fluorochrome had been introduced were then prepared. The retention ability in blood of each sample was observed.

Example 6-1

Preparation of HA-AM

Figure 16:
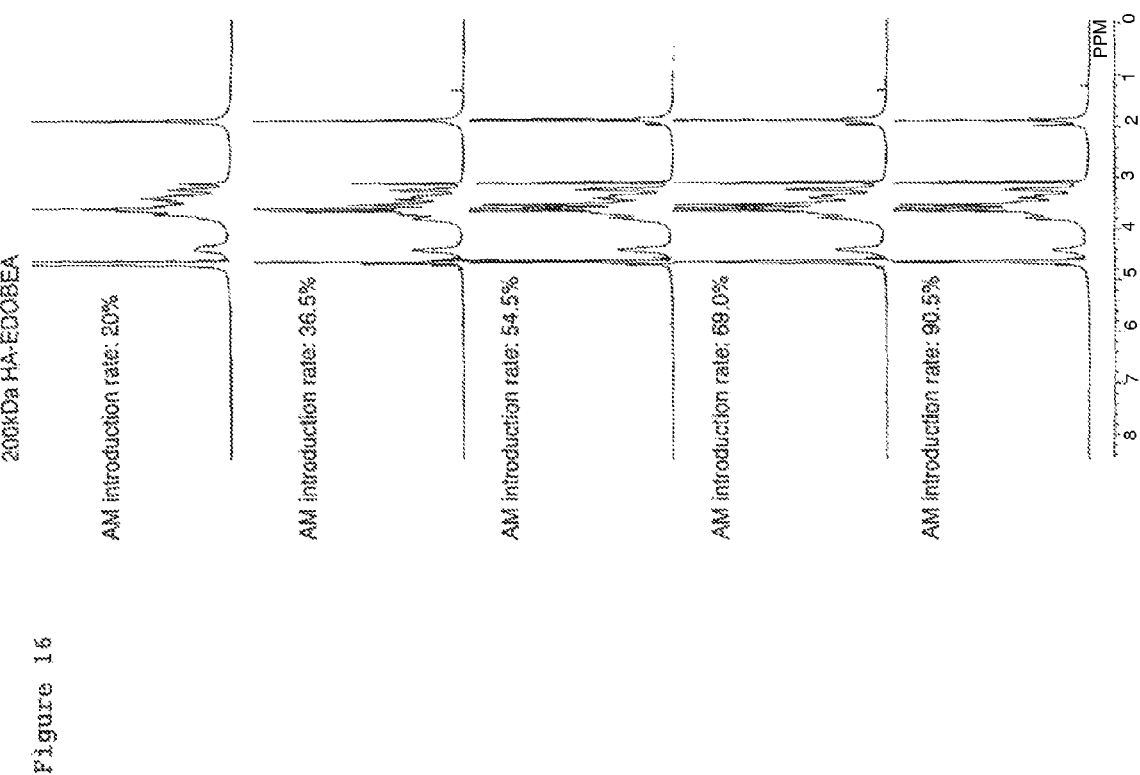
FIG. 16 shows an example of the $^1$H-NMR spectra of the water-soluble modified hyaluronic acid of the present invention.

Five solutions were prepared by dissolving HA (200 kDa)-TBA in DMSO, resulting in a concentration of 4.0 mg/ml. EDOBEA was added to each solution at an equivalent ratio of HA unit/EDOBEA=1/50 (mol/mol). A BOP reagent was added to each solution at an equivalent ratio of 0.25, 0.5, 0.75, 1.0, or 1.5 to the HA unit, and the obtained mixture was then reacted overnight. Thereafter, a 1 M NaCl aqueous solution was added thereto in an amount that was half the volume of the reaction mixture, and 5N HCl solution was then added to the mixture to decrease the pH to pH 3. Thereafter, the resultant was neutralized with 2N NaOH solution. Thereafter, the resultant was dialyzed against large excess amount of distilled water (Milli Q water) for purification (Spectrapore 4; molecular weight cut off (MWCO): 12 k-14 kDa), followed by ultrafiltration (YM-10; manufactured by MILLIPORE). Thereafter, the resultant was freeze-dried. The amino group introduction ratio was quantified by the $^1$H-NMR method. The $^1$H-NMR spectra are shown in FIG. 16 (HA: methyl proton of N-acetyl group, 1.8 to 1.9 ppm; AM: methylene proton of EDOBEA portion, 2.9 to 3.1 ppm). The introduction rates were the BOP reagent ratio 0.25:20.0 mole %, 0.5:36.5 mole %, 0.75:54.5 mole %, 1.0:69.0 mole %, and 1.5:90.5 mole %, respectively.

Example 6-2

Synthesis of Fluorescein-Labeled Modified HA

Each of the HA-AM as obtained above (Example 6-1) was dissolved in distilled water (Milli Q water), resulting in a concentration of 20.0 mg/ml. Thereafter, a 0.2 M carbonate buffer (pH 9.0) was added to the obtained solution, resulting in a concentration of 10.0 mg/ml. Thereafter, fluorescein isothiocyanate that was 0.07 mole times (69% and 90.5% amine-modified HA solutions), 0.175 mole times (54.5% amine-modified HA solution), 0.28 mole times (36.5% amine-modified HA solution), and 0.63 mole times (20.0% amine-modified HA solution) to an HA unit (1 unit=a repeating unit, N-acetylglucosamine-glucuronic acid) was dissolved in DMSO that was 1/10 the volume of an HA-AM solution. The DMSO solution was then added to the above solution, and the obtained mixture was then stirred in the dark at room temperature for 1 hour. Thereafter, succinic anhydride that was 40 mole times to the HA unit (1 unit=a repeating unit, N-acetylglucosamine-glucuronic acid) was dissolved in DMSO that was 1/10 the volume of the HA-AM solution. The DMSO solution was then added to the above reaction solution, and the obtained mixture was then stirred in the dark at room temperature for 30 minutes. The 20% amine modified product was first dialyzed against large excess amount of DMSO, and was then dialyzed against large excess amount of 25% EtOH aqueous solution. On the other hand, other samples were directly dialyzed against large excess amount of 25% EtOH aqueous solution (Spectrapore 4; molecular weight cut off (MWCO): 12 k-14 kDa). Thereafter, these solutions were dialyzed against a 0.5 M NaCl aqueous solution for purification. Furthermore, the external dialysis solution was exchanged with distilled water (Milli Q water), and dialysis was carried out in the dark for purification. The obtained aqueous solution was freeze-dried, so as to obtain fluorescein-labeled HA-AM-SUC.

Each of the thus obtained fluorescein-labeled HA-AM-SUC was dissolved in a 50 mM carbonate buffer (pH 9.0), resulting in a concentration of 0.25 mg/ml. Based on the absorbance at 494 nm of the solution, the FITC concentration was quantified, and the concentration of each unit was then calculated in accordance with the following formula. Moreover, conversion to a molar percentage, and calculation of a weight percentage derived from HA in the modified HA, were carried out.

Unmodified HA unit: x μmol/ml
HA-AM-SUC unit: y μmol/ml (the unit wherein AM was treated with succinic anhydride)
Based on the above definitions, the percentage was calculated according to the following formulas:
[Formula 11]

$$(401.3 \times x)+(631.58 \times y)+(544.97 \times (\text{remaining AM conc.}))+(898.9 \times (\text{FITC conc.}))=250 \text{ mg} \quad \text{Equation 1:}$$

$$x/(y+(\text{remaining AM conc.})+(\text{FITC conc.}))=(100-\text{AM}(\%))/\text{AM}(\%) \quad \text{Equation 2:}$$

It is to be noted that in the above formulas, FITC conc. means the molar concentration of a unit having an FITC group. The obtained results are summarized in Table 7.

TABLE 7

FITC-labeled HA-AM-SUC used in pharmacokinetic studies

| BOP ratio (BOP mole/HA unit mole) | AM (%) NMR | Remaining AM (%) TNBS | HA-AM-FITC unit (mole %) | HA-AM-SUC unit (mole %) | Unmodified HA unit (mole %) | HA (weight %) |
|---|---|---|---|---|---|---|
| 0.25 | 20.0 | 1.6 | 0.3 | 18.1 | 80.0 | 87.2 |
| 0.50 | 36.5 | 2.4 | 0.9 | 33.2 | 63.5 | 81.7 |
| 0.75 | 54.5 | 2.4 | 1.6 | 50.5 | 45.5 | 75.6 |
| 1.00 | 69.0 | — | 0.6 | 68.4 | 31.0 | 68.2 |
| 1.50 | 90.5 | — | 0.9 | 89.6 | 9.5 | 62.8 |

—: less than quantitative limit

Example 6-3

Evaluation of Residence Time in Blood
HA-Administered Rat Plasma Sample
The fluorescein-labeled modified HA of Example 6-2 was administered in a dosage of 10 mg/kg into the vein of a rat as a single dose. The blood was collected (heparin treatment) before administration and 0.5, 2, 4, 8, 24, 48, 72, 96, and 168 hours after administration. Thereafter, plasma was obtained by centrifugation. This plasma sample was cryopreserved at −20° C. or lower until the measurement was carried out.
Measurement Method
A standard sample used for calibration curve and a measurement sample were dispensed into a 96-well plate, and they were analyzed using a microplate reader. Conditions for measurement are described below:
Microplate reader: SPECTRA MAX GEMINI (manufactured by Molecular Devices)
Sample volume: 100 μl/well
Detection: Fluorescence (EX: 485 nm, EM: 538 nm)
Preparation of Measurement Sample
Sample Used for Calibration Curve
Each fluorescein-labeled modified HA was diluted with PBS (pH 7.4), so as to prepare standard solutions having concentrations of 1, 5, 10, 50, 100, 500 μg/ml and 0 μg/ml (control, PBS (pH 7.4)). Thereafter, an equal volume of normal rat plasma was added to each standard solution, so as to prepare a sample used for calibration curve.
Preparation of Measurement Sample
An equal volume of PBS (pH 7.4) was added to a modified HA-administered rat plasma sample, so as to prepare a measurement sample.
Calculation of Concentration of Modified HA in Plasma
The concentration of the modified HA in plasma was calculated based on the calibration curve obtained from the fluorescence intensity of each standard sample using analysis software SOFTmax PRO (manufactured by Molecular Devices).

Figure 17:
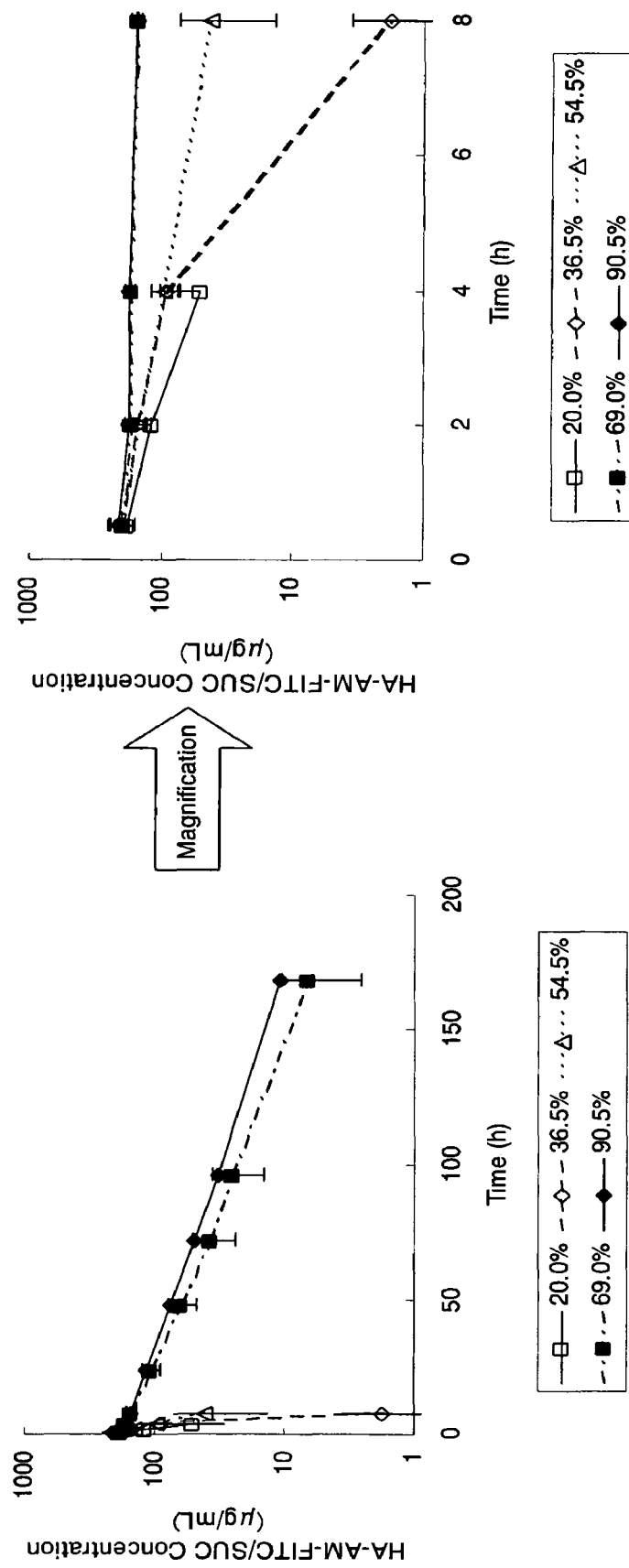
FIG. 17 is a view showing changes in the blood concentrations of fluorescein-labeled modified HAs having different amino group modification rates, which have been synthesized from HA having a molecular weight of 200 kDa.
Figure 18:
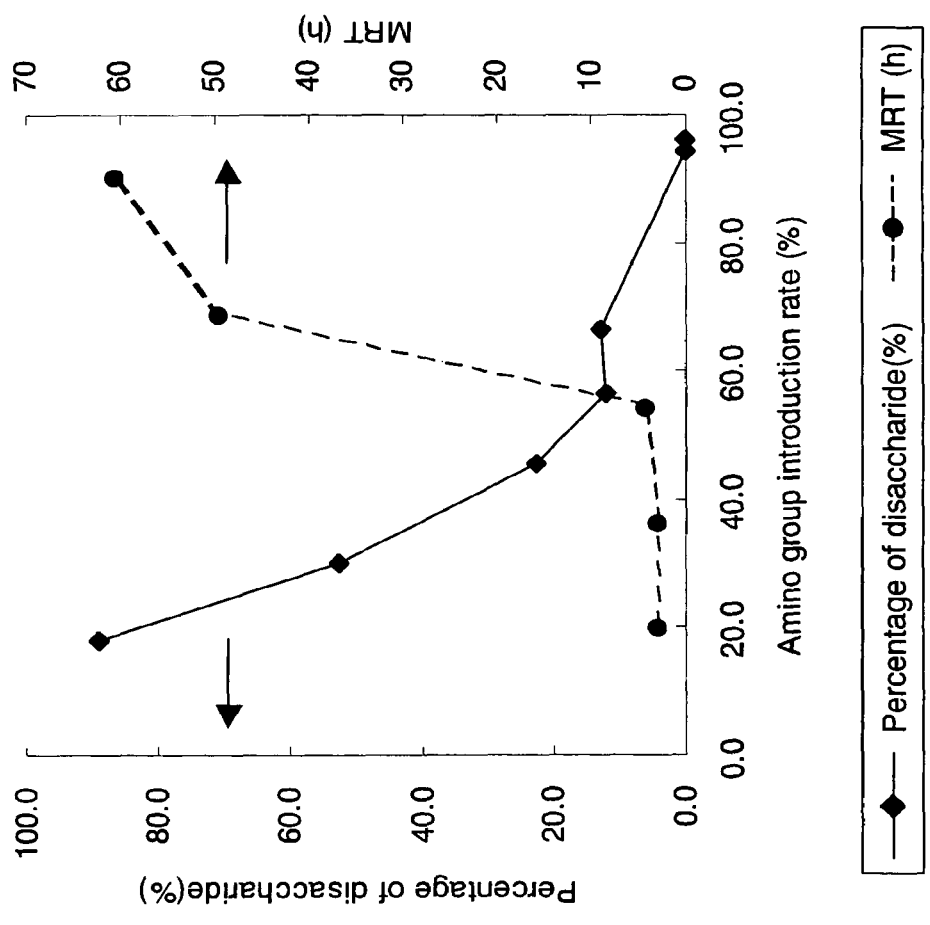
FIG. 18 is a view showing the correlation between the amino group introduction ratio of a modified HA and a mean residence time in blood (MRT), and also the correlation of an amino group introduction ratio and the percentage of disaccharide released by hyaluronidase digestion.

Pharmacokinetic Data
With regard to data of changes in the concentrations in blood of the fluorescein-labeled modified HAs of Example 6-2, pharmacokinetic parameters were calculated using WinNonlin Ver 4.0.1 (manufactured by Pharsight). With regard to a change in the concentration in plasma of each individual, model-independent analysis was carried out, so as to calculate the mean residence time in blood (MRT). The half-life (t1/2) was calculated using the data of the final 3 measurable points of each individual. Such a change in the concentration in blood of the fluorescein-labeled modified HA is shown in FIG. 17, and the relationship between the AM introduction ratio and MRT is shown in FIG. 18. Moreover, the calculated pharmacokinetic parameters are shown in Table 8.

TABLE 8

Pharmacokinetic parameters of FITC-labeled modified HAs

| AM (%: NMR) | Cl (ml/hr/kg) | MRT (h) | t½ |
|---|---|---|---|
| 20.0 | 16.37 | 2.81 | 1.95 |
| 36.5 | 12.96 | 2.90 | 1.62 |
| 54.5 | 10.47 | 4.26 | 2.76 |
| 69.0 | 1.20 | 49.6 | 36.7 |
| 90.5 | 0.97 | 60.6 | 44.5 |

From the relationship between the AM modification ratio and MRT as shown in FIG. 18, it was suggested that a significant increase in MRT, that is, elongation of the residence time in blood, occurs after the modification ratio reaches the latter half of 50%. That is to say, when the modification ratio is 55 mole % or more, preferably 65 mole % or more, and more preferably 69 mole % or more, there is a high possibility that a modified HA, which has MRT of 18 hours or more and thus is preferable in terms of the residence time in blood, can be obtained.

It is considered that since a modified HA that has acquired enzyme resistance has a significantly decreased recognition by CD44 receptor, it stays in blood for a long period of time.

Example 7

Residence Time in Blood of Modified Hyaluronic Acid Modified with Various Compounds In order to analysis the influence of modification upon the retention ability in blood of a modified hyaluronic acid (HA-AM-SUC), HA of 200 kDa was modified with various diamine compounds, and FITC used as a fluorochrome was then introduced into each of the thus modified HA, so as to prepare modified HA samples. Thereafter, the retention ability in blood of each sample was observed.

Example 7-1

Synthesis of Fluorescein-Labeled Modified HA

Each of the HA-DETA, HA-DAHP, and HA-DAP obtained in Example 4-2 and Example 4-3-1 was dissolved in distilled water (Milli Q water), so as to prepare a solution of a concentration of 20.0 mg/ml. Thereafter, a 0.2 M carbonate buffer (pH 9.0) was added to the prepared solution, resulting in a concentration of 10.0 mg/ml. Thereafter, fluorescein isothiocyanate that was 0.07 mole times to an HA unit was dissolved in DMSO that was 1/10 the volume of a modified HA solution. The DMSO solution was then added to the above solution, and the obtained mixture was then stirred in the dark at room temperature for 1 hour. Thereafter, succinic anhydride that was 40 mole times to the HA unit was dissolved in DMSO that was 1/10 the volume of the HA-AM solution. The DMSO solution was then added to the above solution, and the obtained mixture was then stirred in the dark at room temperature for 30 minutes. Thereafter, each sample was dialyzed against large excess amount of 0.5 M NaCl aqueous solution for purification, and the external dialysis solution was then exchanged with distilled water (Milli Q water), followed by further dialysis and purification (Spectrapore 4; molecular weight cut off (MWCO): 12 k-14 kDa). The obtained aqueous solution was freeze-dried, so as to obtain a fluorescein-labeled modified HA.

The concentration of FITC was quantified based on the absorbance at 494 nm of each of the obtained 0.25 mg/ml fluorescein-labeled HA-AM-SUC, and the concentration of each unit was then calculated in accordance with the following formula. Moreover, conversion to a molar percentage, and calculation of a weight percentage derived from HA in the modified HA, were carried out.

Unmodified HA unit: x µmol/ml

HA-AM-SUC unit: y µmol/ml (the unit wherein AM was treated with succinic anhydride)

Molecular weight of HA-AM-SUC unit: $M_1$ g/mol

Molecular weight of HA-AM-FITC unit: $M_2$ g/mol

Based on the above definitions, the percentage was calculated according to the following formulas:

[Formula 12]

$$(401.3 \times x) + (M_1 \times y) + (M_2 \times (\text{FITC conc.})) = 250 \text{ mg} \quad \text{Equation 1:}$$

$$x/(y + (\text{FITC conc.})) = (100 - \text{AM}(\%))/\text{AM}(\%) \quad \text{Equation 2:}$$

It is to be noted that in the above formulas, FITC conc. means the molar concentration of a unit having an FITC group. In addition, calculation was carried out based on DETA: $M_1=586.5$, $M_2=853.9$, DAHP: $M_1=573.5$, $M_2=840.8$, DAP: $M_1=557.5$, and $M_2=824.8$.

The obtained results are summarized in Table 9.

TABLE 9

FITC-labeled modified HAs used in pharmacokinetic studies

| Introduced compound AM | AM (%) NMR | HA-AM-FITC unit (mole %) | HA-AM-SUC unit (mole %) | Unmodified HA unit (mole %) | HA (weight %) |
|---|---|---|---|---|---|
| DETA | 89.8 | 0.9 | 88.9 | 10.2 | 67.4 |
| DAP | 93.2 | 0.9 | 92.3 | 6.8 | 70.0 |
| DAHP | 99.0 | 0.8 | 98.2 | 1.0 | 66.9 |

Example 7-2

Evaluation of Residence Time in Blood

HA-Administered Rat Plasma Sample

The fluorescein-labeled modified HA of Example 7-1 was administered in a dosage of 10 mg/kg into the vein of a rat as a single dose. The blood was collected (heparin treatment) before administration and 0.5, 2, 4, 8, 24, 48, 72, 96, and 168 hours after administration. Thereafter, plasma was obtained by centrifugation. This plasma sample was cryopreserved at −20° C. or lower until the measurement was carried out.

Measurement Method

A standard sample used for calibration curve and a measurement sample were dispensed into a 96-well plate, and they were analyzed using a microplate reader. Conditions for measurement are described below:

Microplate reader: SPECTRA MAX GEMINI (manufactured by Molecular Devices)

Sample volume: 100 µl/well

Detection: Fluorescence (EX: 485 nm, EM: 538 nm)

Preparation of Measurement Sample

Sample Used for Calibration Curve

Each fluorescein-labeled modified HA was diluted with PBS (pH 7.4), so as to prepare standard solutions having concentrations of 1, 5, 10, 50, 100, 500 µg/ml and 0 µg/ml (control, PBS (pH 7.4)). Thereafter, an equal volume of normal rat plasma was added to each standard solution, so as to prepare a sample used for calibration curve.

Preparation of Measurement Sample

An equal volume of PBS (pH 7.4) was added to a modified HA-administered rat plasma sample, so as to prepare a measurement sample.

Calculation of Concentration of Modified HA in Plasma

The concentration of the modified HA in plasma was calculated based on the calibration curve obtained from the fluorescence intensity of each standard sample using analysis software SOFTmax PRO (manufactured by Molecular Devices).

Pharmacokinetic Data

Figure 19:
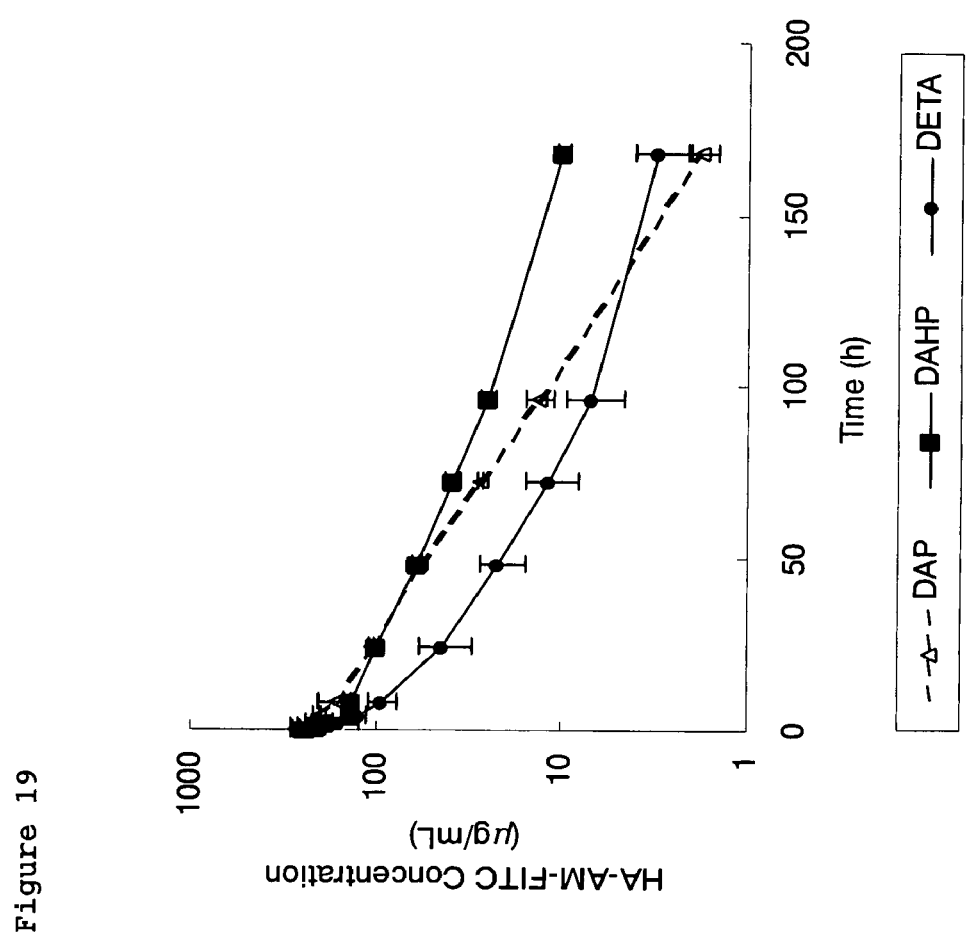
FIG. 19 is a view showing changes in the blood concentrations of fluorescein-labeled modified HAs having different substituents on substituted amide groups, which have been synthesized from HA having a molecular weight of 200 kDa.

With regard to data of changes in the concentrations in blood of the fluorescein-labeled modified HAs of Example 7-1, pharmacokinetic parameters were calculated using WinNonlin Ver 4.0.1 (manufactured by Pharsight). With regard to a change in the concentration in plasma of each individual, model-independent analysis was carried out, so as to calculate the mean residence time in blood (MRT). The half-life (t1/2) was calculated using the data of the final 3 measurable points of each individual. Such a change in the concentration in blood of the fluorescein-labeled modified HA is shown in FIG. 19. Moreover, the calculated pharmacokinetic parameters are shown in Table 10.

TABLE 10

Pharmacokinetic parameters of FITC-labeled modified HAs

| Introduced compound (AM) | Cl (mL/hr/kg) | MRT (h) | t½ |
|---|---|---|---|
| DETA | 2.5 | 45.0 | 51.5 |
| DAP | 1.3 | 34.8 | 24.5 |
| DAHP | 1.1 | 62.8 | 50.1 |

As in the case of modification of hyaluronic acid derivatives shown in FIG. 5, it was suggested that an increase in MRT, that is, extension of the retention ability in blood, occurs. Also, in the case of modification with various amino group-containing compounds, it has MRT of 18 hours or longer. Thus, it became clear that an amino group-containing compound can be changed depending on intended use.

Example 8

Synthesis of Methacryloyl Group-Introduced Modified HA

A modified HA having a methacryloyl group was synthesized to use as a substrate for preparing gel.

Example 8-1

Synthesis of HA-AEMA

DOWEX 50WX8-400 (manufactured by Sigma-Aldrich), which had been converted to tetrabutylammonium (TBA) salts using tetrabutyl hydroxide (manufactured by Sigma-Aldrich), were used to convert hyaluronic acid sodium salt having a molecular weight of 200 kDa (HA; manufactured by Denki Kagaku Kogyo Kabushiki Kaisha) to TBA salts. Thereafter, two solutions were prepared by dissolving the obtained hyaluronic acid tetrabutylammonium salt (HA-TBA) in DMSO (manufactured by Wako Pure Chemical Industries, Ltd.), resulting in a concentration of 2.0 mg/ml. Based on an equivalent ratio of HA unit/BOP (manufactured by Wako Pure Chemical Industries, Ltd.)/aminoethyl methacrylate (AEMA; manufactured by Sigma-Aldrich)=1/2.5/50 (mot/mol/mol), and also an equivalent ratio of 1/0.5/50 (mol/mol/mol), AEMA and BOP were added in this order to each solution, and the obtained mixture was reacted at room temperature overnight. Thereafter, a 1 M NaCl aqueous solution was added thereto in an amount that was half the volume of the reaction mixture, and 5N HCl solution was then added to the mixture to decrease the pH to pH 3. Furthermore, the resultant was neutralized with 2N NaOH solution. Thereafter, the resultant was dialyzed against large excess amount of 0.3 M NaCl aqueous solution and then to distilled water (Milli Q water) for purification (Spectrapore 4; molecular weight cut off (MWCO): 12 k-14 kDa). Thereafter, the resultant was freeze-dried, so as to obtain the captioned hyaluronic acid into which a methacryloyl group had been introduced (HA-AEMA).

Figure 20:
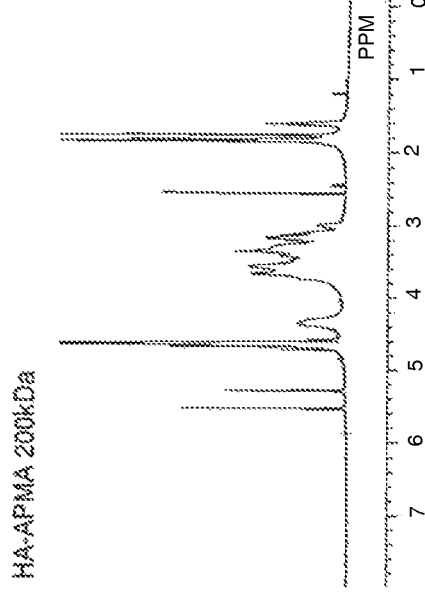
FIG. 20 shows an example of the $^1$H-NMR spectra of the AEMA group-introduced modified hyaluronic acid of the present invention.

The AEMA introduction ratio in the obtained HA-AEMA was quantified by the $^1$H-NMR method. As a result, it was found that 56.5% (BOP: 2.5 times equivalent) and 38.0% (BOP: 0.5 times equivalent) had been converted to AEMA, respectively (N-acetyl groups of HA and HA-AEMA, (1.9 to 2.1 ppm) (3H), were compared with methacryloyl group-derived portion of HA-AEMA, 5.5 to 6.1 ppm (each 2H); refer to FIG. 20).

Example 8-2

Synthesis of HA-APMA

Using aminopropylmethacrylamide (APMA; manufactured by PolyScience) instead of AEMA, reaction was carried out at an equivalent ratio of HA unit/BOP (Wako Pure Chemical Industries, Ltd.)/APMA=1/2.0/5 (mol/mot/mol). The same method as that described in Example 8-1 was applied with the aforementioned exception, so as to obtain HA-APMA.

Figure 21:
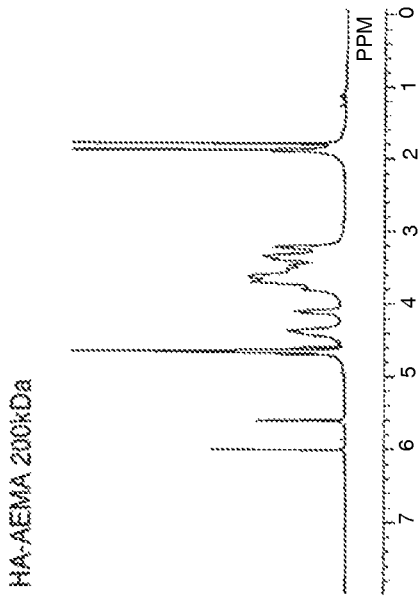
FIG. 21 shows an example of the $^1$H-NMR spectra of the APMA group-introduced modified hyaluronic acid of the present invention.

The APMA introduction ratio in the obtained HA-APMA was quantified by the $^1$H-NMR method. As a result, it was found that 47.5% had been converted to APMA (N-acetyl groups of HA and HA-APMA, (1.9 to 2.1 ppm) (3H), were compared with methacryloyl group-derived portion of HA-APMA, 5.2 to 5.8 ppm (each 2H); refer to FIG. 21).

Example 9

Control of Introduction of Methacryloyl Group Depending on Additive Amount of BOP In order to control of the introduction ratio of a methacryloyl group, a condensing agent was added at various ratios, so as to conduct synthesis. Thereafter, the introduction rates were analyzed.

5.0 mg/ml HA (200 kDa)-TBA (for AEMA) or 4.0 mg/ml HA (200 kDa)-TBA (for APMA) was dissolved in DMSO, so as to prepare a solution. AEMA or APMA was added thereto at an equivalent ratio of HA unit/AEMA (manufactured by PolyScience) or APMA (manufactured by PolyScience)=1/5 (mol/mol). Thereafter, a BOP reagent was added thereto at an equivalent ratio of 0.2, 0.25, 0.4, or 1.0 to the HA unit, and the obtained mixture was reacted overnight. Thereafter, a 1 M NaCl aqueous solution was added thereto in an amount that was half the volume of the reaction mixture, and 5N HCl solution was then added to the mixture to decrease the pH to pH 3. Furthermore, the resultant was neutralized with 2N NaOH solution. Thereafter, the resultant was dialyzed against large excess amount of 0.3 M NaCl aqueous solution, and then was dialyzed against large excess amount of distilled water (Milli Q water) for purification (Spectrapore 4; molecular weight cut off (MWCO): 12 k-14 kDa), followed by freeze-drying.

Figure 22:
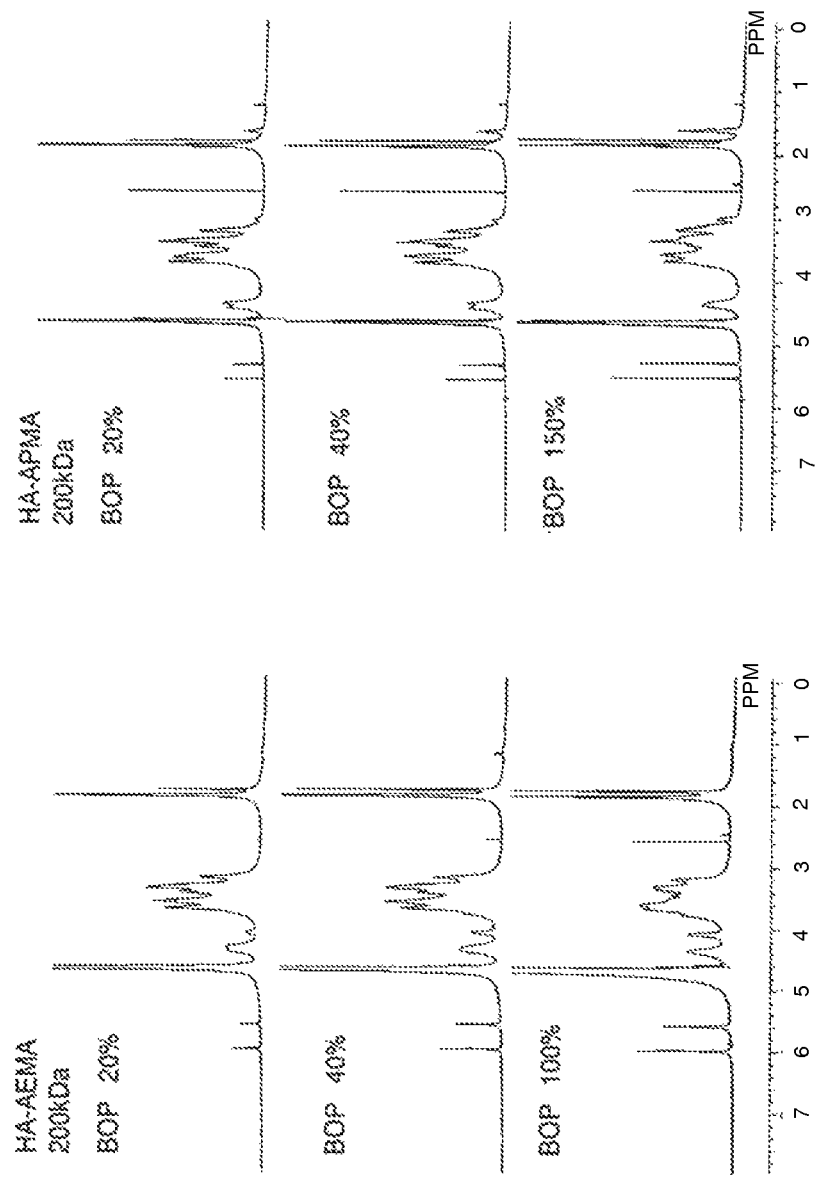
FIG. 22 shows an example of the $^1$H-NMR spectra of the methacryloyl group-introduced modified hyaluronic acid of the present invention.

The methacryloyl group introduction ratio was quantified by the $^1$H-NMR method (HA: methyl proton of N-acetyl group, 1.8 to 1.9 ppm, MA: methacryloyl group-derived, 5.5 to 6.1 ppm (AEMA), 5.2 to 5.8 ppm (APMA)). The $^1$H-NMR spectra are shown in FIG. 22. The methacryloyl group introduction ratio is shown in Table 11. It was found that the methacryloyl group introduction ratio can be controlled by addition of BOP.

TABLE 11

Relationship between additive amount of BOP and methacryloyl group introduction ratio

| Substituent | HA:Condensing agent | Introduction ratio (%) (NMR) |
| --- | --- | --- |
| AEMA | 100:20 | 9.7 |
|  | 100:25 | 11.0 |
|  | 100:40 | 19.0 |
|  | 100:100 | 48.0 |
| APMA | 100:20 | 9.0 |
|  | 100:40 | 12.0 |
|  | 100:100 | 45.0 |

Example 10

Synthesis of Fluorescein-Labeled HA-HZ

In order to use as a gel-encapsulated sample, fluorescein-labeled HA-HZ was synthesized.

Example 10-1

Synthesis of HA-HZ

Hyaluronic acid having a molecular weight of 200 kDa (HA; manufactured by Denki Kagaku Kogyo Kabushiki Kaisha) was dissolved in a concentration of 0.5% in distilled water (Milli Q water), and 5N hydrochloric acid solution was added thereto to adjust pH to 4.7 to 4.8. Thereafter, 1-ethyl-3-(3-dimethylaminopropyl)carbodiimide (EDC) and adipic acid dihydrazide (ADH) were added thereto, resulting in a molar ratio of HA unit: EDC: ADH=1:0.05:40 (mol/mol/ mol). Thereafter, while maintaining the pH at pH 4.7 to 4.8 by addition of 5N hydrochloric acid solution, the obtained mixture was reacted under stirring at room temperature for 2 hours. Thereafter, the reaction solution was dialyzed against 100 mM sodium chloride solution, 25% ethanol aqueous solution, and distilled water (Milli Q water) for purification (Spectrapore 4; molecular weight cut off (MWCO): 12 k-14 kDa), followed by freeze-drying, so as to obtain hyaluronic acid into which a hydrazide group had been introduced (HA-HZ).

The HZ introduction ratio in the obtained HA-HZ was quantified by the $^1$H-NMR method. As a result, it was found that 3.75% of carboxylic acid of each HA was converted to HZ (N-acetyl groups of HA and HA-HZ, 2.1 ppm (3H), were compared with methylene groups of adipic acid-derived portion of HA-HZ, 1.7 ppm, 2.4 ppm (each 2H)).

Example 10-2

Synthesis of Fluorescein-Labeled HA-HZ

The HA-HZ as obtained above (Example 10-1) was dissolved in distilled water (Milli Q water), resulting in a concentration of 20.0 mg/ml. Thereafter, a 0.25 M carbonate buffer (pH 9.0; 4.84 ml) and a DMSO solution (2.42 ml) that contained 101.3 mg/ml FITC were added to the above obtained solution, and the obtained mixture was gently shaken in the dark at room temperature for 1 hour. Thereafter, the resultant was dialyzed against an excessive amount of PBS for purification. The external dialysis solution was exchanged with distilled water (Milli Q water), followed by further dialysis and purification (Spectrapore 4; molecular weight cut off (MWCO): 12 k-14 kDa). The obtained aqueous solution was freeze-dried, so as to obtain fluorescein-labeled HA-HZ (227.63 mg).

Example 11

Preparation of Fluorescein-Labeled HA-AM-SUC-Encapsulated HA-AEMA Cross-Linked Gel Using a methacryloyl group-introduced modified HA, a bulk-state gel in which fluorescein-labeled HA-HZ had been encapsulated was prepared via a Michael addition reaction involving a methacryloyl group and a mercapto group. Thereafter, the sustained-release property of the gel was evaluated.

3.97 mg of the HA-AEMA having an AEMA introduction ratio of 56.5% obtained in Example 8-1 and the fluorescein-labeled HA-HZ (107 µg) obtained in Example 10-2 were dissolved in distilled water (Milli Q water; 60 µl). Thereafter, triethanolamine (TEA, 1.3 µl) and a dithiothreitol (DTT) solution (9.25 mg/ml, 200 mM phosphate buffer (pH 8.3), 40 µl) were added. The mixture was reacted in the dark at 37° C. for 1 hour, so as to obtain gel.

The same synthesis as that described in Example 9 was carried out with the exceptions that a BOP reagent was added at an equivalent ratio of 0.4 to an HA unit, and that the mixture was then reacted overnight, thereby obtaining HA-AEMA having an introduction ratio of 18.8%. 3.92 mg of the obtained HA-AEMA and the fluorescein-labeled HA-AM-SUC (410 µg) obtained in Example 5-2 were dissolved in distilled water (Milli Q water, 60 µl). Thereafter, dithiothreitol (DTT) solution (9.25 mg/ml, 200 mM phosphate buffer (pH 8.3), 40 µl) was added to the above obtained solution. The mixture was reacted in the dark at 37° C. for 1 hour, so as to obtain gel (HA-AEMA 4% gel). Herein, the term "HA-AEMA 4% gel" is used to mean a gel that contains 4 mg of HA-AEMA in 100 µl of water.

Comparative Example 11-1

Synthesis of Gel Substrate Used as Control (HA-HZ-SH) and Preparation of Gel

HA-HZ (369.81 mg) having an HZ introduction ratio of 26.0%, which had been synthesized at an molar ratio of HA unit/EDC/ADH=1/0.2/40 (mol/mol/mol) by the same method as that described in Example 10-1, was dissolved in distilled water (Milli Q water), resulting in 20.0 mg/ml. Thereafter, 2-iminothiolane hydrochloride (ITL; manufactured by Pierce) was dissolved in a 200 mM phosphate buffer (pH 8.3), resulting in a molar ratio of HZ/ITL=1/2, and the obtained solution was then added to the above solution. The obtained mixture was reacted at room temperature for 2 hours, while stirring. The reaction solution was precipitated in ethanol, and was then washed 3 times. Thereafter, the resultant was dried, so as to obtain hyaluronic acid into which a mercapto group had been introduced (HA-HZ-SH, 321.68 mg). The SH group introduction ratio in the obtained HA-HZ-SH was quantified by the $^1$H-NMR method. As a result, it was found that 22.0% of carboxylic acid of HA was converted to SH(N-acetyl groups of HA and HA-HZ-SH (1.9 ppm, 3H) were compared with methylene groups of ITL-derived portion of HA-HZ-SH (2.1 ppm and 2.7 ppm, each 2H)). Subsequently, with regard to the thus synthesized HA-HZ-SH, 1.99 mg (HA-HZ-SH 2% gel) and 4.08 mg (HA-HZ-SH 4% gel), and 98.1 and 105 µl of fluorescein-labeled HA-HZ of Example 10-2, were dissolved in distilled water (Milli Q water, 60.1). Thereafter, an STT solution (200 mM phosphate buffer (pH 8.3), 40 µl) was added to the above solution, resulting in a molar ratio of sodium tetrathionate dihydrate (hereinafter also referred to as "STT")/SH=0.1/1. The obtained mixture was then reacted in the dark at 37° C. for 1 hour, so as to obtain a gel. Herein, the term "HA-HZ-SH 2% gel" is used to mean a gel that contains 2 mg of HA-HZ-SH in 100 µl of water. The term "HA-HZ-SH 4% gel" is used to mean a gel that contains 4 mg of HA-HZ-SH in HA-HZ-SH 2% gel.

Comparative Example 11-2

Synthesis Of Gel Substrate Used as Control (HA-HZ-MA) and Preparation of Gel

A gel substrate was synthesized in the same manner as that in Example 10-1 with the exception that a molar ratio of HA/EDC/ADH=1/5/40 (mol/mol/mol) was applied, so as to obtain HA-HZ wherein 63% of carboxylic acid of HA had been converted to HZ. Subsequently, the obtained HA-HZ (207.46 mg) was dissolved in distilled water (Milli Q water, 9 ml), and a 1 M phosphate buffer (pH 8.8) was then added thereto, so as to adjust an HA concentration to be 20 mg/ml. Methacrylic anhydride was added dropwise thereto in an amount of 20 times the equivalent of HZ, and the obtained mixture was then reacted at room temperature for 4 hour. The resultant was precipitated in tetrahydrofuran, and was then recovered, followed by drying. The precipitate was dissolved in distilled water (Milli Q water), and was then precipitated in tetrahydrofuran again, followed by drying. Thereafter, the dry product was dissolved in distilled water (Milli Q water), followed by freeze-drying, so as to obtain HA-HZ-MA. The MA group introduction ratio in the obtained HA-HZ-MA was quantified by the $^1$H-NMR method. As a result, it was found that 17.0% of carboxylic acid of HA was converted to MA (HA: methyl proton of N-acetyl groups (1.8 to 1.9 ppm) was compared with MA: $CH_2$ of methacryloyl groups=(5.5 to 6.1 ppm)). Subsequently, 4.07 mg of the thus synthesized HA-HZ-MA (HA-HZ-MA 4% gel) and 99 µg of the fluorescein-labeled HA-HZ obtained in Example 10-2 were dissolved in distilled water (Milli Q water, 60 µl). Thereafter, triethanolamine (TEA, 1.3 µl) and a DTT solution (2.71 mg/ml, 200 mM phosphate buffer (pH 8.3), 40 µl) were added to the above solution. The obtained mixture was then reacted in the dark at 37° C. overnight, so as to obtain a gel.

Test Example 2

Figure 23:
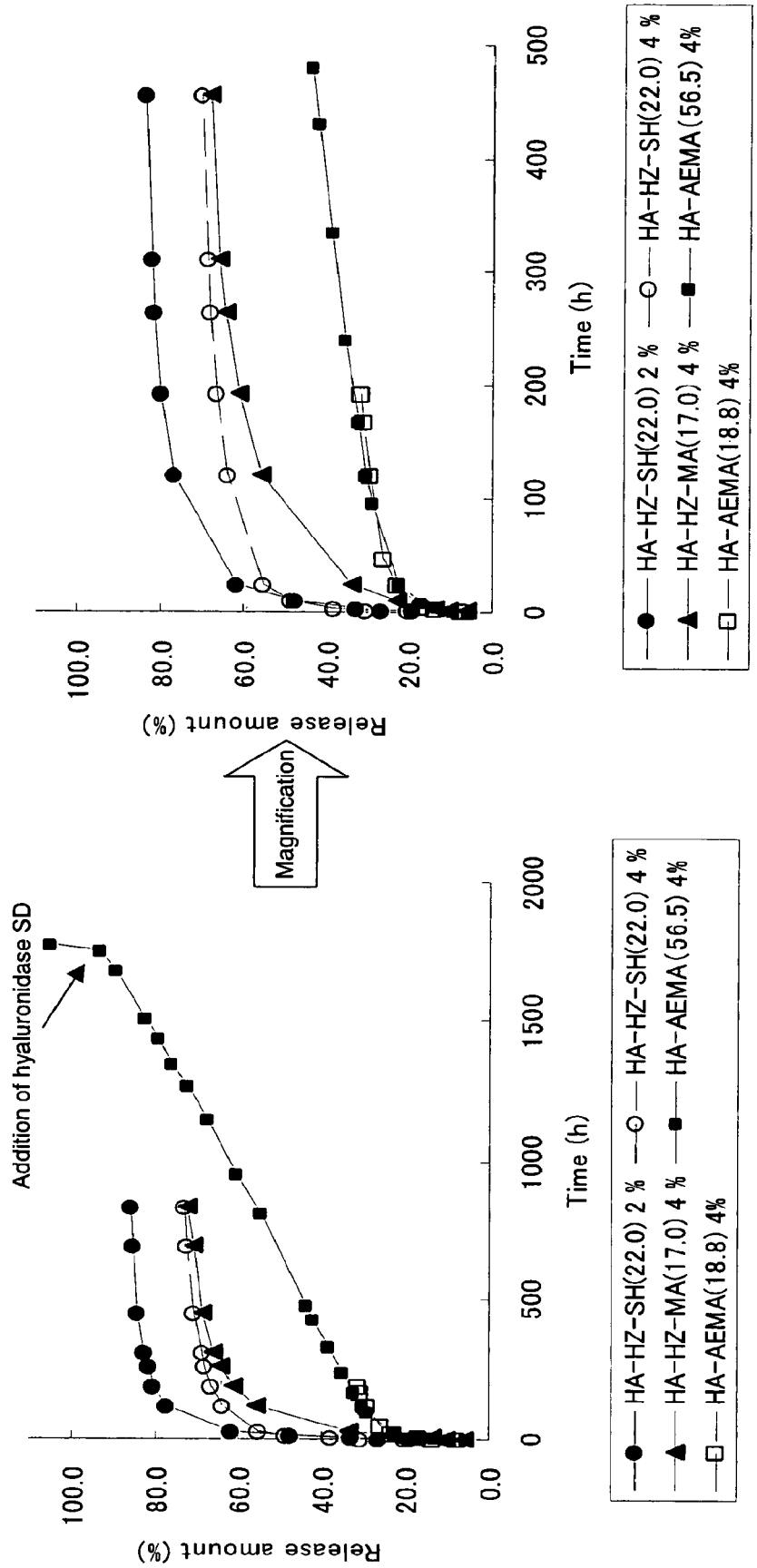
FIG. 23 is a view showing the release of fluorescein-labeled HA-HZ from HA gel.

Evaluation of Sustained-Release Performance of Fluorescein-Labeled HA-AM-SUC from HA-AEMA Cross-Linked Gel Each of the gels obtained in Example 11, Comparative Example 11-1, and Comparative Example 11-2 was incubated in 1 ml of PBS at 37° C., and the total amount was subjected to sampling over time. Fluorescein-labeled HA-HZ released in the buffer was quantified by GPC. Measurement conditions for GPC are described below. The releasing performance of the fluorescein-labeled HA-HZ from the gel obtained when the fluorescein-labeled HA-HZ encapsulated in the gel is defined as 100% is shown in FIG. 23. The gels obtained in Comparative Examples 11-1 and 11-2 were sampled for 5 weeks. With regard to the HA-AEMA gel obtained in Example 11, 0.25 U of hyaluronidase was added thereto approximately 10 weeks later for decomposition, so that all the encapsulated products were released.

GPC Column: TSKgel G6000PWxr, (manufactured by TOSOH)
Mobile phase: PBS (pH 7.4)
Elution mode: Isocratic
Flow ratio: 1 ml/min
Injection volume: 25 µl
Detection: UV (494 nm)

FIG. 23 suggests that gel prepared from HA-AEMA is not relative to the introduction ratio of AEMA, that its releasing behavior does not significantly change, and that the reacting functional groups, which are approximately 18.8%, have the same releasing profile, thereby enabling a sufficiently long-term sustained-release. In addition, it has also been clarified that when compared with the gel formed due to a disulfide formation (Comparative Example 11-1), the gel prepared from HA-AEMA of the present invention enables an extremely long-term sustained-release. Moreover, even when compared with HA-HZ-MA (Comparative Example 11-2) into which a methacrylic acid had been directly introduced via an amide bond, the gel of the present invention also enables a long-term sustained-release. It is considered that this is because of a difference in reactivity caused by the bonding manner of a methacryloyl group, the uniformity of modifying functional groups, or the like. Using the modified HA of AEMA having a methacrylic acid bonding manner due to an ester, it became possible to prepare a gel that enables a longer sustained-release.

Example 12

Preparation of Fluorescein-Labeled HA-HZ Encapsulated HA-AEMA Cross-Linked Gel Particles Using a Spray Dryer An injectable microgel was prepared from HA-AEMA using a spray dryer.

Figure 24:
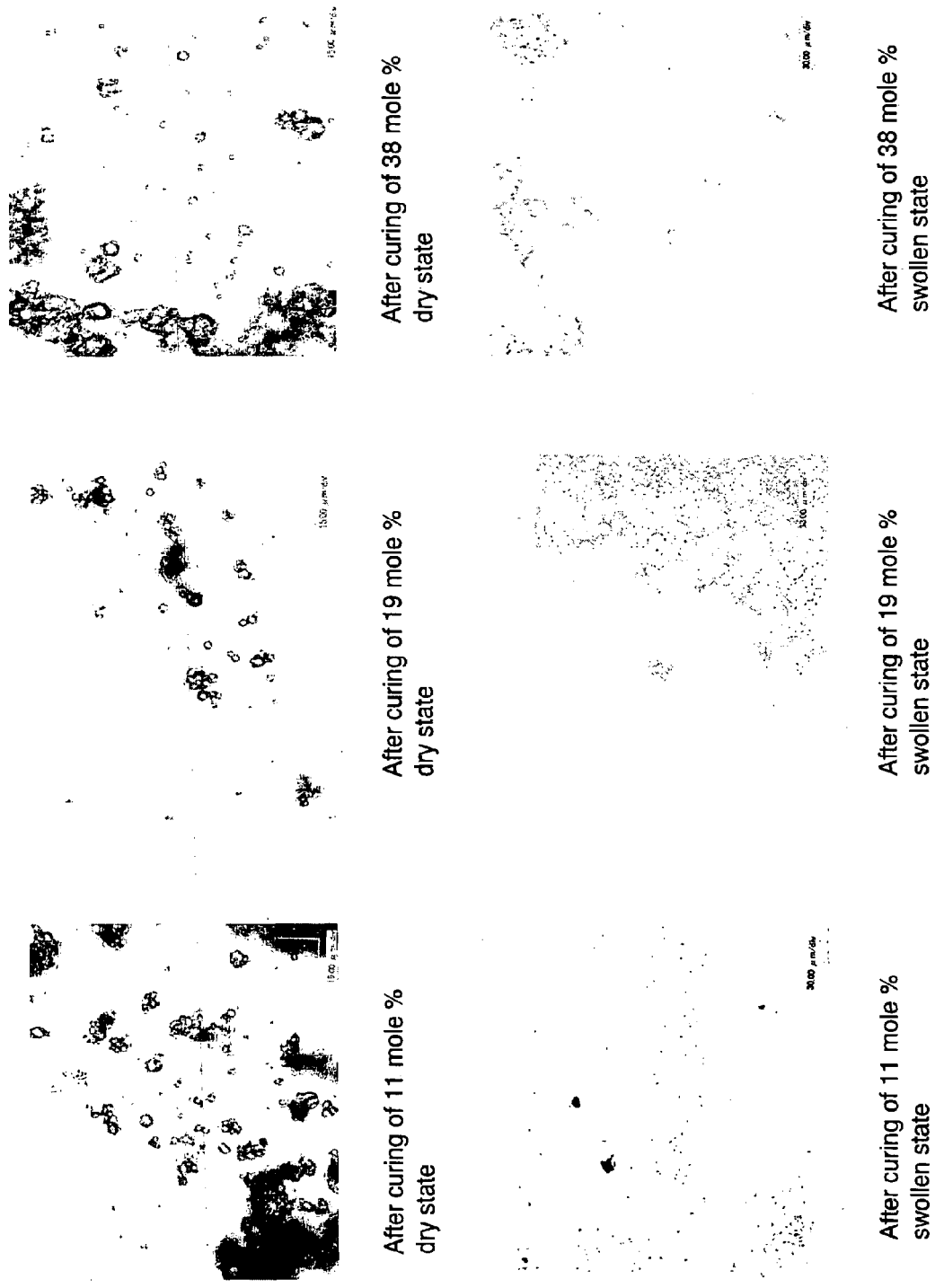
FIG. 24 shows an example of the photomicrograph of an HA-AEMA cross-linked gel particle, in which fluorescein-labeled HA-HZ has been encapsulated.

50 mg each of the HA-AEMA having an AEMA group introduction ratio of 11 mole %, 19 mole %, or 38 mole %, which were obtained in Examples 9 and 8-1, and 5 mg of the fluorescein-labeled HA-HZ obtained in Example 10-2, were dissolved in distilled water (Milli Q water, 5 ml) (overnight). Thereafter, a DTT solution (200 mM phosphate buffer (pH 8.3), 250 µl) was added to the above obtained solution, resulting in a molar ratio of AEMA/SH=1/1. Thereafter, spray drying was carried out under the conditions as described below, so as to obtain particles. The particle size of the obtained particles were between 1 and 3 µm. The particles of each sample were placed on a preparation. Thereafter, the dry state and a state where PBS (pH 7.4) had been added to swell it were observed under a microscope. The photomicrographs are shown in FIG. 24. Particles having an AEMA group introduction ratio of 11 mole % or 19 mole % when PBS had been added, were dissolved. These particles were cured in a 50° C. thermostatic bath (manufactured by Yamato Kagaku; DN-42), and sampling was carried out 72 hours later. There particles were placed on a preparation, PBS of pH 7.4 was then added thereto, and the particle state was then observed under a microscope. As a result, it was found that particles were not dissolved in PBS. The aforementioned operations were carried out, so as to obtain fluorescein-labeled HA-HZ encapsulated HA-AEMA cross-linked gel particles having AEMA group introduction rates of 11 mole %, 19 mole %, and 38 mole % (refer to FIG. 24).

Spray Dry Conditions
Spray dryer: manufactured by Buchi, Mini Spray Dryer B-191
Solution feed ratio: 0.5 ml/min (Tygon tube, Pump speed=15%)
Feed solution conc.: 10 mg/ml
Atomizing air flow ratio: 650 L/hr
Drying air flow ratio: 40 kL/hr (Aspiration speed=100%)
Inlet temp.: 90° C.
Outlet temp.: 55° C. to 65° C.

Example 13

Preparation of Fluorescein-Labeled HA-AM Encapsulated HA-AEMA Cross-Linked Gel Particles by Frost Shattering An injectable microgel was prepared from HA-AEMA by the frost shattering method.

Figure 25:
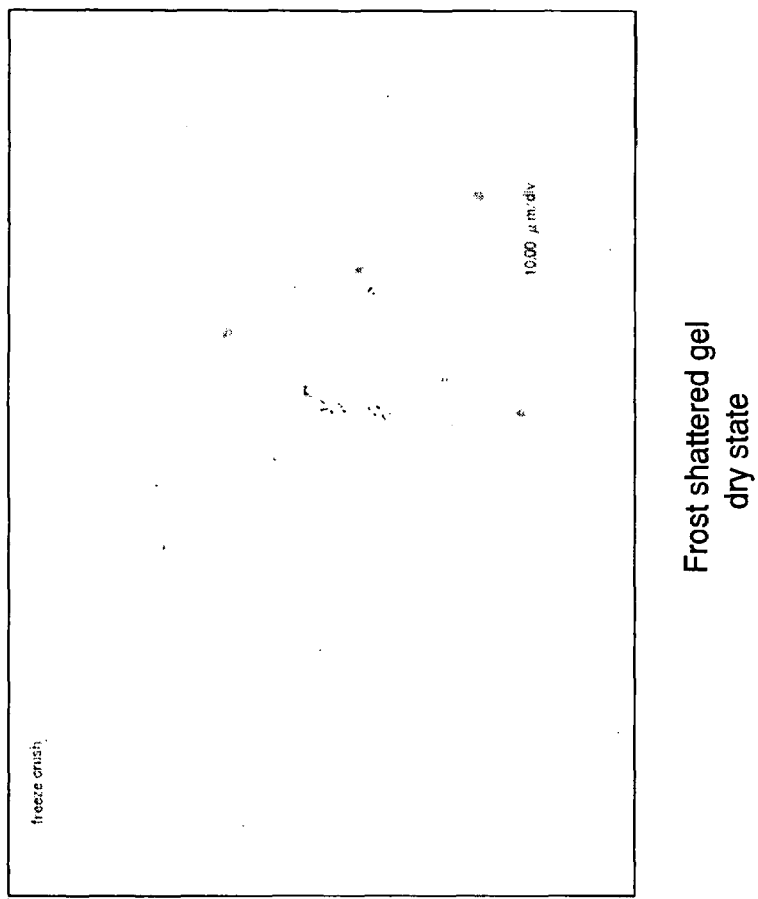
FIG. 25 shows an example of the photomicrograph of an HA-AEMA cross-linked gel particle, in which fluorescein-labeled HA-AMSUC has been encapsulated.

4 mg of the HA-AEMA having an AEMA group introduction ratio of 19 mole % obtained in Example 9 and 0.4 mg of the fluorescein-labeled HA-AM-SUC obtained in Example 5-2 were dissolved in distilled water (Milli Q water, 50 µl) (overnight). Thereafter, a DTT solution (200 mM phosphate buffer (pH 8.3), 50 µl) was added to the above obtained solution, resulting in a molar ratio of AEMA/SH=1/1. Thereafter, the obtained mixture was reacted under light shielding conditions at 37° C. for 1 hour, so as to obtain a gel. This gel was dried in a 37° C. thermostatic bath (manufactured by Yamato Kagaku; Incubator IS42), so as to obtain a fluorescein-labeled HA-AM-SUC encapsulated HA-AEMA cross-linked dry gel (hereinafter also referred to as "dry gel"). The thus obtained dry gel was further freezed with liquid nitrogen, and it was then crushed with an SK mill (manufactured by Tokken Inc., SK-100) repeatedly. The aforementioned operations were carried out, so as to obtain fluorescein-labeled HA-AM-SUC encapsulated HA-AEMA cross-linked frost shattered gel particles (hereinafter also referred to as "frost shattered gel"). The particles of each sample were placed on a preparation, and the dry state was then observed under a microscope. The photomicrographs are shown in FIG. 25. The particle size of the obtained frost shattered gel was between 2 and 6 p.m.

Test Example 3

Evaluation of Sustained-Release Performance of Fluorescein-Labeled HA-AM from HA-AEMA Cross-Linked Gel Each of the dry gel and frost shattered gel obtained in Example 13 was incubated in 1 ml of PBS at 37° C., and 200 µl thereof was subjected to sampling over time. Fluorescein-labeled HA-AM-SUC released in a buffer was quantified by GPC. Measurement conditions for GPC are the same as those described in Test Example 2. The releasing performance of the fluorescein-labeled HA-AM-SUC from the gel obtained when the fluorescein-labeled HA-AM-SUC encapsulated in the gel is defined as 100% is shown in FIG. 26.

Figure 26:
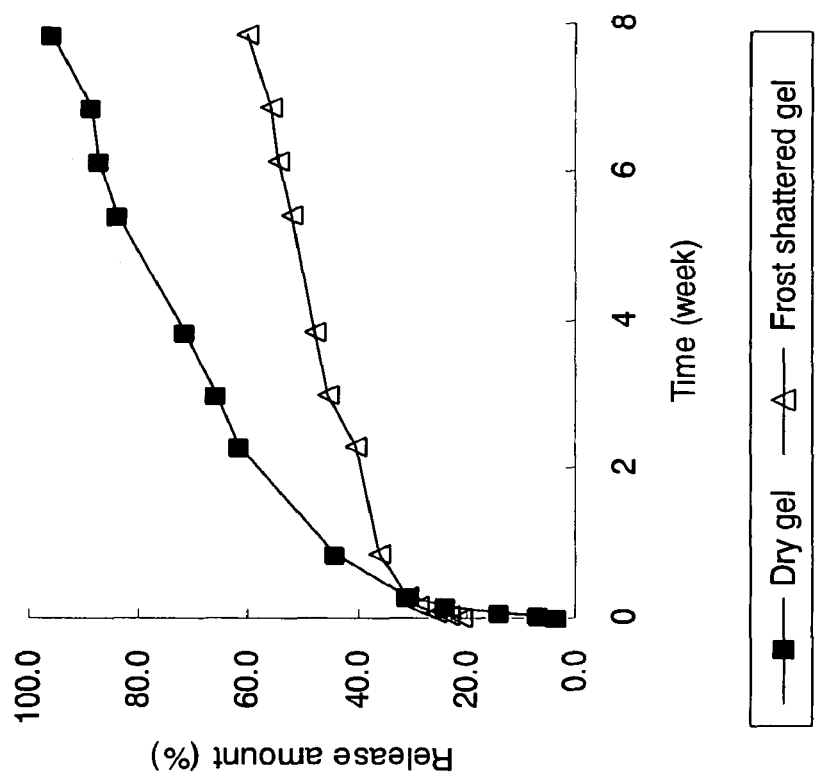
FIG. 26 is a view showing the release of fluorescein-labeled HA-AM-SUC from HA gel.

From FIG. 26, it became clear that the dry gel of the present invention enables a long-term sustained-release. In addition, it also became clear that when compared with the dry gel, the frost shattered gel tends to have a large initial burst due to an increase in the surface area due to microparticulation, but that it enables a sufficiently long-term sustained-release. Thus, it was clarified that a microgel capable of a long-term sustained-release can be prepared from injectable particles.

Example 14

Preparation of Water-Soluble Modified HA-Fab Conjugate and Fab

Example 14-1

Preparation of IgG Fab

PBS (1.445 ml) was added to an IgG solution (54.0 mg/ml, 0.85 ml) dissolved in a phosphate buffer, so as to dilute the above solution. 0.5 ml of the thus diluted solution was subjected to an IgG Fab preparation kit (ImmunoPure (registered trademark) Fab Preparation kit, which contains Papain as a digestive enzyme; manufactured by Pierce), and operations were carried out in accordance with instruction included therewith, so as to obtain a non-adsorbed fraction from a Protein A column (included in the preparation kit). It is to be noted that digestion with Papain was carried out at 37° C. for 15 hours. The obtained solution was concentrated using a centrifugal ultrafilter (Amicon Ultra-4; manufactured by Amicon), and the obtained concentrate was diluted again with PBS, so as to finally obtain approximately 1.5 ml of a solution. The operations ranging from the operation with the IgG Fab preparation kit to concentration were carried out 4 times in total under the same conditions. Solutions obtained from 4 times of preparation were mixed together, so as to obtain approximately 11.8 mg of IgG Fab (hereinafter also referred to as "Fab") (1.96 mg/ml, 6.0 ml). It is to be noted that the concentration of Fab was quantified by an ultraviolet-visible absorbance measurement method.

Example 14-2

FITC Labeling of Fab 5 ml of the Fab PBS solution (1.96 mg/ml, 6.0 ml) obtained in Example 14-1 was subjected to solvent exchange with a 50 mM carbonate buffer containing 150 mM NaCl and 10 mM EDTA (pH 9.5; hereinafter also referred to as a "FITC buffer") (7 ml) by using a desalting column (PD-10, manufactured by Amersham Biosciences). The resultant was concentrated to approximately 5 ml by centrifugal ultrafiltration (Centricon-30; manufactured by Amicon). Thereafter, a 1% DMSO-containing FITC buffer (342 µl) including an FITC concentration of 2 mg/ml was added to 4.78 ml of the resultant solution. The obtained mixture was reacted at room temperature in the dark for 2 hours. The reaction solution was dialyzed against 1 L of PBS at 4° C. under light shielding conditions for purification (Slide-A-Lyzer MWCO: 10000; manufactured by Pierce). The total amount of the external dialysis solution was exchanged with a fresh solution 2, 4, 6, and 15 hours later, followed by a further dialysis at room temperature in the dark for 2 hours. Thereafter, an FITC-labeled Fab solution was recovered. The recovered solution was subjected to solvent exchange with an FITC buffer by using a desalting column, and it was then concentrated to approximately 4.5 ml by centrifugal ultrafiltration (Centricon-30), so as to obtain an FITC buffer solution of FITC-labeled Fab.

Example 14-3

Preparation of FITC-Labeled Fab Solution Used in Pharmacokinetics (PK) Studies

Approximately 1.75 ml out of approximately 4.5 ml of the FITC-labeled Fab FITC buffer solution obtained in Example 14-2 was subjected to solvent exchange with PBS (3.5 ml) by using a desalting column (PD-10). The obtained solution was concentrated to approximately 0.5 ml by centrifugal ultrafiltration (Centricon-30), so as to obtain an FITC-labeled Fab solution used in PK studies. 2.5 µl of the obtained solution was 40 times diluted with PBS, and absorbance at 280 and 495 nm was then measured. The Fab concentration and the ratio of FITC/Fab were calculated by the following two formulas. As a result, it was found that Fab: 5.97 mg/ml and that FITC/Fab: 3.24 (mol/mol).

[Formula 13]

Fab (mg/mL)={(Abs. at 280 nm)−0.35×(Abs. at 495 nm)}/1.48   Equation 1:

FITC/Fab (mol/mol)=1.01×(Abs. at 495 nm)/{(Abs. at 280 nm)−(0.35×(Abs. at 495 nm))}   Equation 2:

Example 14-4

Preparation of FITC-Labeled Fab into which Mercapto Group has been Introduced (FITC-Labeled Fab-SH)

A 2-iminothiolane hydrochloride (2-Iminothiolane.HCl; ITL; manufactured by Pierce) FITC buffer solution (2 mg/ml, 283 µl) was added to 2.75 ml out of approximately 4.5 ml of the FITC-labeled Fab solution obtained in Example 14-2, and the obtained mixture was reacted at room temperature in the dark for 30 minutes. Thereafter, unreacted low-molecular-weight components were removed by using a desalting column (PD-10), and at the same time, the solvent was exchanged with 1 mM EDTA-containing PBS. The obtained solution was subjected to centrifugal ultrafiltration (Centricon-30), so as to concentrate it to approximately 1.2 ml, thereby obtaining an FITC-labeled Fab-SH solution. 2.5 µl out of the obtained FITC-labeled Fab-SH solution was 40 times diluted with PBS, and the absorbance at 280 and 495 nm was measured. As with Example 14-3, an Fab-SH concentration and the FITC/Fab-SH ratio were calculated. As a result, it was found that Fab-SH: 1.05 mg/ml, and FITC/Fab-SH: 3.20 (mol/mol). In addition, 15 µl was removed from the obtained solution, and mercapto groups were quantified using an Ellman's reagent. A mercapto group introduction ratio was calculated from mercapto groups and the Fab-SH concentration. As a result, it was found that mercapto group/Fab-SH: 1.97 (mol/mol). A method for quantifying mercapto groups using the Ellman's reagent will be described below.

Method for Quantifying Mercapto Groups Using Ellman's Reagent

[Reagent]

Reaction solvent: 1 mM EDTA-containing 0.1 M phosphate buffer (pH 8.0)

Ellman's reagent solution: DMSO solution containing 40 mg/ml Ellman's reagent that was 10 times diluted with reaction solvent

[Standard Substance]

A cysteine hydrochloride monohydrate (hereinafter also referred to as "Cys") was dissolved in the reaction solvent, so as to adjust it to 10.54 mg/ml (60 mM).

100 µl of the thus obtained solution was 10 times diluted with the reaction solvent, and 200 µl of the diluted solution was then 5 times diluted with the reaction solvent (final concentration of Cys: 1.2 mM).

From the 1.2 mM Cys solution, a 2-times diluted series was prepared (8 points of concentrations: 0.0094 to 1.2 mM).

[Quantification]

3 µl of the Ellman's reagent solution was added to 150 µl of the reaction solvent. The standard substance or 15 µl of a sample solution was added to the reaction solvent containing the Ellman's reagent, and the mixture was stirred and mixed. The resultant was incubated at room temperature for 15 minutes, and the absorbance at 412 nm was measured. A calibration curve was prepared from the absorbance of the standard substance and mercapto groups contained in the sample solution were quantified.

Example 14-5

Preparation of HA-AM-MI/SUC

An HA-AM (EDOBEA introduction ratio: 95.5%) aqueous solution (10 mg/ml, 8.5 ml) was obtained in the same manner as that in Example 3-1 with the exception that a BOP reagent was used at a ratio of 2.5 to an HA unit. Thereafter, a 0.2 M phosphate buffer (pH 7.0; 10.625 ml) was added to the obtained HA-AM aqueous solution. A DMSO solution (1.074 mg/ml, 2.125 ml) of N-[κ-Maleimidoundecanoyloxy]-sulfosuccinimide ester (Sulfo-KMUS; manufactured by Pierce) was added to the above solution, and the obtained mixture was then shaken at room temperature for 30 minutes. Thereafter, a succinic anhydride DMSO solution (283.95 mg/ml, 2.125 ml) was added to the reaction solution, and the obtained mixture was then further shaken at room temperature for 1.5 hours. Thereafter, the reaction solution was dialyzed against large excess amount of distilled water (Milli Q water) at 4° C. (Spectrapore 4; MWCO: 12 k-14 kDa) for purification. The obtained solution was freeze-dried, so as to obtain HA-AM-MI/SUC (98.15 mg).

Example 14-6

Preparation of HA-FITC-Labeled Fab Conjugate Solution Used in PK Studies 1.1 ml out of 1.2 ml of the FITC-labeled Fab-SH solution obtained in Example 14-4 and 1 mM EDTA-containing PBS (1.1 ml) were added to the HA-AM-MI/SUC aqueous solution (20 mg/ml, 2.2 ml) obtained in Example 14-5, and the obtained mixture was then incubated at 37° C. for 2 hours. A 1 mM EDTA-containing PBS solution of iodoacetic acid (55.8 g/ml, 1.1 ml) was added to the resultant, and the obtained mixture was then further incubated for 1 hour. The reaction mixture was subjected to GPC under the conditions as described below, so as to fractionate a conjugate fraction. GPC conditions are described below. A 1/10 volume of 10 mM glycine-containing PBS was added to the fractionated solution, and the obtained solution was concentrated to approximately 3.0 ml by centrifugal ultrafiltration (Vivaspin20; MWCO: 50000; manufactured by Funakoshi), so as to obtain an HA-FITC-labeled Fab conjugate solution. 10 µl was removed from the obtained HA-FITC-labeled Fab conjugate solution, and it was then 10 times diluted with PBS. Thereafter, the absorbance at 280 and 495 nm was measured. Using the ratio of (the absorbance at 495 nm)/(the absorbance at 280 nm) of FITC-labeled Fab-SH measured in Example 14-4, the Fab concentration was calculated. As a result, it was found that Fab: 1.05 mg/ml.

GPC Conditions

System: FPLC or AKTA explorer (both of which are manufactured by Amersham Biosciences)

GPC Column: HiLoad 16/60 Superdex 200prep grade (manufactured by Amersham Biosciences)

Mobile phase: PBS (pH 7.4)

Flow ratio: 1.0 ml/min

Detection: UV (280 nm)

Test Example 4

Change in concentration in plasma when HA-FITC-labeled Fab conjugate and FITC-labeled Fab are administered into vein of rat as single dose The HA-FITC-labeled Fab conjugate solution obtained in Example 14-6 and the FITC-labeled Fab solution used in PK studies obtained in Example 14-3 (both of which were diluted with 10 mM glycine-containing PBS to an Fab concentration of 1 mg/ml) were administered into the tail vein of male rats (slc: SD; Japan SLC Inc.) as a single dose of 3 mg/kg (n=3). 15 minutes, 30 minutes, and 1, 2, 4, 6, 8, and 24 hours after the administration, the blood was collected from neck vein, using a heparin-treated 25 G injection needle-attached Terumo syringe. In addition, with regard to an HA-FITC-labeled Fab conjugate administration group, 48, 72, 96, and 168 hours after the administration also, the blood was collected. The collected blood was immediately centrifuged at 4° C. at 15,000 rpm, so as to separate plasma.

50 µl of PBS that contained 0.05% Tween 20 was added to 50 µl of a plasma sample. Thereafter, the fluorescence intensity of the solution was measured using a fluorescence detector. Moreover, a standard curve was produced using an administration solution, and using the standard curve, the plasma concentration was calculated based on the total fluorescence intensity. After the measurement of the fluorescence intensity, the plasma sample was subjected to GPC under the conditions as described below, so as to measure the ratio of the fluorescence intensity of the HA-FITC labeled Fab conjugate and FITC-labeled Fab to the total fluorescence intensity. The plasma concentration based on the total fluorescence intensity was multiplied by the above ratio, so as to calculate the concentrations of the HA-FITC labeled Fab conjugate and FITC-labeled Fab in plasma.

Figure 27:
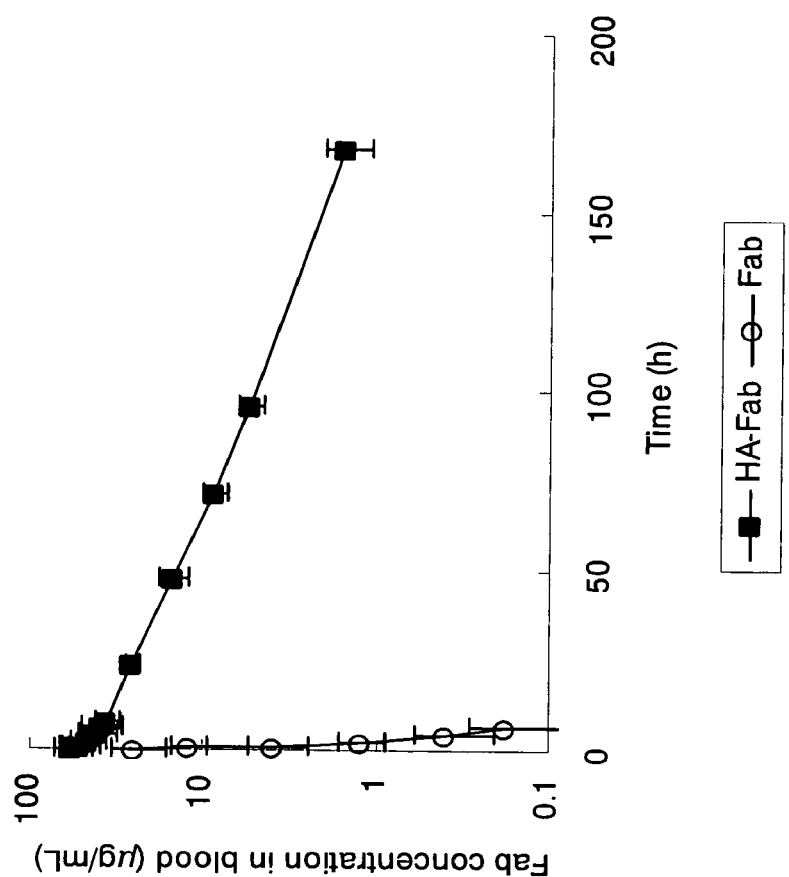
FIG. 27 is a view showing changes in the plasma concentrations obtained when HA-fluorescein isothiocyanate (hereinafter also referred to as "FITC")-labeled Fab conjugate and FITC-labeled Fab have been administered to rats as a single dose via intravenous administration.

In both cases of the HA-FITC labeled Fab conjugate administration group and FITC-labeled Fab administration group, the plasma concentration was decreased in a biphasic manner (FIG. 27). The half-life of the disappearance phase of FITC-labeled Fab was 1.50 hours, and thus the FITC-labeled Fab rapidly disappeared from circulating blood. In contrast, the half-life of the HA-FITC-labeled Fab conjugate was 38.89 hours. Thus, it was confirmed that the retention ability in blood of the HA-FITC-labeled Fab conjugate was significantly extended.

GPC Conditions

System: LC-10A (Shimadzu Corporation) or Waters 600S (Waters)

Fluorescence detector: L-7480 (Hitachi, Ltd.) or Waters 474 (Waters)

GPC column: TSKgel G6000PW$_{XL}$ (manufactured by TOSOH)

Mobile phase: PBS that contains 0.05% Tween 20

Flow ratio: 0.5 ml/min

Detection: fluorescence intensity at 518 nm by excitation at 490 nm

Example 15

Preparation of Water-Soluble Modified HA-GLP-1 Conjugate

Example 15-1

Preparation of HA-AM-MI/SUC

An HA-AM (EDOBEA introduction ratio: 95.5%) aqueous solution (10 mg/ml, 17.66 ml) was obtained in the same manner as that in Example 3-1 with the exception that a BOP reagent was used at an equivalent ratio of 2.5 to an HA unit. Thereafter, a 0.2 M phosphate buffer (pH 7.0; 22.075 ml) was added to the obtained HA-AM aqueous solution. A DMSO solution (0.573 mg/ml, 4.415 ml) of N-[κ-maleimidoundecanoyloxy]-sulfosuccinimide ester (Sulfo-KMUS; manufactured by Pierce) was added to the above solution, and the obtained mixture was then shaken at room temperature for 30 minutes. Thereafter, a succinic anhydride DMSO solution (283.95 mg/ml, 4.415 ml) was added to the reaction solution, and the obtained mixture was then further shaken at room temperature for 1.5 hours. Thereafter, the reaction solution was dialyzed against large excess amount of distilled water (Milli Q water) at 4° C. (Spectrapore 4; MWCO: 12 k-14 kDa) for purification. The obtained solution was freeze-dried, so as to obtain a modified hyaluronic acid into which a maleimide group and succinic acid had been introduced (hereinafter also referred to as "HA-AM-MI/SUC"; 177.80 mg).

Example 15-2

Preparation of HA-GLP-1 Mutant Conjugate Solution

A solid-phase peptide synthetic method (manufactured by Peptide Institute, Inc.) was applied to obtain a mutant (hereinafter also referred to as "GLP-1 mutant"), wherein, in natural GLP-1 (Human, 7-37; described in National Publication of International Patent Application No. 7-504679), the second alanine (at position 8) was substituted with glycine and the 31$^{st}$ glycine (at position 37) was substituted with cysteine. Thereafter, 1/20 volume of a tris[2-carboxyethyl]phosphine hydrochloride (hereinafter also referred to as "TCEP") aqueous solution (20 mM) was added to a 0.2 M phosphate buffer (pH 7.0) solution that contained the GLP-1 mutant (2.0 mg/ml). This GLP-1 mutant solution that contained TCEP (1.3263 ml) was added to the HA-AM-MI/SUC aqueous solution (20 mg/ml, 1.2 ml) obtained in Example 15-1, and the obtained mixture was then incubated at 37° C. for 2 hours. The same GLP-1 mutant solution that contained TCEP (1.3263 ml) was added to the resultant again, and the same above incubation was then carried out. Thereafter, a 0.1 M phosphate buffer (pH 7.0) solution that contained a cysteine hydrochloride monohydrate (3.6 mg/ml, 0.3853 ml) was added to the resultant, and the obtained mixture was further incubated at 37° C. for 1 hour. The reaction mixture was divided into 3 portions, and the portions were then subjected to GPC under the conditions as described below, so as to fractionate a conjugate fraction. The fractionated fraction was concentrated to approximately 4.85 ml by centrifugal ultrafiltration (Vivaspin20; MWCO: 50000; manufactured by Funakoshi), so as to obtain the captioned HA-GLP-1 mutant conjugate solution. A sample obtained by conducting the same operations as those in the present example without using a GLP-1 mutant was used as a control for correction. Based on the absorbance of the obtained HA-GLP-1 mutant solution at 280 nm and the carbazole-sulfuric acid method, the GLP-1-mutant concentration, the HA-AM-MI/SUC concentration, and the GLP-1 mutant introduction ratio were calculated. As a result, it was found that the GLP-1-mutant concentration was 42.6 nmol/ml, the HA-AM-MI/SUC concentration was 3.54 mg/ml, and the GLP-1 mutant introduction ratio was 3.7/HA (mol/mol).

GPC conditions

System: FPLC (manufactured by Amersham Biosciences)

GPC Column: HiLoad 16/60 Superdex 200prep grade (manufactured by Amersham Biosciences)

Mobile phase: PBS (pH 7.4)

Flow ratio: 1.0 ml/min

Detection: UV (280 nm)

Method for Quantifying Modified HA by Carbazole-Sulfuric Acid Method

[Reagent]

Sulfuric acid solution: sulfuric acid solution that contained $Na_2B_4O_7 \cdot 10H_2O$ (25 mM)

Carbazole solution: ethanol solution that contained carbazole (1.25 mg/ml; 0.125%)

[Standard Substance]

A modified hyaluronic acid (HA-AM-SUC) formed by introducing only succinic anhydride into HA-AM was prepared in the same manner as that in Example 15-1 with the exception that a DMSO solution that contained N-[κ-maleimidoundecanoyloxy]-sulfosuccinimide ester was not added. The obtained modified hyaluronic acid was dissolved in PBS, resulting in a concentration of 0.5 mg/ml. From this 0.5 mg/ml HA-AM-SUC solution, a 2 times diluted series was prepared (5 points of concentrations: 0.03125 to 0.5 mg/ml).

[Quantification]

PBS (control), standard substances (0.2 ml each), and a solution obtained by 19.8 times diluting with PBS the HA-GLP-1 mutant conjugate solution obtained in Example 15-2 (0.2 ml) were added to a sulfuric acid solution (1 ml) that had been cooled on ice, so as to mix them. The obtained mixture was heated in a hot water bath for 25 minutes, and it was then cooled to room temperature with running water. Thereafter, a carbazole solution (40 μl) was added to each solution, and they were mixed. The thus obtained mixture was heated in a hot water bath again for 30 minutes, and it was then cooled to room temperature with running water. The absorbance at 530 nm was measured, and a calibration curve was then produced from the absorbance of the control and that of the standard substance. Thereafter, the concentration of the modified HA contained in the sample solution was quantified.

Test Example 5

Evaluation of Residence Time in Blood of HA-GLP-1 Mutant Conjugate

HA-GLP-1 Mutant Conjugate-Administered Rat Plasma Sample

The HA-GLP-1 mutant conjugate solution obtained in Example 15-2 was diluted with PBS that contained 0.05% Tween 80 (pH 7.4; hereinafter also referred to as "solvent Z"), and the thus diluted solution was then administered at a dosage of 50 μg/kg into the vein of a rat as a single dose. Thereafter, 1, 4, 8, 24, 48, 72, 96, and 168 hours after the administration, the blood was collected (heparin treatment). The blood was then centrifuged, so as to obtain plasma. This plasma sample was cryopreserved at −20° C. or less until measurement was carried out.

Measurement Method

A standard sample used for calibration curve and a measurement sample were dispensed into a 96-well plate of the GLP-1 (Active) ELISA KIT (Linco Research, Inc. America; hereinafter also referred to as "kit W"). Thereafter, they were analyzed using a microplate reader. Conditions for measurement are described below:

Microplate reader: SPECTRA MAX GEMINI (manufactured by Molecular Devices)

Detection: Fluorescence (EX: 355 nm, EM: 460 nm)

Preparation of Measurement Sample

Sample Used for Calibration Curve

The HA-GLP-1 mutant conjugate solution obtained in Example 15-2 was diluted with solvent Z and Assay Buffer included with kit W, so as to prepare standard solutions having concentrations of 12.8, 6.4, 3.2, 1.6, 0.8, 0.4, 0.2, 0.1 μg/ml and 0 μg/ml. Thereafter, 5 μl of normal rat plasma was added to this standard solution, so as to prepare a sample used for calibration curve.

Preparation of Measurement Sample

Assay Buffer included with kit W was added to the HA-GLP-1 mutant conjugate-administered rat plasma sample, so as to prepare a measurement sample.

Calculation of Concentration of Modified HA in Plasma

The concentration of the HA-GLP-1 mutant conjugate in plasma was calculated based on the calibration curve obtained from the fluorescence intensity of each standard sample using analysis software SOFTmax PRO (manufactured by Molecular Devices).

Pharmacokinetic Data

Figure 28:
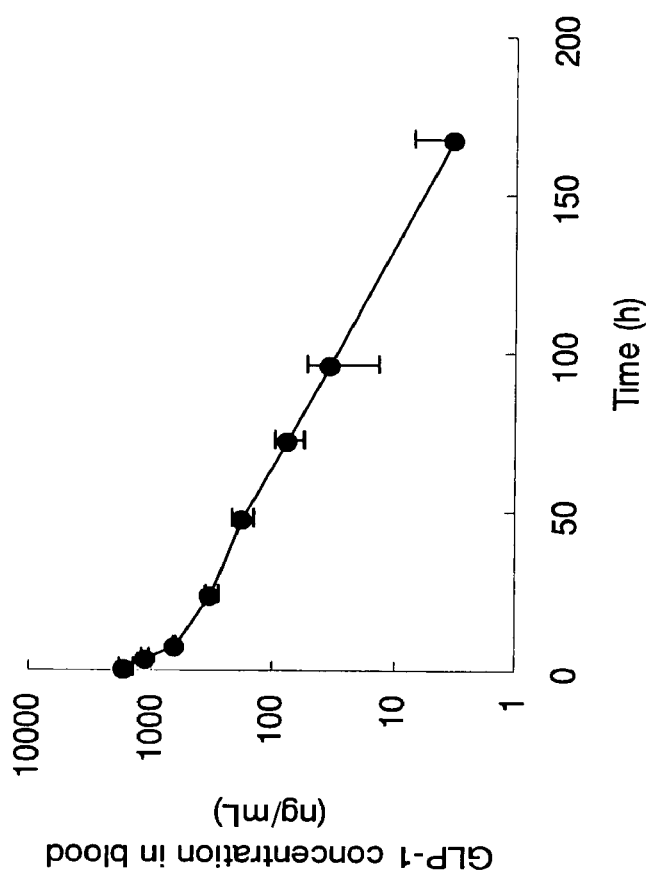
FIG. 28 is a view showing changes in the plasma concentrations obtained when an HA-GLP-1 mutant conjugate has been administered to rats via an intravenous administration.

With regard to data of a change in the concentration in blood of the administered HA-GLP-1 mutant conjugate, pharmacokinetic parameters were calculated using WinNonlin Ver 4.0.1 (manufactured by Pharsight). With regard to a change in the concentration in plasma of each individual, model-independent analysis was carried out, so as to calculate the mean residence time in blood (MRT). The half-life (t1/2) was calculated using the data of the final 3 measurable points of each individual. Such a change in the concentration in blood of the HA-GLP-1 mutant conjugate is shown in FIG. 28. Moreover, the calculated pharmacokinetic parameters are shown in Table 12.

TABLE 12

Pharmacokinetic parameters obtained when HA-GLP-1 mutant conjugate is administered into rat vein

|  | Mean value | Standard deviation |  |
|---|---|---|---|
| Half-life | 23.6 | 3.1 | (hr) |
| Total clearance | 1.8 | 0.1 | (mL/hr/kg) |
| Mean residence time in blood | 30.2 | 4.3 | (hr) |
| Distribution volume | 53.4 | 4.9 | (mL/kg) |

It has been reported that when natural GLP-1 and a mutant thereof wherein the second alanine has been substituted with glycine in the natural GLP-1 are intravenously administered to a human and a swine, its half-life is 1 to 5 minutes (Current Medicinal Chemistry, Vol. 10, pp. 2471-2483, 2003; and Diabetologia, Vol. 41, pp. 271-278, 1998). From FIG. 28 and Table 12, it was suggested that the half-life obtained when the HA-GLP-1 mutant conjugate was intravenously administered to a rat was 23.6 hours, and MRT was 30.2 hours, and that when compared with natural GLP-1, the retention ability in blood was significantly extended.

Text example 5

Oral Sugar Tolerance Test 8-week-old male BKS.Cg-+Lepr$^{db}$/+Lepr$^{db}$/Jcl mouse (manufactured by CLEA Japan, Inc.) was subjected to fasting overnight. Thereafter, the HA-GLP-1 mutant conjugate solution obtained in Example 15-2 that had been diluted with solvent Z (peptide amount: 1.5 μg/kg, 15 μg/kg, or 150 μg/kg) or solvent Z was intravenously administered to the above rat. 1 minute after the intravenous administration, a 50% glucose solution (Otsuka Pharmaceutical Co., Ltd.) was orally administered at a dosage of 3 g/kg. Likewise, the GLP-1 (Human, 7-37; manufactured by Peptide Institute, Inc.) that had been diluted with solvent Z (150 μg/kg or 1500 μg/kg) or solvent Z was intravenously administered to the above rat. 1 minute after the intravenous administration, the 50% glucose solution was orally administered at a dosage of 3 g/kg.

The blood was collected from the tail portion before administration of glucose (value at hour 0), and 0.5, 1, 2, and 4 hours after the administration of glucose. Thereafter, the blood glucose level was measured by the enzyme method (hexokinase method, Autosera S GLU (Daiichi Pure Chemical Co., Ltd.; equipment name: BioMajesty JCA-BM1250 (JEOL Ltd.)).

The blood glucose level was calculated by the following hypoglycemic ratio:

$$\text{Hypoglycemic ratio (\%)} = \frac{\begin{array}{c}\text{Mean value of } AUC \text{ of hyperglycemic}\\ \text{value of solvent administration group} -\\ AUC \text{ of hyperglycemic value of each individual}\end{array}}{\text{Mean value of } AUC \text{ of hyperglycemic}\\ \text{value of solvent administration group}} \times 100$$ [Formula 14]

The term "AUC of hyperglycemic value" is used herein to mean a value obtained by subtracting the area under the curve of a graph obtained when the blood glucose level of each individual before administration of glucose is constant without any changes until 4 hours after the administration of glucose, from the area under the curve of a graph obtained by plotting the time passed after administration of glucose in the horizontal axis and the blood glucose level of each individual in the longitudinal axis, and connecting points with straight lines. Specifically, under definitions such as $A^1$=blood glucose level obtained before administration of glucose, $B^1$=blood glucose level obtained 30 minutes after administration of glucose, $C^1$=blood glucose level obtained 1 hour after administration of glucose, $D^1$=blood glucose level obtained 2 hours after administration of glucose, and $E^1$=blood glucose level obtained 4 hours after administration of glucose, the AUC of a hyperglycemic value can be obtained according to the following formula:

$$AUC = 0.5 \times \frac{A^1 + B^1}{2} + 0.5 \times \frac{B^1 + C^1}{2} +$$
$$1 \times \frac{C^1 + D^1}{2} + 2 \times \frac{D^1 + E^1}{2} - 4 \times A^1$$
[Formula 15]

The mean value and standard deviation of each group were calculated from the calculated hypoglycemic ratio. The results are shown in Tables 13 and 14. When the HA-GLP-1 mutant conjugate was compared with GLP-1 (Human, 7-37), its hypoglycemic action was significantly increased, and thus, the effectiveness of the HA-GLP-1 mutant conjugate as a therapeutic agent for diabetes was suggested.

TABLE 13

Hypoglycemic ratio (%) when GLP-1 (Human, 7-37) is administered

| Dosage | Mean value | Standard deviation |
|---|---|---|
| 150 µg/kg | 15.3 | 35.6 |
| 1500 µg/kg | 59.6 | 42.4 |

TABLE 14

Hypoglycemic ratio (%) when HA-GLP-1 mutant conjugate is administered

| Dosage | Mean value | Standard deviation |
|---|---|---|
| 1.5 µg/kg | 3.0 | 28.1 |
| 15 µg/kg | 60.1 | 51.4 |
| 150 µg/kg | 120.3 | 35.6 |

The invention claimed is:

1. A process for preparing hyaluronic acid gel, which comprises steps of:

preparing a modified hyaluronic acid by converting a carboxy group contained in the glucuronic acid portion of hyaluronic acid or a salt thereof to a substituted amide group at a modification ratio of 10 mole % to 30 mole % in a solvent consisting of dimethyl sulfoxide, using a condensing agent represented by the following formula (II):

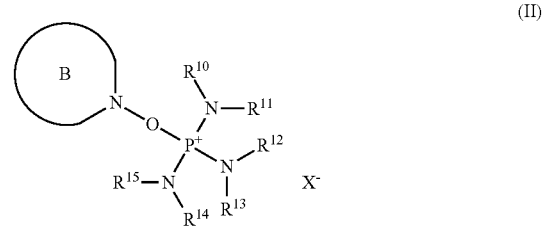

wherein each of $R^{10}$, $R^{11}$, $R^{12}$, $R^{13}$, $R^{14}$, and $R^{15}$ is independently selected from a $C_{1-6}$ alkyl group, or each of $R^{10}$ and $R^{11}$, $R^{12}$ and $R^{13}$, and $R^{14}$ and $R^{15}$ may independently from a nitrogen-containing heterocycle together with a nitrogen atom to which they are attached; ring B represents a monocyclic or condensed ring nitrogen-containing heterocycle group that may be substituted; and $X^-$ represents an anion;

wherein the substituted amide group is formed by allowing hyaluronic acid or a salt thereof to react with one or more compounds selected from the following formulas:

$H_2N-(CH_2)_l-O-CO-C(R^{16})=CH_2$;

$H_2N-(CH_2)_q-NHCO-C(R^{17})=CH_2$;

$H_2N-CH_2-CH_2-(Y^4-CH_2-CH_2)_t-NHCO-C(R^{18})=CH_2$; or $H_2N-CH_2-CH_2-(Y^5-CH_2-CH_2)_y-O-CO-C(R^{19})=CH_2$ wherein each of l, and q independently represents an integer selected from 2 to 10; each of t, and y independently represents an integer selected from 1 to 200; each of $R^{16}$, $R^{17}$, $R^{18}$, and $R^{19}$ independently represents a hydrogen atom or a methyl group; and each of $Y^4$, and $Y^5$ independently represents an oxygen atom or —NH—, and wherein the modification ratio is defined as a ratio of total number of substituted amide groups relative to the total number of the carboxy groups originally contained in the hyaluronic acid or the salt thereof; and cross-linking the modified hyaluronic acid to obtain hyaluronic acid gel.

2. The process according to claim 1, which is used for encapsulation of a drug.

3. The process according to claim 1, wherein a drug which can be encapsulated is a conjugate consisting of a polymer and a drug.

4. The process according to claim 1, which further comprises drying the hyaluronic acid gel.

5. The process according to claim 4, which is used for encapsulation of a drug.

6. The process according to claim 4, wherein a drug which can be encapsulated is a conjugate consisting of a polymer and a drug.

* * * * *